United States Patent
Allawi et al.

(10) Patent No.: US 12,098,431 B2
(45) Date of Patent: *Sep. 24, 2024

(54) DETECTION OF LUNG NEOPLASIA BY AMPLIFICATION OF RNA SEQUENCES

(71) Applicant: Exact Sciences Corporation, Madison, WI (US)

(72) Inventors: Hatim Allawi, Middleton, WI (US); Graham P. Lidgard, La Jolla, CA (US); Chateen Krueger, Fitchburg, WI (US); Michael W. Kaiser, Stoughton, WI (US); Tamara J. Sander, Mazomanie, WI (US)

(73) Assignee: Exact Sciences Corporation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/932,574

(22) Filed: Sep. 15, 2022

(65) Prior Publication Data

US 2023/0121671 A1 Apr. 20, 2023

Related U.S. Application Data

(63) Continuation of application No. 17/078,924, filed on Oct. 23, 2020, now Pat. No. 11,479,823, which is a continuation of application No. 15/587,806, filed on May 5, 2017, now abandoned.

(60) Provisional application No. 62/332,419, filed on May 5, 2016.

(51) Int. Cl.
*C12Q 1/6886* (2018.01)

(52) U.S. Cl.
CPC ...... *C12Q 1/6886* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,965,188 A | 10/1990 | Mullis et al. |
| 5,011,769 A | 4/1991 | Duck et al. |
| 5,124,246 A | 6/1992 | Urdea et al. |
| 5,288,609 A | 2/1994 | Engelhardt et al. |
| 5,338,671 A | 8/1994 | Scalice et al. |
| 5,403,711 A | 4/1995 | Walder et al. |
| 5,409,818 A | 4/1995 | Davey et al. |
| 5,494,810 A | 2/1996 | Barany et al. |
| 5,508,169 A | 4/1996 | Deugau et al. |
| 5,624,802 A | 4/1997 | Urdea et al. |
| 5,639,611 A | 6/1997 | Wallace et al. |
| 5,660,988 A | 8/1997 | Duck et al. |
| 5,710,264 A | 1/1998 | Urdea et al. |
| 5,773,258 A | 6/1998 | Birch et al. |
| 5,792,614 A | 7/1998 | Herman et al. |
| 5,846,717 A | 8/1998 | Western et al. |
| 5,849,481 A | 12/1998 | Brow et al. |
| 5,851,770 A | 12/1998 | Urdea et al. |
| 5,882,867 A | 3/1999 | Ullman et al. |
| 5,914,230 A | 3/1999 | Ullman et al. |
| 5,958,692 A | 6/1999 | Liu et al. |
| 5,965,408 A | 9/1999 | Cotton et al. |
| 5,985,557 A | 10/1999 | Short |
| 5,994,069 A | 11/1999 | Prudent et al. |
| 6,001,567 A | 11/1999 | Hall et al. |
| 6,013,170 A | 1/2000 | Meade |
| 6,063,573 A | 1/2000 | Meade |
| 6,090,543 A | 5/2000 | Kayyem |
| 6,110,677 A | 7/2000 | Prudent et al. |
| 6,110,684 A | 8/2000 | Western et al. |
| 6,121,001 A | 8/2000 | Kemper et al. |
| 6,150,097 A | 9/2000 | Western et al. |
| 6,183,960 B1 | 2/2001 | Lizardi |
| 6,210,884 B1 | 2/2001 | Lizardi |
| 6,221,583 B1 | 4/2001 | Lizardi |
| 6,235,502 B1 | 4/2001 | Kayyem et al. |
| 6,248,229 B1 | 5/2001 | Weissman et al. |
| 6,528,254 B1 | 3/2003 | Sorge |
| 6,630,333 B1 | 10/2003 | Hughes, Jr. |
| 6,872,816 B1 | 3/2005 | Hall et al. |
| 7,662,594 B2 | 2/2010 | Kong et al. |
| 8,206,904 B2 | 6/2012 | Allawi et al. |
| 8,361,720 B2 | 1/2013 | Oldham-Haltom et al. |
| 8,715,937 B2 | 5/2014 | Zou et al. |
| 8,916,344 B2 | 12/2014 | Zou et al. |
| 9,096,893 B2 | 8/2015 | Allawi et al. |

(Continued)

FOREIGN PATENT DOCUMENTS

| | | |
|---|---|---|
| WO | WO 2002/070755 | 9/2002 |
| WO | WO 2005/023091 | 3/2005 |

(Continued)

OTHER PUBLICATIONS

Affymetrix probes from the Affymetrix U133 array, downloaded Dec. 4, 2018, 16 pages.

Ballabio, et al., Screening for steroid sulfatase (STS) gene deletions by multiplex DNA amplification, Human Genetics, 1990, 84(6): 571-573.

Barnay, Genetic disease detection and DNA amplification using cloned thermostable ligase, Proc. Natl. Acad. Sci USA, 1991, 88:189-93.

Budd et al., Circulating tumor cells versus imaging—predicting overall survival in metastatic breast cancer. Clin Cancer Res. Nov. 1, 2006;12(21):6403-9.

(Continued)

*Primary Examiner* — Katherine D Salmon
(74) *Attorney, Agent, or Firm* — Casimir Jones, S.C.; Mary Ann D. Brow

(57) ABSTRACT

Provided herein is technology for lung neoplasia screening and particularly, but not exclusively, to methods, compositions, and related uses for detecting the presence of lung cancer.

16 Claims, 8 Drawing Sheets
Specification includes a Sequence Listing.

(56) References Cited

U.S. PATENT DOCUMENTS

| | | |
|---|---|---|
| 9,212,392 B2 | 12/2015 | Allawi et al. |
| 10,385,406 B2 | 8/2019 | Allawi et al. |
| 2007/0202525 A1 | 8/2007 | Quake et al. |
| 2009/0253142 A1 | 10/2009 | Allawi et al. |
| 2011/0052488 A1 | 3/2011 | Dennis, Jr. et al. |
| 2012/0094843 A1* | 4/2012 | Meier ............... C07K 16/3015 435/7.1 |
| 2014/0087382 A1 | 3/2014 | Allawi et al. |
| 2014/0363471 A1 | 12/2014 | Hu et al. |
| 2017/0121757 A1 | 5/2017 | Lidgard et al. |
| 2017/0335401 A1 | 11/2017 | Allawi et al. |
| 2018/0245157 A1 | 8/2018 | Allawi et al. |

FOREIGN PATENT DOCUMENTS

| | | |
|---|---|---|
| WO | WO 2006/050499 | 5/2006 |
| WO | WO 2017/075061 | 5/2017 |
| WO | WO 2017/192221 | 11/2017 |

OTHER PUBLICATIONS

Bustin, Absolute quantification of mRNA using real-time reverse transcription polymerase chain reaction assays, J. Molecular Endocrinology, 2000, 25:169-193.

Chamberlain et al., Deletion screening of the Duchenne muscular dystrophy locus via multiplex DNA amplification, Nucleic Acids Research, 1988, 16(23):11141-11156.

Cohen et al., Relationship of circulating tumor cells to tumor response, progression-free survival, and overall survival in patients with metastatic colorectal cancer. J Clin Oncol. Jul. 1, 2008;26(19):3213-21.

Cristofanilli et al., Circulating tumor cells, disease progression, and survival in metastatic breast cancer. N Engl J Med. Aug. 19, 2004;351(8):781-91.

Don et al., 'Touchdown' PCR to circumvent spurious priming during gene amplification, Nucleic Acids Research, 1991, 19(14):4008.

Guilfoyle et al., Ligation-mediated PCR amplification of specific fragments from a class-II restriction endonuclease total digest, Nucleic Acids Research, 1997, 25:1854-1858.

Hall et al., Sensitive detection of DNA polymorphisms by the serial invasive signal amplification reaction, PNAS, 2000, 97:8272.

Hayden et al., Multiplex-Ready PCR: A new method for multiplexed SSR and SNP genotyping, BMC Genomics, 2008, 9:80.

Hayes et al., Circulating tumor cells at each follow-up time point during therapy of metastatic breast cancer patients predict progression-free and overall survival. Clin Cancer Res. Jul. 15, 2006;12(14 Pt 1):4218-24.

Hecker et al., High and low annealing temperatures increase both specificity and yield in touchdown and stepdown PCR, Biotechniques, 1996, 20(3):478-485.

Higuchi et al., A general method of in vitro preparation and specific mutagenesis of DNA fragments: study of protein and DNA interactions, Nucleic Acids Research, 1988, 16(15):7351-7367.

Higuchi et al., Simultaneous amplification and detection of specific DNA sequences, Biotechnology, 1992, 10:413-417.

Higuchi et al.,Kinetic PCR analysis: real-time monitoring of DNA amplification reactions, Biotechnology, 1993, 11:1026-1030.

Kaiser et al., A comparison of eubacterial and archaeal structure-specific 5'-exonucleases. J Biol Chem. Jul. 23, 1999;274(30):21387-94.

Kalinina et al., Nanoliter scale PCR with TaqMan detection, Nucleic Acids Research, 1997, 25:1999-2004.

Lyamichev et al., Polymorphism identification and quantitative detection of genomic DNA by invasive cleavage of oligonucleotide probes, Nat. Biotech., 1999, 17:292-296.

Moreno et al., Circulating tumor cells predict survival in patients with metastatic prostate cancer. Urology. Apr. 2005;65(4): 713-8.

Olivier, The Invader assay for SNP genotyping, Mutat Res. Jun. 3, 2005;573(1-2):103-10.

Orpana, Fluorescence resonance energy transfer (FRET) using ssDNA binding fluorescent dye, Biomol Eng. Apr. 2004;21(2):45-50.

Pantel et al., Detection, clinical relevance and specific biological properties of disseminating tumour cells. Nat Rev Cancer. May 2008;8(5):329-40.

Roux, Using mismatched primer-template pairs in touchdown PCR, Biotechniques, 1994, 16(5):812-814.

Schouten et al., Relative quantification of 40 nucleic acid sequences by multiplex ligation-dependent probe amplification, Nucleic Acids Research, 2002, 30(12): e57.

Selvin, Fluorescence resonance energy transfer, 1995, Methods Enzymol. 1995;246:300-34.

Shen et al., Multiple but dissectible functions of FEN-1 nucleases in nucleic acid processing, genome stability and diseases. Bioessays. Jul. 2005;27(7):717-29.

Stryer, Fluorescence energy transfer as a spectroscopic ruler, Annu Rev Biochem. 1978;47:819-46.

Triglia et al., A procedure for in vitro amplification of DNA segments that lie outside the boundaries of known sequences, Nucleic Acids Res., 1988, 16:8186.

Vogelstein et al., Digital PCR, PNAS, 1999, 96: 9236-41.

\* cited by examiner

FIG. 2

| MMLV (units) | RT time (min) | Log (RNA strands) | RNA Strands | Positivity (%) | Average Cp | Average Strands | Slope | Intercept | % Efficiency |
|---|---|---|---|---|---|---|---|---|---|
| 2 | 10 | 6 | 1,000,000 | 100% | 16 | 1,176,093 | -3.17 | 35.4 | 106.99% |
| | | 5 | 100,000 | 100% | 20 | 95,350 | | | |
| | | 4 | 10,000 | 100% | 23 | 7,079 | | | |
| | | 3 | 1,000 | 50% | 25 | 1,690 | | | |
| | | 2 | 100 | 0% | NA | NA | | | |
| | | 1 | 10 | 0% | NA | NA | | | |
| | | 0 | 1 | 0% | NA | NA | | | |
| MMLV (units) | RT time (min) | Log (RNA strands) | RNA Strands | Positivity (%) | Average Cp | Average Strands | Slope | Intercept | % Efficiency |
| 2 | 30 | 6 | 1,000,000 | 100% | 15.8 | 1429396 | -2.83 | 33.2 | 125.91% |
| | | 5 | 100,000 | 100% | 19.1 | 99202 | | | |
| | | 4 | 10,000 | 100% | 22.6 | 5748 | | | |
| | | 3 | 1,000 | 50% | 24.9 | 821 | | | |
| | | 2 | 100 | 50% | 26.6 | 219 | | | |
| | | 1 | 10 | 0% | NA | NA | | | |
| | | 0 | 1 | 0% | NA | NA | | | |
| MMLV (units) | RT time (min) | Log (RNA strands) | RNA Strands | Positivity (%) | Average Cp | Average Strands | Slope | Intercept | % Efficiency |
| 2 | 45 | 6 | 1,000,000 | 100% | 17.0 | 927417 | -3.40 | 37.3 | 96.78% |
| | | 5 | 100,000 | 100% | 20.0 | 116797 | | | |
| | | 4 | 10,000 | 100% | 23.8 | 9517 | | | |
| | | 3 | 1,000 | 0% | NA | NA | | | |
| | | 2 | 100 | 0% | NA | NA | | | |
| | | 1 | 10 | 0% | NA | NA | | | |
| | | 0 | 1 | 0% | NA | NA | | | |
| MMLV (units) | RT time (min) | Log (RNA strands) | RNA Strands | Positivity (%) | Average Cp | Average Strands | Slope | Intercept | % Efficiency |
| 4 | 10 | 6 | 1,000,000 | 100% | 16 | 1,007,096 | -3.62 | 37.3 | 88.87% |
| | | 5 | 100,000 | 100% | 19 | 116,764 | | | |
| | | 4 | 10,000 | 100% | 23 | 7,981 | | | |
| | | 3 | 1,000 | 50% | 26 | 1,392 | | | |
| | | 2 | 100 | 0% | NA | NA | | | |
| | | 1 | 10 | 0% | NA | NA | | | |
| | | 0 | 1 | 0% | NA | NA | | | |
| MMLV (units) | RT time (min) | Log (RNA strands) | RNA Strands | Positivity (%) | Average Cp | Average Strands | Slope | Intercept | % Efficiency |
| 4 | 30 | 6 | 1,000,000 | 100% | 15 | 1,136,170 | -3.25 | 34.9 | 103.28% |
| | | 5 | 100,000 | 100% | 18 | 127,887 | | | |
| | | 4 | 10,000 | 100% | 23 | 5,661 | | | |
| | | 3 | 1,000 | 100% | 25 | 1,067 | | | |
| | | 2 | 100 | 50% | 28 | 182 | | | |

FIG. 2 (cont'd)

| MMLV (units) | RT time (min) | Log (RNA strands) | RNA Strands | Positivity (%) | Average Cp | Average Strands | Slope | Intercept | % Efficiency |
|---|---|---|---|---|---|---|---|---|---|
| | | 1 | 10 | 0% | NA | NA | | | |
| | | 0 | 1 | 0% | NA | NA | | | |
| 4 | 45 | 6 | 1,000,000 | 100% | 16.2 | 1142850 | -2.96 | 34.1 | 117.88% |
| | | 5 | 100,000 | 100% | 19.4 | 98545 | | | |
| | | 4 | 10,000 | 100% | 22.8 | 7365 | | | |
| | | 3 | 1,000 | 100% | 25.0 | 1270 | | | |
| | | 2 | 100 | 0% | NA | NA | | | |
| | | 1 | 10 | 0% | NA | NA | | | |
| | | 0 | 1 | 0% | NA | NA | | | |
| MMLV (units) | RT time (min) | Log (RNA strands) | RNA Strands | Positivity (%) | Average Cp | Average Strands | Slope | Intercept | % Efficiency |
| 8 | 10 | 6 | 1000000 | 100% | 14.8 | 876339 | -3.60 | 36.2 | 89.60% |
| | | 5 | 100000 | 100% | 17.9 | 119599 | | | |
| | | 4 | 10000 | 100% | 21.7 | 10739 | | | |
| | | 3 | 1000 | 100% | 25.5 | 918 | | | |
| | | 2 | 100 | 0% | NA | NA | | | |
| | | 1 | 10 | 0% | NA | NA | | | |
| | | 0 | 1 | 0% | NA | NA | | | |
| MMLV (units) | RT time (min) | Log (RNA strands) | RNA Strands | Positivity (%) | Average Cp | Average Strands | Slope | Intercept | % Efficiency |
| 8 | 30 | 6 | 1,000,000 | 100% | 14.0 | 1020824 | -3.27 | 33.7 | 102.09% |
| | | 5 | 100,000 | 100% | 17.1 | 117192 | | | |
| | | 4 | 10,000 | 100% | 21.1 | 6996 | | | |
| | | 3 | 1,000 | 100% | 23.6 | 1226 | | | |
| | | 2 | 100 | 0% | NA | NA | | | |
| | | 1 | 10 | 0% | NA | NA | | | |
| | | 0 | 1 | 0% | NA | NA | | | |
| MMLV (units) | RT time (min) | Log (RNA strands) | RNA Strands | Positivity (%) | Average Cp | Average Strands | Slope | Intercept | % Efficiency |
| 8 | 45 | 6 | 1,000,000 | 100% | 15.0 | 971743 | -3.22 | 34.3 | 104.61% |
| | | 5 | 100,000 | 100% | 18.0 | 115078 | | | |
| | | 4 | 10,000 | 100% | 21.7 | 8496 | | | |
| | | 3 | 1,000 | 100% | 24.5 | 1082 | | | |
| | | 2 | 100 | 0% | NA | NA | | | |
| | | 1 | 10 | 0% | NA | NA | | | |
| | | 0 | 1 | 0% | NA | NA | | | |
| MMLV (units) | RT time (min) | Log (RNA strands) | RNA Strands | Positivity (%) | Average Cp | Average Strands | Slope | Intercept | % Efficiency |
| | | 6 | 1,000,000 | 100% | 14.0 | 1522369 | | | |
| | | 5 | 100,000 | 100% | 17.4 | 101278 | | | |

FIG. 2 (cont'd)

| MMLV (units) | RT time (min) | Log (RNA strands) | RNA Strands | Positivity (%) | Average Cp | Average Strands | Slope | Intercept | % Efficiency |
|---|---|---|---|---|---|---|---|---|---|
| 16 | 10 | 4 | 10,000 | 100% | 21.0 | 5331 | -2.84 | 31.6 | 124.98% |
| | | 3 | 1,000 | 100% | 23.3 | 834 | | | |
| | | 2 | 100 | 50% | 25.4 | 76 | | | |
| | | 1 | 10 | 50% | 28.3 | 7 | | | |
| | | 0 | 1 | 0% | NA | NA | | | |
| MMLV (units) | RT time (min) | Log (RNA strands) | RNA Strands | Positivity (%) | Average Cp | Average Strands | Slope | Intercept | % Efficiency |
| 16 | 30 | 6 | 1,000,000 | 100% | 13.3 | 1162259 | -3.06 | 31.9 | 112.39% |
| | | 5 | 100,000 | 100% | 16.5 | 106440 | | | |
| | | 4 | 10,000 | 100% | 20.2 | 6802 | | | |
| | | 3 | 1,000 | 100% | 22.7 | 1019 | | | |
| | | 2 | 100 | 100% | 25.5 | 119 | | | |
| | | 1 | 10 | 0% | NA | NA | | | |
| | | 0 | 1 | 0% | NA | NA | | | |
| MMLV (units) | RT time (min) | Log (RNA strands) | RNA Strands | Positivity (%) | Average Cp | Average Strands | Slope | Intercept | % Efficiency |
| 16 | 45 | 6 | 1,000,000 | 100% | 14.6 | 984355 | -3.17 | 33.6 | 106.78% |
| | | 5 | 100,000 | 100% | 17.7 | 103465 | | | |
| | | 4 | 10,000 | 100% | 20.9 | 9870 | | | |
| | | 3 | 1,000 | 0% | NA | NA | | | |
| | | 2 | 100 | 0% | NA | NA | | | |
| | | 1 | 10 | 0% | NA | NA | | | |
| | | 0 | 1 | 0% | NA | NA | | | |
| MMLV (units) | RT time (min) | Log (RNA strands) | RNA Strands | Positivity (%) | Average Cp | Average Strands | Slope | Intercept | % Efficiency |
| 32 | 10 | 6 | 1,000,000 | 100% | 15 | 1,244,785 | -3.01 | 32.9 | 114.78% |
| | | 5 | 100,000 | 100% | 18 | 101,820 | | | |
| | | 4 | 10,000 | 100% | 21 | 7,079 | | | |
| | | 3 | 1,000 | 100% | 24 | 876 | | | |
| | | 2 | 100 | 50% | 26 | 188 | | | |
| | | 1 | 10 | 0% | NA | NA | | | |
| | | 0 | 1 | 0% | NA | NA | | | |
| MMLV (units) | RT time (min) | Log (RNA strands) | RNA Strands | Positivity (%) | Average Cp | Average Strands | Slope | Intercept | % Efficiency |
| 32 | 30 | 6 | 1,000,000 | 100% | 13.4 | 1166910 | -2.89 | 30.9 | 121.94% |
| | | 5 | 100,000 | 100% | 16.5 | 94672 | | | |
| | | 4 | 10,000 | 100% | 19.8 | 7302 | | | |
| | | 3 | 1,000 | 100% | 21.9 | 1306 | | | |
| | | 2 | 100 | 0% | NA | NA | | | |
| | | 1 | 10 | 0% | NA | NA | | | |
| | | 0 | 1 | 0% | NA | NA | | | |
| MMLV (units) | RT time (min) | Log (RNA strands) | RNA Strands | Positivity (%) | Average Cp | Average Strands | Slope | Intercept | % Efficiency |

FIG. 2 (cont'd)

| MMLV (units) | RT time (min) | Log (RNA strands) | RNA Strands | Positivity (%) | Average Cp | Average Strands | Slope | Intercept | % Efficiency |
|---|---|---|---|---|---|---|---|---|---|
| 32 | 45 | 6 | 1,000,000 | 100% | 14.8 | 941782 | -3.07 | 33.1 | 111.60% |
| | | 5 | 100,000 | 100% | 17.6 | 107487 | | | |
| | | 4 | 10,000 | 100% | 20.7 | 10662 | | | |
| | | 3 | 1,000 | 100% | 24.0 | 944 | | | |
| | | 2 | 100 | 0% | NA | NA | | | |
| | | 1 | 10 | 0% | NA | NA | | | |
| | | 0 | 1 | 0% | NA | NA | | | |
| MMLV (units) | RT time (min) | Log (RNA strands) | RNA Strands | Positivity (%) | Average Cp | Average Strands | Slope | Intercept | % Efficiency |
| 64 | 10 | 6 | 1,000,000 | 100% | 15.0 | 682439 | -3.77 | 37.0 | 84.15% |
| | | 5 | 100,000 | 100% | 17.8 | 125812 | | | |
| | | 4 | 10,000 | 100% | 20.8 | 19833 | | | |
| | | 3 | 1,000 | 100% | 26.5 | 806 | | | |
| | | 2 | 100 | 50% | 29.5 | 96 | | | |
| | | 1 | 10 | 0% | NA | NA | | | |
| | | 0 | 1 | 0% | NA | NA | | | |
| MMLV (units) | RT time (min) | Log (RNA strands) | RNA Strands | Positivity (%) | Average Cp | Average Strands | Slope | Intercept | % Efficiency |
| 64 | 30 | 6 | 1,000,000 | 100% | 14.4 | 607851 | -4.17 | 38.4 | 73.80% |
| | | 5 | 100,000 | 100% | 17.2 | 127785 | | | |
| | | 4 | 10,000 | 100% | 20.6 | 19204 | | | |
| | | 3 | 1,000 | 100% | 26.0 | 1174 | | | |
| | | 2 | 100 | 100% | 30.8 | 148 | | | |
| | | 1 | 10 | 0% | NA | NA | | | |
| | | 0 | 1 | 0% | NA | NA | | | |
| MMLV (units) | RT time (min) | Log (RNA strands) | RNA Strands | Positivity (%) | Average Cp | Average Strands | Slope | Intercept | % Efficiency |
| 64 | 45 | 6 | 1,000,000 | 100% | 15.0 | 582944 | -4.21 | 39.2 | 72.89% |
| | | 5 | 100,000 | 100% | 17.6 | 140634 | | | |
| | | 4 | 10,000 | 100% | 20.7 | 25564 | | | |
| | | 3 | 1,000 | 100% | 28.0 | 2324 | | | |
| | | 2 | 100 | 0% | NA | NA | | | |
| | | 1 | 10 | 0% | NA | NA | | | |
| | | 0 | 1 | 0% | NA | NA | | | |

FIG. 3
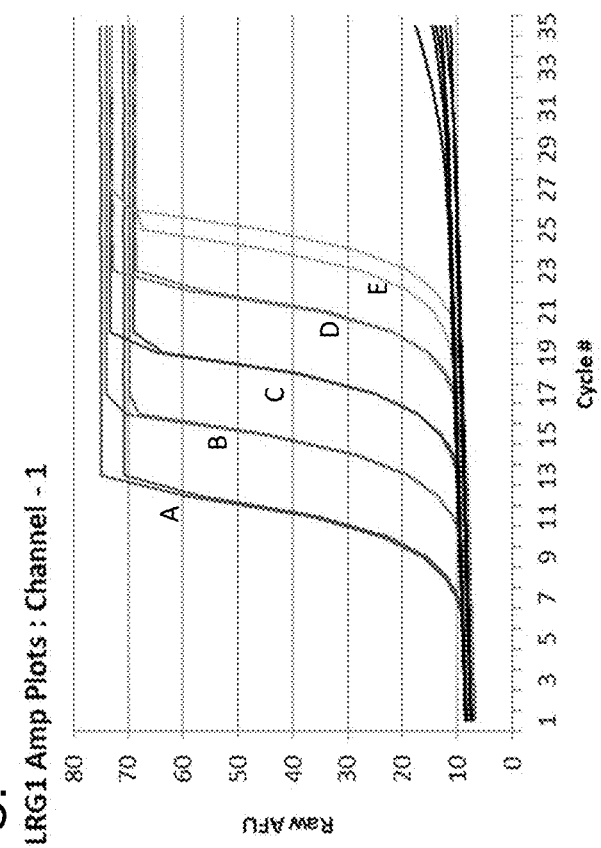
A.
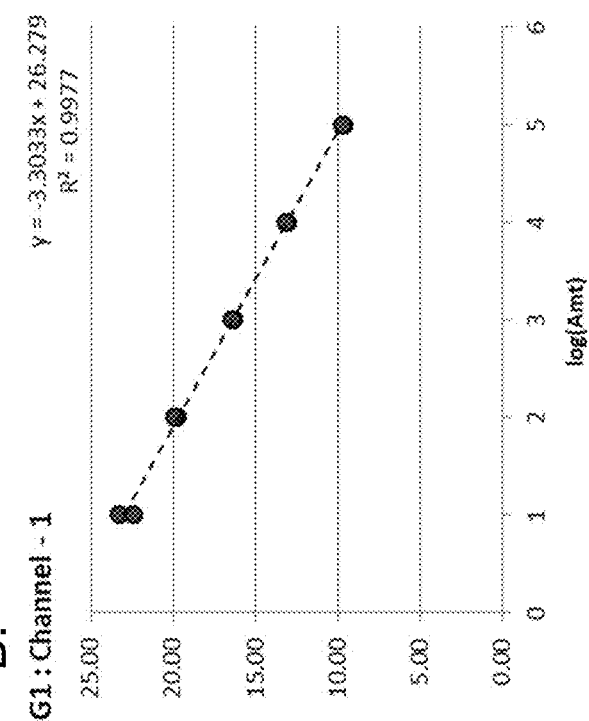
B.
C.

FIG. 5
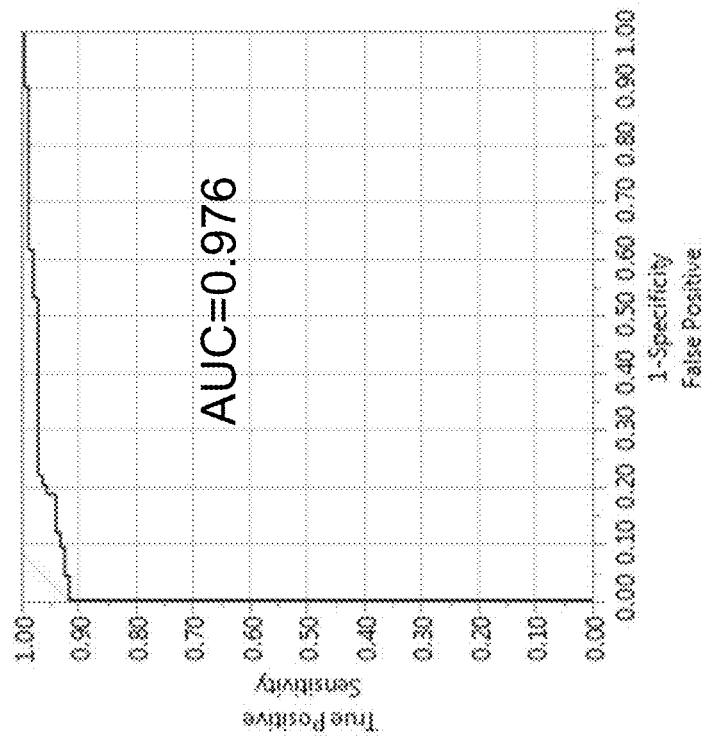
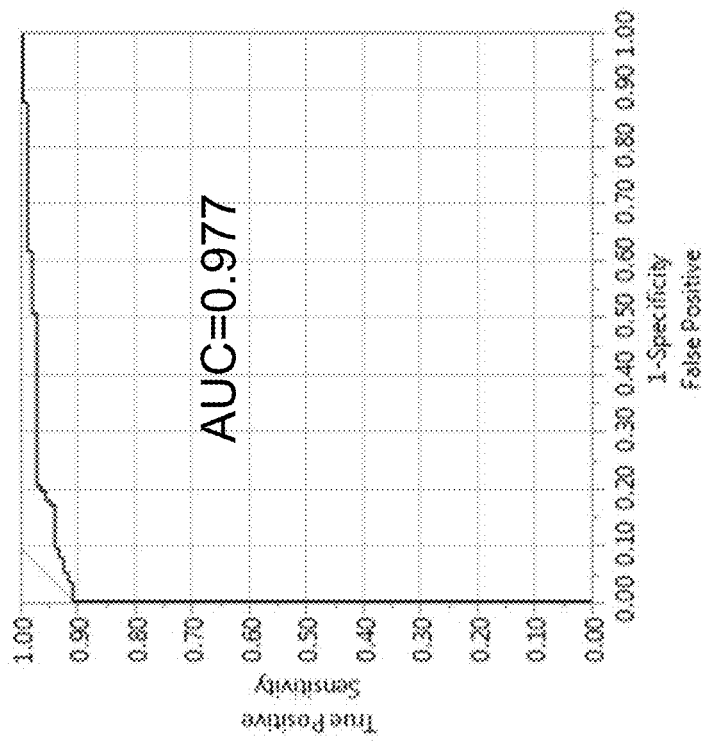

SEQUENCE LISTING

```
Sequence total quantity: 36
SEQ ID NO: 1                moltype = DNA   length = 24
FEATURE                     Location/Qualifiers
source                      1..24
                            mol_type = other DNA
                            organism = synthetic construct
SEQUENCE: 1
ggacactgag aagaaagacc agtc                                              24

SEQ ID NO: 2                moltype = DNA   length = 21
FEATURE                     Location/Qualifiers
source                      1..21
                            mol_type = other DNA
                            organism = synthetic construct
SEQUENCE: 2
gggagcttgt ttgaaaaggc a                                                 21

SEQ ID NO: 3                moltype = DNA   length = 21
FEATURE                     Location/Qualifiers
source                      1..21
                            mol_type = other DNA
                            organism = synthetic construct
SEQUENCE: 3
ccacggacgc taagacagag g                                                 21

SEQ ID NO: 4                moltype = DNA   length = 18
FEATURE                     Location/Qualifiers
source                      1..18
                            mol_type = other DNA
                            organism = synthetic construct
SEQUENCE: 4
ctgcaaccac gggaactt                                                     18

SEQ ID NO: 5                moltype = DNA   length = 18
FEATURE                     Location/Qualifiers
source                      1..18
                            mol_type = other DNA
                            organism = synthetic construct
SEQUENCE: 5
gaggtggagg tcctgctc                                                     18

SEQ ID NO: 6                moltype = DNA   length = 21
FEATURE                     Location/Qualifiers
source                      1..21
                            mol_type = other DNA
                            organism = synthetic construct
SEQUENCE: 6
gacgcggagt cgaggtatgc c                                                 21

SEQ ID NO: 7                moltype = DNA   length = 23
FEATURE                     Location/Qualifiers
source                      1..23
                            mol_type = other DNA
                            organism = synthetic construct
SEQUENCE: 7
cttcaactgc atttggctct ttg                                               23

SEQ ID NO: 8                moltype = DNA   length = 17
FEATURE                     Location/Qualifiers
source                      1..17
                            mol_type = other DNA
                            organism = synthetic construct
SEQUENCE: 8
tgtggcctgg atgtcgt                                                      17

SEQ ID NO: 9                moltype = DNA   length = 21
FEATURE                     Location/Qualifiers
source                      1..21
                            mol_type = other DNA
                            organism = synthetic construct
SEQUENCE: 9
ccacggacgg ttggattgtc c                                                 21

SEQ ID NO: 10               moltype = DNA   length = 23
FEATURE                     Location/Qualifiers
source                      1..23
                            mol_type = other DNA
                            organism = synthetic construct
```

```
SEQUENCE: 10
tggagatttg tcctgtctgg atc                                           23

SEQ ID NO: 11           moltype = DNA  length = 20
FEATURE                 Location/Qualifiers
source                  1..20
                        mol_type = other DNA
                        organism = synthetic construct
SEQUENCE: 11
cttggagagg atgttccggt                                               20

SEQ ID NO: 12           moltype = DNA  length = 21
FEATURE                 Location/Qualifiers
source                  1..21
                        mol_type = other DNA
                        organism = synthetic construct
SEQUENCE: 12
ccacggacgc ttacagcttc a                                             21

SEQ ID NO: 13           moltype = DNA  length = 18
FEATURE                 Location/Qualifiers
source                  1..18
                        mol_type = other DNA
                        organism = synthetic construct
SEQUENCE: 13
agggagcatc tgcaggtc                                                 18

SEQ ID NO: 14           moltype = DNA  length = 22
FEATURE                 Location/Qualifiers
source                  1..22
                        mol_type = other DNA
                        organism = synthetic construct
SEQUENCE: 14
cctgttcctg gctatgagct tc                                            22

SEQ ID NO: 15           moltype = DNA  length = 20
FEATURE                 Location/Qualifiers
source                  1..20
                        mol_type = other DNA
                        organism = synthetic construct
SEQUENCE: 15
cgccgaggca agggccgaag                                               20

SEQ ID NO: 16           moltype = DNA  length = 18
FEATURE                 Location/Qualifiers
source                  1..18
                        mol_type = other DNA
                        organism = synthetic construct
SEQUENCE: 16
gagcagacag cgaccaaa                                                 18

SEQ ID NO: 17           moltype = DNA  length = 25
FEATURE                 Location/Qualifiers
source                  1..25
                        mol_type = other DNA
                        organism = synthetic construct
SEQUENCE: 17
caggaacaga gttctagaaa catgg                                         25

SEQ ID NO: 18           moltype = DNA  length = 21
FEATURE                 Location/Qualifiers
source                  1..21
                        mol_type = other DNA
                        organism = synthetic construct
SEQUENCE: 18
ccacggacga aagcccaggg g                                             21

SEQ ID NO: 19           moltype = DNA  length = 21
FEATURE                 Location/Qualifiers
source                  1..21
                        mol_type = other DNA
                        organism = synthetic construct
SEQUENCE: 19
agaggagcac caaggagaag a                                             21

SEQ ID NO: 20           moltype = DNA  length = 19
FEATURE                 Location/Qualifiers
source                  1..19
                        mol_type = other DNA
```

```
                                    organism = synthetic construct
SEQUENCE: 20
ggcaaaagct gggcaatgg                                                            19

SEQ ID NO: 21           moltype = DNA  length = 20
FEATURE                 Location/Qualifiers
source                  1..20
                        mol_type = other DNA
                        organism = synthetic construct
SEQUENCE: 21
cgccgaggat ctgcctgtgg                                                           20

SEQ ID NO: 22           moltype = DNA  length = 22
FEATURE                 Location/Qualifiers
source                  1..22
                        mol_type = other DNA
                        organism = synthetic construct
SEQUENCE: 22
gtcatcgact acttccagaa cc                                                        22

SEQ ID NO: 23           moltype = DNA  length = 18
FEATURE                 Location/Qualifiers
source                  1..18
                        mol_type = other DNA
                        organism = synthetic construct
SEQUENCE: 23
aggtgcatac agatgccg                                                             18

SEQ ID NO: 24           moltype = DNA  length = 20
FEATURE                 Location/Qualifiers
source                  1..20
                        mol_type = other DNA
                        organism = synthetic construct
SEQUENCE: 24
cgccgaggca gactgactca                                                           20

SEQ ID NO: 25           moltype = DNA  length = 17
FEATURE                 Location/Qualifiers
source                  1..17
                        mol_type = other DNA
                        organism = synthetic construct
SEQUENCE: 25
cccaggtgct gggaagg                                                              17

SEQ ID NO: 26           moltype = DNA  length = 20
FEATURE                 Location/Qualifiers
source                  1..20
                        mol_type = other DNA
                        organism = synthetic construct
SEQUENCE: 26
actgatgcag ctcttgcaga                                                           20

SEQ ID NO: 27           moltype = DNA  length = 21
FEATURE                 Location/Qualifiers
source                  1..21
                        mol_type = other DNA
                        organism = synthetic construct
SEQUENCE: 27
ccacggacgg gaaatgcgcg a                                                         21

SEQ ID NO: 28           moltype = DNA  length = 2867
FEATURE                 Location/Qualifiers
source                  1..2867
                        mol_type = genomic DNA
                        organism = Homo sapiens
SEQUENCE: 28
cagggggtggc agccaactgc aggtgcccaa gaacttggca cttctcagtt ccatctaaag              60
gggcacatct cccttctggg tgtcacgttt tcagccaaac atctaaaaga acttcatcat             120
caagatgtct gatgatattg actggttacg cagccacagg ggtgtgtgca aggtagatct             180
ctacaaccca gaaggacagc aagatcagga ccggaaagtg atatgctttg tcgatgtgtc             240
caccctgaat gtagaagata agattacaa ggatgctgct agttccagct cagaaggcaa              300
cttaaacctg ggaagtctgg aagaaaaaga gattatcgtg atcaaggaca ctgagaagaa             360
agaccagtct aagacagagg gatctgtatg ccttttcaaa caagctccct ctgatcctgt             420
aagtgtcctc aactggcttc tcagtgatct ccagaagtaa gcctgggttt tccaacatgc             480
actgagcccc tcaacctcta cctgtaaaca taagtagga gacacagagg gcgaatatca              540
cagagcatcc tctgagaact gctacagtgt ctatgccgat caagtgaaca tagattattt             600
gatgaacaga cctcaaaaac ctacgtctag aatgacagca gctaaaaaca ccaacaataa             660
tcaaagtcct tcagctcctc cagccaaacc tcctagcact cagagagcag tcatttcccc             720
tgatggagaa tgttctatag atgacctttt ccttctacgt caa accgactat cttctctggt         780
```

-continued

```
aatccagatg gcccataagg aaatcaagga gaagttggaa ggtaaaagca aatgccttca   840
tcattcaatc tgtccatccc ctgggaacaa agagagaatc agtccccgaa ctcctgcgag   900
caagattgct tctgaaatgg cctatgaagc tgtggaactg acagctgcag aaatgcgtgg   960
cactggagag gagtccaggg aaggtggcca gaaaagcttt ctatatagcg aattatccaa  1020
caagagcaaa agtggagaca aacagatgtc ccagagagaa agcaaagaat ttgcagattc  1080
catcagcaag gggctcatgg tttatgcaaa tcaggtggca tctgacatga tggtctctct  1140
catgaagacc ttgaaagtgc acagctctgg gaagccaatt ccagcatctg tggtcctgaa  1200
gagggtgttg ctaaggcaca ccaaggagat tgtgtccgat tgattgatt cttgcatgaa  1260
gaacctgcat aatattactg gggtcctgat gactgactca gactttgtct cagctgtcaa  1320
gagaaatctg ttcaaccagt ggaaacaaaa tgctacagac atcatggagg ccatgctgaa  1380
gcgcttggtc agtgcccta taggtgagga gaaggagact aagtctcaga gtctgtcata  1440
tgcatcttta aaagctgggt cccatgatcc caaatgcagg aatcagagtc ttgaattctc  1500
caccatgaaa gctgaaatga agagaggga caaaggcaaa atgaaatcag acccagtgcaa  1560
gtcactgact agtgctgaga aagtcggtga acacattctc aaagagggcc taaccatctg  1620
gaaccaaaag caaggaaact catgcaaggt ggctaccaaa gcatgcagca ataaagatga  1680
gaaggagaa aagatcaatg cttccacaga ttcactggcc aaggacctga ttgtctctgc  1740
ccttaagctg atccagtacc atctgaccca gcagactaag ggcaaagata catgtgaaga  1800
agactgtcct ggttccacca tgggctatat ggctcagagt actcaatatg aaaagtgtgg  1860
aggtggccaa agtgccaaag cactttcagt gaaacaacta gaatctcaca gagcccctgg  1920
accatccacc tgtcaaaagg agaaccaaca cctggactcc cagaaaatgg atatgtcaaa  1980
catcgttcta atgctgattc agaaactgct taatgagaac cccttcaaat gtgaggatcc  2040
atgcgaaggt gagaacaagt gttctgagcc cagggcaagc agcatgcagc agtcaaggcc  2100
cagatctgac aaagcggaag aacaatgcca ggagcatcaa gaacttgact gtaccagtgg  2160
gatgaagcaa gcgaacgggc aatttataga taaactagta gaatctgtga tgaagctctg  2220
ccttatcatg gctaagtata gcaacgatgg ggcagccctt gctgagttgg aagaacaagc  2280
agcctcggca aataagccca attttcagggg caccagatgc attcacagtg gtgcaatgcc  2340
acagaactat caagactctc ttggacatga agtaattgtc aataatcagt gctctacaaa  2400
tagcttgcag aagcagctcc aggctgtcct gcagtggatt gcagcctccc agtttaacgt  2460
gcccatgctc tacttcatgg gagataagga tggacaactg gaaaagcttc ctcaggtttc  2520
agctaaagca gcagagaagg ggtacagtgt aggaagtt cttcaagagg tcatgaagtt  2580
tgccaaggaa cggcaaccag atgaagctgt gggaaaggtg gccaggaaac agttgctgga  2640
ctggctgctc gctaacctgt gagctgatcc ttgactcctc ttcatcttag ccccccctagc  2700
agcattccat cccagccaga gcaccccac catcaggcca gtcaactgca caatacacaa   2760
ctgtatttcc caatacactt gagcagttgc ctgtgaatgt aagaggtgtc aacaaactgg   2820
gaaataaaat aaaaaaaat aataaaaaaa aaaaaaaaa aaaaaa               2867
```

```
SEQ ID NO: 29        moltype = DNA   length = 4198
FEATURE              Location/Qualifiers
source               1..4198
                     mol_type = genomic DNA
                     organism = Homo sapiens
SEQUENCE: 29
aatccgggtc ggccgcaaac gtgccgcagg cctaggcccc gcccagtgcc ccgcccctcc    60
cccaacacac acacacacac acacacacac acaggcccca acacacacac acacacccca  120
acacacacac acacacacac acacacacac acacacacac acacacacac acacacagcg  180
ggatggccga gcgccgcacg cgtagcacgc cgggactagc tatccagcct cccagcagcc  240
tctgcgacgg gcgcggtgcg taagtacctc gccggtgctg gccgttctcc gtaagatgcc  300
ggaccggcgg cggcagcgcg cttcgcaaga caccgaggac gaggaatctg tgcttcggg   360
ctccgacagc ggcggctccc cgttgcgggg aggcgggagc tgcagcggta gcgccggagg  420
cggcggcagc ggctctctgc cttcacagcg cggaggccga accggggccc ttcatctgcg  480
gcgggtggag agcgggggcg ccaagagtgc tgaggagtcg gagtgtgaga gtgaagatgg  540
cattgaaggt gatgctgttc tctcggatta tgaaagtgca gaagactcgg aaggtgaaga  600
aggtgaatac agtgaagagg aaaactccaa agtggagctg aaatcagaag ctaatgatgc  660
tgttaattct tcaacaaaag aagagaaggg agaagaaaag cctgacacca aaagcactgt  720
gactggagag aggcaaagtg gggacggaca ggagagcaca gagcctgtgg agaacaaagt  780
gggtaaaaag ggccctaagc atttggatga tgatgaagat cggaagaatc cagcatacat  840
acctcggaaa gggctcttct ttgagcatga tcttcgaggg caaactcagg aggaggaagt  900
cagacccaag gggcgtcagc gaaagctatg gaaggatgag ggtcgctggg agcatgacaa  960
gttccgggaa gatgagcagg ccccaaagtc ccgacaggag ctcattgctc tttatggtta  1020
tgacattcgc tcagctcata atcctgatga catcaaacct cgaagaatcc ggaaacccg   1080
atatgggagt cctccacaaa gagatccaaa ctggaacggt gagcggctaa caagtctca   1140
tcgccaccag ggtcttgggg gcaccctacc accaaggaca tttattaaca ggaatgctgc   1200
aggtaccggc cgtatgtctg cacccaggaa ttattctcga tctgggggct tcaaggaagg  1260
tcgtgctggt tttaggcctg tggaagctgg tgggcagcac ggtggccggt ctggtgagca  1320
tgttaagcat gagattagtt accggtcacg gcgcctagag cagacttctg tgagggatcc  1380
atctccagaa gcagatgctc cagtgcttgg cagtcctgag aaggaagagg cagcctcaga  1440
gccaccagct gctgctcctg atgctgcacc accacccct gataggccca ttgagaagaa  1500
atcctattcc cgggcaagaa gaactcgaac caaagtttgga gatgcagtca agcttgcaga  1560
ggaggtgccc cctcctcctg aaggactgat tccagcacct ccagtcccag aaaccacccc   1620
aactccacct actaagactg ggaccgggaa agctccggtg gattctagta caagtggact  1680
tgagcaagat gtggcacaac taaatatagc agaacagaat tggagtccgg gcagccttc   1740
tttcctgcaa ccacgggaac ttcgaggtat gcccaaccat atacacatgg gagcaggacc  1800
tccacctcag tttaaccgga tggaagaaat gggtgtccag ggtggtcgag ccaaacgcta  1860
ttcatccgca cggcaaagac ctgtgccaga gccccccgcc cctccagtgc atatcagtat  1920
catggaggga cattactatg atccactgca gttccaggga ccaatctata cccatggtga  1980
cagccctgcc ccgctgcctc cacagggcat gcttgtgcag ccaggaatga accttcccca  2040
cccaggttta catccccacc agacaccagc tcctctgccc aatccaggcc tctatccccc  2100
accagtgtcc atgtctccag acagccacc acctcagcag ttgcttgctc ctacttactt  2160
ttctgctcca ggcgtcatga actttggtaa tcccagttac ccttatgctc cagggggcact  2220
```

```
gcctccccca ccaccgcctc atctgtatcc taatacacag gccccatcac aggtatatgg  2280
aggagtgacc tactataacc ccgcccagca gcaggtgcag ccaaagccct ccccacccccg  2340
gaggactccc cagccagtca ccatcaagcc cctccacct  gaggttgtaa gcagggttc   2400
cagtaatac  aagtttctga atattttaaa tcttaacatc atataaaaag cagcagaggt  2460
gagaactcag aagagaaata cagctggcta tctactacca gaagggcttc aaagatatag  2520
ggtgtggctc ctaccagcaa acagctgaaa gaggaggacc cctgccttcc tctgaggaca  2580
ggctctagag agaggagaa  acaagtggac ctcgtcccat cttcactctt cacttgagtt  2640
ggctgtgttc gggggagcag agagagccag acagccccaa gcttctgagt ctagatacag  2700
aagcccatgt cttctgctgt tcttcacttc tgggaaattg aagtgtcttc tgttcccaag  2760
gaagctcctt cctgtttgtt ttgttttcta agatgttcat tttaaagcc  tggcttctta   2820
tccttaatat tattttaatt ttttctcttt gtttctgttt cttgctctct ctccctgcct  2880
ttaaatgaaa caagtctagt cttctggttt tctagcccct ctggattccc tttgactct    2940
tccgtgcatc ccagataatg gagaatgtat cagccagcct tccccaccaa gtctaaaaag  3000
acctggcctt tcacttttag ttggcatttg ttatcctcct gtatacttgt attcccttaa  3060
ctctaaccct gtggaagcat ggctgtctgc acagaggggtc ccattgtgca gaaaagctca  3120
gagtaggtgg gtaggagccc ttctctttga cttaggtttt taggagtctg agcatccatc  3180
aatacctgta ctatgatggg cttctgttct ctgctgaggg ccaataccct actgtgggga  3240
gagatggcac accagatgct tttgtgagaa agggatggtg gagtgagagc ctttgccttt  3300
aggggtgtgt attcacatag tcctcagggc tcagtctttt gaggtaagtg gaattagagg  3360
gccttgcttc tcttctttcc attcttcttg ctacacccct tttccagttg ctgtggacca  3420
atgcatctct ttaaaggcaa atattatcca gcaagcagtc taccctgtcc tttgcaattg  3480
ctcttctcca cgtctcttcct gctacaagtg ttttagatgt tactaccta  ttttccccga  3540
attctatttt tgtccttgca gacagaatat aaaaactcct gggcttaagg cctaaggaag  3600
ccagtcacct tctgggcaag ggctccatc  tttcctcct  atccatgca  ctaaaccact   3660
tctctgctgc ctctgtggaa gagattccta ttactgcagt acatacgtct gccagggta   3720
acctggccac tgtccctgtc cttctacaga acctgagggc aaagatggtg gctgtgtctc  3780
tccccggtaa tgtcactgtt tttattcctt ccatctagca gctggcctaa tcactctgag  3840
tcacaggtgt gggatggaga gtggggagag gcacttaatc tgtaacccc  aaggaggaaa   3900
taactaagag attcttctag gggtagctgg tggttgtgcc ttttgtaggc tgttcccttt  3960
gccttaaacc tgaagatgtc tcctcaagcc tgtgggcagc atgcccagat tcccagacct  4020
taagacactg tgagagttgt tctcgttggt ccactgtgtt tagttgcaag gattttttcca  4080
tgtgtggtgg tgtttttttgt tactgtttta aagggtgccc atttgtgatc agcattgtga  4140
cttggagata ataaaattta gactataaac ttggctccct aaaaaaaaaa aaaaaaa      4198

SEQ ID NO: 30           moltype = DNA   length = 3287
FEATURE                 Location/Qualifiers
source                  1..3287
                        mol_type = genomic DNA
                        organism = Homo sapiens
SEQUENCE: 30
gacaggagga aacgcagcgc cagcagcatc tcatctaccc tccttgacac ctccccgtgg  60
ctccagccaa accctagagg tcagccttgc ggaccaacag gaggactccc agctttccct   120
tttcaagagg tccccagaca ccggccaccc tcttccagcc cctgcggcca gtgcaaggag  180
gcaccaatgc tctgaggctg tcgcgtggtg cagcgtcgag catcctcgcc gaggtccttt  240
ctgctgcctg tcccgcctca ccccgctcca tcacaccagc tggccctctt tgcttccttt  300
tcccagaatc gttaagcccc gactccact agcacctcgt accaacctcg ccccacccca  360
tcctcctgcc ttcccgcgct ccggtgtccc ccgctgccat gagctcccc  atcagcaaga   420
gccgctcgct tgccgccttc ctgcagcagc tgcgcagtcc gaggcagccc ccgagactgc  480
tgacatctac ggcgtacacg tcccctcagc cgcgagaggt gccagtctgc ccgctgacag  540
ctggtggcga gactcagaac gcggccgccc tgccgggccc caccagctgg ccactgctgg  600
gcagcctgct gcagattctc tggaaaggg  gtctcaagaa acagcacgac accctggtgg  660
agtaccacaa gaagtatggc aagatttcc  gcatgaagtt gggttccttt gagtcggtgc  720
acctgggctc gccatgcctg ctgaagcgc  tgtaccgcac cgagagcgcg tacccgcagc  780
ggctggagat caaaccgtgg aaggcctatc gcgactaccg caaagaaggc tacgggctgc  840
tgatcctgga aggggaagac tggcagccgg tccggagtgc ctttcaaaag aaactaatga  900
aaccaggga  agtgatgaag ctggacaaca aaatcaatga ggtcttggcc gattttatgt  960
gcagaataga tgagctctgt gatgaaagag gccacgttga agacttgtac agcgaactga  1020
acaaatggtc gtttgaaagt atctgcctcg tgttgtatga gaagagattt gggcttctcc  1080
agaagaatgc aggggatgaa gctgtgaact tcatcatggc catcaaaaca atgatgagca  1140
cgtttgggag gatgatggtc actccagtcg agctgcacaa gagcctcaac accaaggtct  1200
ggcaggacca cactctggcc tgggacacca ttttcaaatc agtcaaagct tgtatcgaca  1260
accggttaga gaagtattct cagcagccta gtgcagattt cctttgtgac atttatcacc  1320
agaatcggct ttcaaagaaa gaattgtatg ctgctgtcac agagctccag ctggctgcgg  1380
tggaaacgac agcaaacagt ctaatgtgga ttctctacaa tttatcccgt aatccccaag  1440
tgcaacaaaa gcttcttaag gaaattcaaa gtgtattacc tgagaatcag gtgccacggg  1500
cagaagattt gaggaatatg ccgtatttaa aagcctgtct gaaagaatct atgaggctta  1560
cgccgagtgt accatttaca actcggactc ttgacaaggc aacagttctg ggtgaatatg  1620
ctttacccaa aggaacagtg ctcatgctaa atacccaggt gttgggatcc agtgaagaca  1680
attttgaaga ttcaagtgg  tttagacctg aacgttagtc tcaggagaag gaaaaaatta  1740
atccttttgc gcatcttcca tttggcgttg gaaaagaat  gtgcattggt cgccgattag  1800
cagagcttca actgcatttg gctctttgtt ggattgtccg caaatacgac atccaggcca  1860
cagacaatga gcctgttgag atgctacact caggcaccct ggtgcccagc cgggaactcc  1920
ccatcgcgtt tgccagcga  taatacgcct cagatgtgtg tatttgctaa catcatatcc  1980
aactcaagga agcgactga  gtgctgggat ccaaggcatt ctacaggtt  cactgctggt   2040
ttacacttca cctgtgtcag caccatcttc aggtgcttag aatggcctgg gagcctgttc  2100
tgtcttgcat cttccatgac atgaaaggga ggctggcact tgtcagtcag gtagaggtta  2160
caaaccgttt caggccctgc ctaccacatt cactgtttga atctttaatt cccaagaata  2220
agtttacatt tcacaatgaa tgacctacaa cagctaaatt ttctggggct gggagtaata  2280
ctgacaatcc atttactgta gctctgctta atgtactact taggaaaatg tccctgctta  2340
```

-continued

```
ataatgtaag ccaagctaaa tgatggttaa agttatcagg cctcccatga aattgcgttc    2400
ttcctgcatt gaaataaaaa cattattggg aaactagaga acacctctat ttttaaaagg    2460
actttaacga agtcaaacaa cttataagac tagtgattca ctggggcatt attttgttag    2520
aggaccttaa aattgtttat tttttaaatg tgattccttt atggcattag ggtaaagatg    2580
aagcaataat ttttaaattg tgtatgtgca tatgaagcac agacatgcat gtgtgtgtgt    2640
gtctgtgtgt gtgtgtccgt gtatgtgtgt gtgggttcta atggtaattt gcctcagtca    2700
tttttttaat atttgcagta cttgatttag gatctgtggt gcagggcaat gtttcaaagt    2760
ttagtcacag cttaaaaaca ttcagtgtga ctttaatatt ataaaatgat ttcccatgcc    2820
ataattttc tgtctattaa atgggacaag tgtaaagcat gcaaaagtta gagatctgtt    2880
atataacatt tgttttgtga tttgaactcc taggaaaaat atgatttcat aaatgtaaaa    2940
tgcacagaaa tgcatgcaat acttataaga cttaaaaatt gtgtttacag atggtttatt    3000
tgtgcatatt tttactactg cttttcctaa atgcatactg tatataattc tgtgtatttg    3060
ataaatattt cttcctacat tatatttta gaatatttca gaaatataca tttatgtctt    3120
tatattgtaa taaatatgta catatctagg tatatgcttt ctctctgctg tgaaattatt    3180
tttagaatta taaattcacg tcttgtcaga tttcatctgt ataccttcaa attctctgaa    3240
agtaaaaata aaagttttta aatattaaaa aaaaaaaaaa aaaaaaa                  3287

SEQ ID NO: 31          moltype = DNA   length = 3829
FEATURE                Location/Qualifiers
source                 1..3829
                       mol_type = genomic DNA
                       organism = Homo sapiens
SEQUENCE: 31
aggaaatatc ccatggctga ctgtgccaag gaggtgtctg agccagccct cccggcccga      60
gggcagggca ggtggccctg agagataagc aatcccgca gctgcagatg aggagttctg     120
agaagcattg ctcaggacag cggtaaatca ctttcttggg gtgccctgca cgccggtcct     180
gggagcaggc ggcctcccgg gggtgcggga gccccactcc tccgtggtgt gttccatttg     240
cttcccacat ctggaggagc tgacgtgcca gcctccccca gcaccaccca gggacgggag     300
gcatgagccg tcaaggcac ctgggcaaaa tccggaagcg tctggaagat gtcaagagcc     360
agtgggtccg gccagccagg gctgacttta gtgacaacga gagtgcccgg ctggccacgg     420
acgccctctt ggatgggggt tctgaagcct actggcgggt gctcagccag gaaggcgagg     480
tggacttctt gtcctcggtg gaggcccagt acatccaggc ccaggccagg gagccccgt     540
gtcccccaga caccctggga ggggcggaag caggccctaa gggactggac tccagctccc     600
tacagtccgg caccctcttc cctgtggcct cagagggcag cgagccggcc ctactgcaca     660
gctgggcctc agctgagaag ccctacctga aggaaaaatc cagcgccact gtgtacttcc     720
agaccgtcaa gcacaacaac atcagagacc tcgtccgccg ctgcatcacc cggactagcc     780
agaacatttc catccggagt gtggaaggag agatatactg tgccaagtca ggcaggaaat     840
tcgctggcca aatccgggag aagttcatca tctcggactg gagatttgtc ctgtctggat     900
cttacagctt cacctggctc tgcggacacg tgcaccggaa catcctctcc aagttcacag     960
gccaggcggt ggagctgttt gacgaggagt tccgccacct ctacgcctcc tccaagcctg    1020
tgatgggcct gaagtccccg cggctggtcg ccccccgtcc gccggagca gccccggcca    1080
atggccgcct tagcagcagc agtggctccg ccagtgaccg cacgtcctcc aacccttca     1140
gcggccgctc ggcaggcagc caccccggta cccgaagtgt gtccgcgtct tcagggccct    1200
gtagccccgc ggcccacac ccgcctccac cgccccggtt ccagcccac caaggccctt     1260
ggggagcccc gagtccccag gcccacctct ccccgcggcc ccacgacggc ccgcccgccg    1320
ctgtctacag caacctgggg gcctacaggc ccacgcggct gcagctggag cagctgggcc    1380
tggtgccgag gctgactcca acctggaggc ccttcctgcg ggcctcccct ccacttctgaa    1440
ggtcccatcc cctgctgccc tccgcaggcc cagggctggg cactccctga acccaaaga    1500
cccacctcaa cgacgagtgg cgttgagcca cttccctttg aaaagacact caaaatcact    1560
gccatggttc aatgttccca ggccccaggc catccacttg ccggccccca ccagttcttg    1620
ggttcccgc tctagtttga cctgtgcagc acattccaga aggttccagg gaggttgtgg    1680
ggcagctaga ggacaaaatc atgaaaacag agtccctgtc ttccagagat catccgggc    1740
tttaatatta atgccccca aaactccgta agaagcagga aatgcagccc aagttttaca    1800
aatgggtaaa cagaggcact gagagataga tggtagttg gtacttctgg ttcccagtgc    1860
ccaggaatgg tccactccca agaaattcag gaaagaagaa ctgagggaga ggtgtgggaa    1920
cattctggat gtttcgggag agttgggaa actcctcctc ttaggaaagg ctaatactag    1980
ggtatccttg gcccaatga attagggtg aggcccaga acccgttatc tatgagttgt     2040
atggggagc catctgaagc tgtagccacc agggatgcag ctagctgagg agtttggggt    2100
gttgggttgg acaaggcagg ttagtagact cagattcttg cttcaaagag ccttgggctg    2160
gcctggaggt ccctggagtc tagactggac ctaggagct gagttgtcag gggccaggac    2220
tggccccact gcagtgccca ggccagtctt gagcagcagg gagggctcag ctgtccccag    2280
atccaggtgc ctctgaccag cctggtcacc tctgaggaa taaatgctga acctcacaag    2340
ccccatcatt catttcttct caattcacag tgcccctctt tgtttctggg gtggaactag    2400
gtcctgaggg cacagcctag ctgagtgcaa agaaatatag gatgcttaga aagcatacag    2460
gaggggccag gcgtggtggc tcatgcctgt aatcccagaa ctttgggatg ccaaggtggt    2520
tggattacct gagatcaggt ggattacctg gtctcgagac cagcctgacc aatatggtga    2580
aaccccgtct ctactaaaaa tacaaaaatt aggctgagac aggagaattg cttgaaccca    2640
ggaagcagag gttgcaatga gctgagattg catcactgca ctccagcatg gcaacaaag    2700
caagactccg tcacagaaaa aaaaaaaaa aagagagaga gcataagaga gggttggcca    2760
gccctgtggt gggtgggatg tcagagacac ttcccagata aagtaagagt taaccctgca    2820
cctcaggtgt gatagtgggg tcagtggtat gtgatccagg ctggggagcc agaggggagc    2880
aggtgccaac tccacatcct tctcctgttt ctaggccctc tcctcccttg tcggtttttg    2940
gcggggaagc tcagccttcg ctgtggaggg acgagagcac agagctcttc ctcctggtgg    3000
cctctgaccc ctgacggcct gtggcatcct ccctagtcct ctctgcccat ccatcctgtg    3060
gttcaaattc tccactgctc ccagcatgat ctgggcatc ttgcttctg gtttctttta    3120
ttattattat tattattaat tattgtattc ctgtccttca ctttttttcct ccttagttcc    3180
tgaaagtaaa caaaacaaaa caaaaacaaa aaacaaaca acactttggt tcctgatggc    3240
tttctgaacc cagccctgac cttgttgttt cacagctgac ggctgagatg aggttagaat    3300
gactgggccc ggctgaacat tccaaattgg atttcaccat ctgctgagaa agtttaagga    3360
```

```
aggcaaagct tgccaggtca cagaagctcc caagcccagc tttccaaagg cctcagcctg   3420
tgcctgtgtc gagctcagtc ctggagata ggggagaacc tgcaggcagg aacaagcccc    3480
cctactcctg accaccctcc atcagcagtc tcccctccgt ggtcgtcttt gttgacaaag   3540
gtgcagtttc tcctctcctg ggcacctgta acatgtgatg cgctgcctgc tgggaggtta   3600
ggtcgggct gccccggcga gtggagcatg agcagaaccg ccgagggtca cttctgggca    3660
gaagctttga gagcctgggt ccaggttgcc acatagaagc agctctccag ttgaaaccct   3720
cctctgccag cctggggtcc taagcgatga gcagaatccc ccactcccac cccaccaacc   3780
cacaatggat atgtagtgag caagaaataa acctttgttg tttaagcca               3829

SEQ ID NO: 32           moltype = DNA  length = 585
FEATURE                 Location/Qualifiers
source                  1..585
                        mol_type = genomic DNA
                        organism = Homo sapiens
SEQUENCE: 32
gttcactggg cgtcttctgc ccggccctt cgcccacgtg aagaacgcca gggagctgtg     60
aggcagtgct gtgtggttcc tgccgtccgg actctttttc ctctactgag attcatctgt   120
gtgaaatatg agttggcgag gaagatcgac ctattattgg cctagaccaa ggcgctatgt   180
acagcctcct gaaatgattg ggcctatgcg gcccgagcag ttcagtgatg aagtggaacc   240
agcaacacct gaagaagggg aaccagcaac tcaatgtcag gatcctgcag ctgctcagga   300
gggagaggat gagggagcat ctgcaggtca agggccgaag cctgaagctc atagccagga   360
acagggtcac ccacagactg ggtgtgagtg tgaagatggt cctgatgggc aggagatgga   420
cccgccaaat ccagaggagg tgaaaacgcc tgaagaaggt gaaaagcaat cacagtgtta   480
aaagaagaca cgttgaaatg atgcaggctg ctccctatgt tggaaatttgt tcattaaaat  540
tctcccaata aagctttaca gccttctgca aagaagtctt gcgca                   585

SEQ ID NO: 33           moltype = DNA  length = 1780
FEATURE                 Location/Qualifiers
source                  1..1780
                        mol_type = genomic DNA
                        organism = Homo sapiens
SEQUENCE: 33
gcagagctac catgtcctct tggagcagac agcgaccaaa aagcccaggg ggcattcaac    60
cccatgtttc tagaactctg ttcctgctgc tgctgttggc agcctcagtc tgggggtca   120
ccctgagccc caaagactgc caggtgttcc gctcagacca tggcagctcc atctcctgtc   180
aaccacctgc cgaaatcccc ggctacctgc cagccgacac cgtgcacctg gccgtggaat   240
tcttcaacct gacccacctg ccagccaacc tcctccaggg cgcctctaag ctccaagaat   300
tgcacctctc cagcaatggg ctggaaagcc ctcgcccga attcctgcgg ccagtgccgc   360
agctgagggt gctggatcta acccgaaacg ccctgaccgg gctgccccg ggcctcttcc   420
aggcctcagc caccctggac accctggtat tgaaagaaaa ccagctggag gtcctggagg   480
tctcgtggct acacggcctg aaagctctgg ggcatctgga cctgtctggg aaccgcctcc   540
ggaaactgcc ccccggctg ctggccaact tcaccctcct gcgcaccctt gaccttgggg   600
agaaccagtt ggagaccttg ccacctgacc tcctgagggg tccgctgaa ttagaacggc   660
tacatctaga aggcaacaaa ttgcaagtac tgggaaaaga tctcctcttg ccgcagccgg   720
acctgcgcta cctcttcctg aacggcaaca gctggccag ggtggcagcc ggtgccttcc   780
agggcctgcg gcagctggac atgctggacc tctccaataa ctcactggcc agcgtgcccg   840
aggggtctg ggcatcccta gggcagccaa actgggacat gcggatggc ttcgacatct   900
ccggcaaccc ctggatctgt gaccagaacc tgagcgacct ctatcgttgg cttcaggccc   960
aaaaagacaa gatgtttccc cagaatgaca cgcgctgtgc tgggcctgaa gccgtgaagg  1020
gccagacgct cctggcagtg gccaagtccc agtgagacca ggggcttggg ttgagggtgg  1080
ggggtctggt agaacactgc aacccgctta acaaataatc ctgcctttgg ccgggtgctgg  1140
gggctcacgc ctgtaatccc agcactttgg gaggcccagg tggcggatc acgaggtcag   1200
gagatcgaga ccatcttggc taacatggtg aaacccgtc tctactaaaa atataaaaaa   1260
ttagccaggc gtggtggtgg gcacctgtag tcccagcaac tcgggaggct gaggcaggag   1320
aatgcgtga acttgggagg cggagcttgc ggtgagccaa gatcgtgcca ctgcactcta   1380
gcctgggcga cagagcaaga ctgtctcaaa aaaattaaaa ttaaaattaa aaacaaataa   1440
tcctgccttt tacaggtgaa actcggggct gtccatagcg gctgggaccc cgtttcatcc   1500
atccatgctt cctagaacac acgatgggct ttccttaccc atgcccaagg tgtgccctcc   1560
gtctggaatg ccgttccctg tttcccagat ctcttgaact ctgggttctc ccagcccctt   1620
gtccttcctt ccagctgagc cctggccaca ctggggctgc ctttctctga ctctgtcttc   1680
cccaagtcag ggggctctct gagtgcaggg tctgatgctg agtcccactt agcttgggt   1740
cagaaccaag ggggtttaata aataacccctt gaaaactgga                      1780

SEQ ID NO: 34           moltype = DNA  length = 1724
FEATURE                 Location/Qualifiers
source                  1..1724
                        mol_type = genomic DNA
                        organism = Homo sapiens
SEQUENCE: 34
agagacaagc gagcttctgc gtctgactcg cagcttgaga ctggcggagg gaagcccgcc    60
caggctctat aaggagacaa ggttctgagc agacaggcca accggaggac aggattccct   120
ggaggccaca gaggagcacc aaggagaaga tctgcctgtg ggtccccatt gcccagcttt   180
tgcctgcact cttgcctgct gccctgacca gagtcatcat gtcttctgag cagaagagtc   240
agcactgcaa gcctgaggaa ggcgttgagg cccaagaaga ggcgtggggc ctggtgggtg   300
cacaggctcc tactactgag gagcaggagg ctgctgtctc ctcctcctct cctctggtcc   360
ctggcaccct ggaggaagtg cctgctgctg agtcagcagg tcctcccag agtcctcagg   420
gagcctctgc cttacccact accatcagct tcacttgctg gaggcaaccc aatgagggtt   480
ccagcagcca agaagaggag gggccaagca cctcgcctga cgcagagtcc ttgttccgag   540
aagcactcag taacaaggtg gatgagttgg ctcattttct gctccgcaag tatcgagcca   600
```

-continued

```
aggagctggt cacaaaggca gaaatgctgg agagagtcat caaaaattac aagcgctgct   660
ttcctgtgat cttcggcaaa gcctccgagt ccctgaagat gatctttggc attgacgtga   720
aggaagtgga ccccgccagc aacacctaca cccttgtcac ctgcctgggc ctttcctatg   780
atggcctgct gggtaataat cagatctttc caagacaggc cttctgata atcgtcctgg    840
gcacaattgc aatggagggc gacagcgcct ctgaggagga aatctgggag gagctgggtg   900
tgatgggggt gtatgatggg agggagcaca ctgtctatgg ggagcccagg aaactgctca   960
cccaagattg ggtgcaggaa aactacctgg agtaccggca ggtacccggc agtaatcctg  1020
cgcgctatga gttcctgtgg ggtccaaggg ctctggctga aaccagctat gtgaaagtcc  1080
tggagcatgt ggtcagggtc aatgcaagag ttcgcattgc ctacccatcc ctgcgtgaag  1140
cagctttgtt agaggaggaa gaggagtcct gagcatgagt tgcagccagg gctgtgggga  1200
aggggcaggg ctgggccagt gcatctaaca gccctgtgca gcagcttccc ttgcctcgtg  1260
taacatgagg cccattcttc actctgtttg aagaaaatag tcagtgttct tagtagtggg  1320
tttctatttt gttggatgac ttggagattt atctctgttt ccttttacaa ttgttgaaat  1380
gttcctttta atggatggtt gaattaactt cagcatccaa gtttatgaat cgtagttaac  1440
gtatattgct gttaatatag tttaggagta agagtcttgt ttttttattca gattgggaaa  1500
tccgttctat tttgtgaatt tgggacataa taacagcagt ggagtaagta tttagaaagtg  1560
tgaattcacc gtgaaatagg tgagataaat taaaagatac ttaattcccg ccttatgcct  1620
cagtctattc tgtaaaattt aaaaaatata tatgcatacc tggatttcct tggcttcgtg  1680
aatgtaagag aaattaaatc tgaataaata attcttctg ttaa                     1724

SEQ ID NO: 35          moltype = DNA  length = 3681
FEATURE                Location/Qualifiers
source                 1..3681
                       mol_type = genomic DNA
                       organism = Homo sapiens
SEQUENCE: 35
tgtaaatgct cttctgacta atgcaaacca tgtgtccata gaaccagaag attttttccag    60
ggaaaagag ccccacgcc ccgcccagct ataaggggcc atgcaccaag cagggtaccc     120
aggctgcaga ggtgccatgg ctgagtcaca cctgctgcag tggctgctgc tgctgctgcc   180
cacgctctgt ggcccaggca ctgctgcctg gaccaccta tccttggcct gtgcccaggg   240
ccctgagttc tggtgccaaa gcctggagca agcattgcag tgcagagccc tagggcattg   300
cctacaggaa gtctgggac atgtgggagc cgatgaccta tgccaagagt gtgaggacat   360
cgtccacatc cttaacaaga tggccaagga ggccattttc caggacacga tgaggaagtt   420
cctggagcga gagtgcaacg tcctccccctt gaagctgcc atgcccccagt gcaaccaagt   480
gcttgacgac tacttccccc tggtcatcga ctacttccag aaccagactg actcaaacgg   540
catctgtatg cacctgggcc tgtgcaaatc ccggcagcca gagccagagc aggagccagg   600
gatgtcagac ccccctgccca aacctctgcg ggaccctctg ccagaccctc tgctggacaa   660
gctcgtcctc cctgtgctgc ccggggccct ccaggcgagg cctgggcctc acacacagga   720
tctctccgag cagcaattcc ccattcctct cccctattgc tggctctgca gggctctgat   780
caagcggatc caagccatga ttcccaaggg tgcgctagct gtggcagtgg cccaggtgtg   840
ccgcgtggta cctctggtgg cgggcggcat ctgccagtgc ctggctgagc gctactccgt   900
catcctgctc gacacgctgc tgggccgcat gctgccccag ctggtctgcc gcctcgtcct   960
ccggtgctcc atggatgaca gcgctggccc aagtcgcca acaggagaat ggctgccgcg  1020
agactctgag tgccacctct gcatgtccgt gaccacccag gccggaaca gcagcgagca  1080
ggccatacca caggcaatgc tccaggcctg tgttggctcc tggctggaca gggaaaagtg  1140
caagcaattt gtggagcagc acacgcccca gctgctgacc ctggtgccca ggggctggga  1200
tgcccacacc acctgccagg ccctcggggt gtgtgggaac atgtccagcc ctctccagtg  1260
tatccacagc cccgacctt gatgagaact cagctgtcca gctgcaaagg aaaagccaag  1320
tgagacgggc tctgggacca tggtgaccag gctcttcccc tgctccctgg ccctcgccag  1380
ctgccaggct gaaaagaagc ctcagctccc acccgccct cctcaccgcc cttcctcggc  1440
agtcacttcc actggtggac cacgggcccc cagccctgtg tggccttgt ctgtctgagg  1500
tcaaccacag tctgacacca gagcccactt ccatcctctc tggtgtgagg cacagcgagg  1560
gcagcatctg gaggagctct gcagcctcca cacctaccac gacctccag ggctgggctc   1620
aggaaaaacc agccactgct ttacaggaca gggggttgaa gctgagcccc gcctcacacc  1680
caccccatg cactcaaaga ttggattta cagctacttg caattcaaaa ttcagaagaa   1740
taaaaaatgg gaacatacag aactctaaaa gatagacatc agaaattgtt aagttaagct  1800
ttttcaaaaa atcagcaatt cccagcgta gtcaagggtg gacactgcac gctctggcat  1860
gatgggatgg cgaccgggca gcttttcttc ctcgagatgc tctgctgctt gagagctatt  1920
gctttgttaa gatataaaaa ggggtttctt ttttgctttc tgtaaggtgg acttccagct  1980
tttgattgaa agtcctaggg tgattctatt tctgctgtga tttatctgct gaaagctcag  2040
ctgggggttgt gcaagctagg gacccattcc tgtgtaatac aatgtctgca ccaatgctaa  2100
taaagtccta ttctcttta tgagaaagaa aaagacaccg tccttaaag tgctgcagta  2160
tggccagacg tggtggctca cacctgcaat cccagcacct aggaggccg aggcaggagg  2220
atccttgagg tcaggagttc gagaccagcc tcgccaacat ggtgaaaccc catttcgtt  2280
aaaaatacaa aaaattagcc aagtgtggtg gcatatgcct gtaatcccaa ctactcagaa  2340
ggccgaggca ggagaattac ttgaacgcag gagaatcact gcagcccagg aggcagaggt  2400
tgcagtgagc cgagattgca ccactgcact ccagcctggg tgacagagca agactccatc  2460
tcagtaaata aataaataaa taaaaagcgc tgcagtagct gtggcctcac cctgaagtca  2520
gcgggcccag gcctacctca ctctctccct tggcagagaa gcagacgtcc atagctcctc  2580
tccctcacaa gcgctcccag cctgcctcc agctgctgct ctccctccc agtctctact  2640
cactgggatg aggttaggtc atgaggacac caaaaaccta aaaataaaca aaagccaaa  2700
caagcctag ctttcttaa agactgaaat gcctggaagt gtcccttat ttataaaata   2760
actttgtca tatttcttat acatgttcct tgtaagaaat tcagaaacta cagacaaaga  2820
gagtgaaat tacccactgt caggcctctg agccaagcat accatcat atccccatgg  2880
ccctgcacgt atacccccag atggcctgaa gcaactgaag atccacaaaa gaagtgaaaa  2940
tagccagttc ctgccttaac tgatgacatt ccaccattgt gatttgttcc tgccccaccc  3000
taactgatca attgaccttg tgacaataca ccttccccac ccttgagaag gtgctttgta  3060
atattctccc cacccacccc acgcccgcac cccgcacccc ttaagaaggt attttgtaat  3120
attctctccg ccattgagaa tgtgctttgt aagatccacc ccctgccac aaaaaattgc  3180
```

```
tcctaactcc accgcctatc ccaaacctac aagaactaat gataatccca ccacccttg    3240
ctgactcttt ttggactcag cccacctgca cccaggtgat taaaaagctt tattgttcac    3300
acaaagcctg tttggtagtc tcttcacagg gaagcatgtg acacccacaa tcccacctag    3360
cccaggagag agctacggca gggtgtgtgt tttgacactg agcttggggc tttttccatc    3420
ttctccccac agcctctggc tccacacctc caccgttcaa cgccagaaa gagctgtcta    3480
tgcagcctgc tcttgggcct ggggatgaga cacacaattc attggctcct ggatttaag    3540
tagacatttg taaatctata gctaactact gtccttaaag ccattgtttc cattacaaaa    3600
tccaactctc tgagagaaaa gggtgtttta aatttaaaaa aataaaaaca aaaagtttg    3660
attgagaaaa aaaaaaaaaa a                                              3681

SEQ ID NO: 36         moltype = DNA   length = 481
FEATURE               Location/Qualifiers
source                1..481
                      mol_type = genomic DNA
                      organism = Homo sapiens
SEQUENCE: 36
gggaacgcgg cggagctgtg agccggcgac tcgggtccct gaggtctgga ttctttctcc    60
gctactgaga cacggcggac acacacaaac acagaaccac acagccagtc ccaggagccc    120
agtaatggag agcccccaaaa agaagaacca gcagctgaaa gtcgggatcc tacacctggg   180
cagcagacag aagaagatca ggatacagct gagatcccag gtgctgggaa gggaaatgcg    240
cgacatggaa ggtgatctgc aagagctgca tcagtcaaac accggggata aatctggatt    300
tgggttccgg cgtcaaggtg aagataatac ctaaagagga acactgtaaa atgccagaag    360
caggtgaaga gcaaccacaa gtttaaatga agacaagctg aaacaacgca agctggtttt    420
atattagata tttgacttaa actatctcaa taaagttttg cagctttcac caaaaaaaaa    480
a                                                                    481
```

DETECTION OF LUNG NEOPLASIA BY AMPLIFICATION OF RNA SEQUENCES

CROSS REFERENCE TO RELATED APPLICATIONS

The present invention is a continuation of U.S. patent application Ser. No. 17/078,924, filed Oct. 23, 2020, now allowed, which is a continuation of U.S. patent application Ser. No. 15/587,806, filed May 5, 2017, now abandoned, which claims priority benefit of U.S. Provisional Patent Application No. 62/332,419, filed May 5, 2016, each of which is incorporated by reference in its entirety.

SEQUENCE LISTING

The text of the computer readable sequence listing filed herewith, titled "34787-304_SEQUENCE_LISTING", created Sep. 15, 2022, having a file size of 54,939 bytes, is hereby incorporated by reference in its entirety.

FIELD OF THE INVENTION

Provided herein is technology relating to detecting neoplasia and particularly, but not exclusively, to methods, compositions, and related uses for detecting neoplasms such as lung cancer.

BACKGROUND OF THE INVENTION

Lung cancer is the most frequent cause of death among men and women younger than 85 years in the US. It accounts for 27% of all cancer deaths and 221,000 lost lives annually. This mortality rate exceeds that of the next 4 highest ranking cancers combined. Gene expression profiling has confirmed unique mRNA expression in cancers and can be used as an approach for detection of lung malignancies. An mRNA multi-marker approach to detect all subtypes of lung cancer needs to be explored. This study assesses the value of measuring expression levels of multiple mRNA markers in detecting lung cancer of different subtypes.

SUMMARY OF THE INVENTION

This technology is in the field of nucleic acid detection and quantification. Specifically, the technology addresses the detection and quantification of RNA in samples using single-tube RT-PCR-Invasive cleavage reaction (RT-QuARTS).

In some embodiments the technology provides methods of screening for a lung neoplasm in a sample obtained from a subject, the methods comprising, e.g., a) assaying a sample from a subject for an amount of at least one RNA marker selected from the group consisting of GAGE12D, FAM83A, LRG1, XAGE-1 d, MAGEA4, SFTPB, AKAP4, and CYP24A1; b) assaying the sample for an amount of a reference marker in the sample; c) comparing the amount of the at least one RNA marker to the amount of the reference marker to determine a level of expression for the at least one marker gene in the sample; and d) generating a record reporting the expression for the at least one marker gene in said sample. In some embodiments the method comprises obtaining a sample comprising RNA from a subject and treating the RNA with a reverse transcriptase, preferably MMLV reverse transcriptase, to form a cDNA copy of at least a portion of the RNA. In preferred embodiments, the cDNA is created and detected in a single vessel, without opening the vessel, e.g., to add additional reagents.

In some embodiments the at least one RNA marker is at least two markers. In some preferred embodiments the at least one RNA marker comprises the group consisting of GAGE, FAM83A, LRG1 and MAGEA4 markers, while in some embodiments, the at least one RNA marker comprises the group consisting of GAGE, FAM83A, LRG1, CYP24A1, XAGE1D and MAGEA4 markers. In some embodiments, the reference marker is an RNA, preferably an RNA selected from the group consisting of CASC3 mRNA, β-actin mRNA, U1 snRNA and U6 snRNA.

In some embodiments the technology comprises assaying RNA using one or more of a polymerase chain reaction, nucleic acid sequencing, mass spectrometry, mass-based separation, or target capture. In particularly preferred embodiments, the assaying comprises using a flap endonuclease assay, such as a QuARTS assay, as described hereinbelow.

In some embodiments, assaying the expression of the RNA marker comprises detecting increased or decreased expression of the RNA marker relative to a normal expression of the marker.

Samples suitable for analysis using the technology are not limited to a particular sample type. In some embodiments the sample is a tissue sample, a blood sample, a serum sample, or a sputum sample. In certain preferred embodiments the tissue sample comprises lung tissue.

The technology further provides kits, e.g., for practicing the technology. For example, in some embodiments the technology provides a kit comprising:

a) at least one oligonucleotide, wherein at least a portion of said oligonucleotide specifically hybridizes to a marker RNA selected from the group consisting of GAGE12D, FAM83A, LRG1, XAGE-1 d, MAGEA4, SFTPB, AKAP4, and CYP24A1, and b) at least one additional oligonucleotide, wherein at least a portion of said additional oligonucleotide specifically hybridizes to a reference nucleic acid.

In preferred embodiments the kit comprises at least two additional oligonucleotides. In some embodiments, the kit further comprises one or more components selected from the group consisting of reverse transcriptase, flap endonuclease, DNA polymerase, and a FRET cassette.

In some embodiments the at least one RNA marker is selected from the group consisting of GAGE, FAM83A, LRG1, CYP24A1, XAGE1D and MAGEA4, and in some embodiments the RNA marker is selected from the group consisting of GAGE, FAM83A, LRG1 and MAGEA4. In certain preferred embodiments the kit comprises at least 4 oligonucleotides, wherein each of the markers in the group consisting of GAGE, FAM83A, LRG1, and MAGEA4 specifically hybridizes to at least one of said 4 oligonucleotides. In other embodiments, the kit comprises at least 6 oligonucleotides, wherein each of the markers in the group consisting of GAGE, FAM83A, LRG1, CYP24A1, XAGE1D and MAGEA4 specifically hybridizes to at least one of said 6 oligonucleotides. In preferred embodiments at least one oligonucleotide is selected from one or more of a capture oligonucleotide, a pair of nucleic acid primers, a nucleic acid probe, and an invasive oligonucleotide.

The technology is not limited to which particular reference marker RNA is used, and many are known in the field. In preferred embodiments, the reference marker is an RNA selected from the group consisting of CASC3, β-actin, U1 and U6 RNA The technology further comprises compositions such as mixtures, e.g., reaction mixtures. In some embodiments the technology provides a mixture comprising a complex of at least one RNA marker selected from the group consisting of GAGE12D, FAM83A, LRG1, XAGE-1 d, MAGEA4, SFTPB, AKAP4, and CYP24A1 and an oligonucleotide that specifically hybridizes to the RNA marker. In preferred embodiments, the composition further comprises a complex of at least one reference marker and an oligonucleotide that specifically hybridizes to the reference RNA marker. In some embodiments the at least one RNA marker is selected from the group consisting of GAGE, FAM83A, LRG1, CYP24A1, XAGE1D and MAGEA4, while in some embodiments the least one RNA marker is selected from the group consisting of GAGE, FAM83A, LRG1 and MAGEA4. In preferred embodiments the composition comprises a reference marker that is an RNA selected from the group consisting of CASC3, β-actin, U1 RNA and U6 RNA. In particularly preferred embodiments, the oligonucleotide is selected from one or more of a capture oligonucleotide, a pair of nucleic acid primers, a nucleic acid probe, and an invasive oligonucleotide. Preferably the composition comprises a nucleic acid probe oligonucleotide comprising a reporter molecule, e.g., a fluorophore, and/or a flap sequence.

In some embodiments, the composition further comprises one or more components selected from the group consisting of reverse transcriptase, (e.g., MMLV reverse transcriptase), flap endonuclease, thermostable DNA polymerase, and a FRET cassette. In preferred embodiments, the DNA polymerase is a bacterial DNA polymerase.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

The transitional phrase "consisting essentially of" as used in claims in the present application limits the scope of a claim to the specified materials or steps "and those that do not materially affect the basic and novel characteristic(s)" of the claimed invention, as discussed in In re Herz, 537 F.2d 549, 551-52, 190 USPQ 461, 463 (CCPA 1976). For example, a composition "consisting essentially of" recited elements may contain an unrecited contaminant at a level such that, though present, the contaminant does not alter the function of the recited composition as compared to a pure composition, i.e., a composition "consisting of" the recited components.

As used herein, the "sensitivity" of a given marker (or set of markers used together) refers to the percentage of samples that report a marker value (e.g., an expression marker) above a threshold value that distinguishes between neoplastic and non-neoplastic samples. In some embodiments, a positive is defined as a histology-confirmed neoplasia that reports a marker value above a threshold value (e.g., the range associated with disease), and a false negative is defined as a histology-confirmed neoplasia that reports a marker value below the threshold value (e.g., the range associated with no disease). The value of sensitivity, therefore, reflects the probability that a measurement for a given marker obtained from a known diseased sample will be in the range of disease-associated measurements. As defined here, the clinical relevance of the calculated sensitivity value represents an estimation of the probability that a given marker would detect the presence of a clinical condition when applied to a subject with that condition.

As used herein, the "specificity" of a given marker (or set of markers used together) refers to the percentage of non-neoplastic samples that report a marker value (e.g., an expression marker) below a threshold value that distinguishes between neoplastic and non-neoplastic samples. In some embodiments, a negative is defined as a histology-confirmed non-neoplastic sample that reports a marker value below the threshold value (e.g., the range associated with no disease) and a false positive is defined as a histology-confirmed non-neoplastic sample that reports a marker value above the threshold value (e.g., the range associated with disease). The value of specificity, therefore, reflects the probability that a marker measurement for a given marker obtained from a known non-neoplastic sample will be in the range of non-disease associated measurements. As defined here, the clinical relevance of the calculated specificity value represents an estimation of the probability that a given marker would detect the absence of a clinical condition when applied to a patient without that condition.

The term "primer" refers to an oligonucleotide, whether occurring naturally as, e.g., a nucleic acid fragment from a restriction digest, or produced synthetically, that is capable of acting as a point of initiation of synthesis when placed under conditions in which synthesis of a primer extension product that is complementary to a nucleic acid template strand is induced, (e.g., in the presence of nucleotides and an inducing agent such as a DNA polymerase, and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, and the use of the method.

The term "probe" refers to an oligonucleotide (e.g., a sequence of nucleotides), whether occurring naturally as in a purified restriction digest or produced synthetically, recombinantly, or by PCR amplification, that is capable of hybridizing to another oligonucleotide of interest. A probe may be single-stranded or double-stranded. Probes are useful in the detection, identification, and isolation of particular gene sequences (e.g., a "capture probe"). It is contemplated that any probe used in the present invention may, in some embodiments, be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "target," as used herein refers to a nucleic acid sought to be sorted out from other nucleic acids, e.g., by probe binding, amplification, isolation, capture, etc. For example, when used in reference to the polymerase chain reaction, "target" refers to the region of nucleic acid bounded by the primers used for polymerase chain reaction, while when used in an assay in which target nucleic acid is not amplified, e.g., in some embodiments of an invasive cleavage assay, a target comprises the site at which a probe and invasive oligonucleotides (e.g., INVADER oligonucleotide) bind to form an invasive cleavage structure, such that the presence of the target nucleic acid can be detected. A "segment" is defined as a region of nucleic acid within the target sequence.

The term "marker", as used herein, refers to a substance (e.g., a nucleic acid, or a region of a nucleic acid, or a protein) that may be used to distinguish non-normal cells (e.g., cancer cells) from normal cells, e.g., based on presence, absence, or status (e.g., post-transcriptional processing) of the marker substance.

The term "sample" is used in its broadest sense. In one sense it can refer to an animal cell or tissue. In another sense, it refers to a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

The term "neoplasm" as used herein refers to any new and abnormal growth of tissue. Thus, a neoplasm can be a premalignant neoplasm or a malignant neoplasm.

The term "neoplasm-specific marker," as used herein, refers to any biological material or element that can be used to indicate the presence of a neoplasm. Examples of biological materials include, without limitation, nucleic acids (DNA, RNA, miRNA, etc.), polypeptides, carbohydrates, fatty acids, cellular components (e.g., cell membranes and mitochondria), and whole cells. In some instances, markers are particular nucleic acid regions (e.g., genes, intragenic regions, specific loci, etc.). Regions of nucleic acid that are markers may be referred to, e.g., as "marker genes," "marker regions," "marker sequences," "marker loci," etc.

As used herein, the terms "patient" or "subject" refer to organisms to be subject to various tests provided by the technology. The term "subject" includes animals, preferably mammals, including humans. In a preferred embodiment, the subject is a primate. In an even more preferred embodiment, the subject is a human. Further with respect to diagnostic methods, a preferred subject is a vertebrate subject. A preferred vertebrate is warm-blooded; a preferred warm-blooded vertebrate is a mammal. A preferred mammal is most preferably a human. As used herein, the term "subject' includes both human and animal subjects. Thus, veterinary therapeutic uses are provided herein. As such, the present technology provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; pinnipeds; and horses. Thus, also provided is the diagnosis and treatment of livestock, including, but not limited to, domesticated swine, ruminants, ungulates, horses (including race horses), and the like. The presently-disclosed subject matter further includes a system for diagnosing a lung cancer in a subject. The system can be provided, for example, as a commercial kit that can be used to screen for a risk of lung cancer or diagnose a lung cancer in a subject from whom a biological sample has been collected. An exemplary system provided in accordance with the present technology includes assessing the expression of a marker described herein.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810; herein incorporated by reference in its entirety) are forms of amplification. Additional types of amplification include, but are not limited to, allele-specific PCR (see, e.g., U.S. Pat. No. 5,639,611; herein incorporated by reference in its entirety), assembly PCR (see, e.g., U.S. Pat. No. 5,965,408; herein incorporated by reference in its entirety), helicase-dependent amplification (see, e.g., U.S. Pat. No. 7,662,594; herein incorporated by reference in its entirety), hot-start PCR (see, e.g., U.S. Pat. Nos. 5,773,258 and 5,338,671; each herein incorporated by reference in their entireties), intersequence-specific PCR, inverse PCR (see, e.g., Triglia, et al. (1988) Nucleic Acids Res., 16:8186; herein incorporated by reference in its entirety), ligation-mediated PCR (see, e.g., Guilfoyle, R. et al., Nucleic Acids Research, 25:1854-1858 (1997); U.S. Pat. No. 5,508,169; each of which are herein incorporated by reference in their entireties), miniprimer PCR, multiplex ligation-dependent probe amplification (see, e.g., Schouten, et al., (2002) Nucleic Acids Research 30(12): e57; herein incorporated by reference in its entirety), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80; each of which are herein incorporated by reference in their entireties), nested PCR, overlap-extension PCR (see, e.g., Higuchi, et al., (1988) Nucleic Acids Research 16(15) 7351-7367; herein incorporated by reference in its entirety), real time PCR (see, e.g., Higuchi, et al., (1992) Biotechnology 10:413-417; Higuchi, et al., (1993) Biotechnology 11:1026-1030; each of which are herein incorporated by reference in their entireties), reverse transcription PCR (see, e.g., Bustin, S. A. (2000) J. Molecular Endocrinology 25:169-193; herein incorporated by reference in its entirety), solid phase PCR, thermal asymmetric interlaced PCR, and Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478-485; each of which are herein incorporated by reference in their entireties). Polynucleotide amplification also can be accomplished using digital PCR (see, e.g., Kalinina, et al., Nucleic Acids Research. 25; 1999-2004, (1997); Vogelstein and Kinzler, Proc Natl Acad Sci USA. 96; 9236-41, (1999); International Patent Publication No. WO05023091A2; US Patent Application Publication No. 20070202525; each of which are incorporated herein by reference in their entireties).

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic or other DNA or RNA, without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" ("PCR"). Because the desired amplified segments of the target sequence become the predominant sequences (in terms of concentration) in the mixture, they are said to be "PCR amplified" and are "PCR products" or "amplicons." Those of skill in the art will understand the term "PCR" encompasses many variants of the originally described method using, e.g., real time PCR, nested PCR, reverse transcription PCR (RT-PCR), single primer and arbitrarily primed PCR, etc.

As used herein, the term "nucleic acid detection assay" refers to any method of determining the nucleotide composition of a nucleic acid of interest. Nucleic acid detection assay include but are not limited to, DNA sequencing methods, probe hybridization methods, structure specific cleavage assays (e.g., the INVADER assay, (Hologic, Inc.) and are described, e.g., in U.S. Pat. Nos. 5,846,717, 5,985, 557, 5,994,069, 6,001,567, 6,090,543, and 6,872,816, WO 2006/050499; Lyamichev et al., Nat. Biotech., 17:292 (1999), Hall et al., PNAS, USA, 97:8272 (2000), and US 2009/0253142, each of which is herein incorporated by reference in its entirety for all purposes); enzyme mismatch cleavage methods (e.g., Variagenics, U.S. Pat. Nos. 6,110, 684, 5,958,692, 5,851,770, herein incorporated by reference in their entireties); polymerase chain reaction (PCR), described above; branched hybridization methods (e.g., Chiron, U.S. Pat. Nos. 5,849,481, 5,710,264, 5,124,246, and 5,624,802, herein incorporated by reference in their entireties); rolling circle replication (e.g., U.S. Pat. Nos. 6,210, 884, 6,183,960 and 6,235,502, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110, 677, 5,914,230, 5,882,867, and 5,792,614, herein incorporated by reference in their entireties); ligase chain reaction (e.g., Baranay Proc. Natl. Acad. Sci USA 88, 189-93 (1991)); and sandwich hybridization methods (e.g., U.S. Pat. No. 5,288,609, herein incorporated by reference in its entirety).

In some embodiments, target nucleic acid is amplified (e.g., by PCR) and amplified nucleic acid is detected simultaneously using an invasive cleavage assay. Assays configured for performing a detection assay (e.g., invasive cleavage assay) in combination with an amplification assay are described in U.S. Pat. No. 9,096,893, incorporated herein by reference in its entirety for all purposes. Additional amplification plus invasive cleavage detection configurations, termed the QuARTS method, are described in U.S. Pat. Nos. 8,361,720; 8,715,937; 8,916,344; and 9,212,392, incorporated herein by reference in their entireties for all purposes. The term "invasive cleavage structure" as used herein refers to a cleavage structure comprising i) a target nucleic acid, ii) an upstream nucleic acid (e.g., an invasive or "INVADER" oligonucleotide), and iii) a downstream nucleic acid (e.g., a probe), where the upstream and downstream nucleic acids anneal to contiguous regions of the target nucleic acid, and where an overlap forms between the a 3' portion of the upstream nucleic acid and duplex formed between the downstream nucleic acid and the target nucleic acid. An overlap occurs where one or more bases from the upstream and downstream nucleic acids occupy the same position with respect to a target nucleic acid base, whether or not the overlapping base(s) of the upstream nucleic acid are complementary with the target nucleic acid, and whether or not those bases are natural bases or non-natural bases. In some embodiments, the 3' portion of the upstream nucleic acid that overlaps with the downstream duplex is a non-base chemical moiety such as an aromatic ring structure, e.g., as disclosed, for example, in U.S. Pat. No. 6,090,543, incorporated herein by reference in its entirety. In some embodiments, one or more of the nucleic acids may be attached to each other, e.g., through a covalent linkage such as nucleic acid stem-loop, or through a non-nucleic acid chemical linkage (e.g., a multi-carbon chain). As used herein, the term "flap endonuclease assay" includes "INVADER" invasive cleavage assays and QuARTS assays, as described above. The term "flap oligonucleotide" refers to an oligonucleotide cleavable in a detection assay, such as an invasive cleavage assay, by a flap endonuclease. In preferred embodiments, a flap oligonucleotide forms an invasive cleavage structure with other nucleic acids, e.g., a target nucleic acid and an invasive oligonucleotide.

As used herein, the term "PCR-invasive cleavage assay" refers to an assay in which target nucleic acid is amplified and amplified nucleic acid is detected simultaneously using a signal-amplifying invasive cleavage assay employing a FRET cassette, and in which the assay reagents comprise a mixture containing DNA polymerase, FEN-1 endonuclease, a primary probe comprising a portion complementary to a target nucleic acid, and a hairpin FRET cassette. PCR-invasive cleavage assays include the QuARTS assays described in U.S. Pat. Nos. 8,361,720; 8,715,937; 8,916, 344; and 9,212,392, and the amplification assays of U.S. Pat. No. 9,096,893, as diagrammed in FIG. 1 of that patent, each of which is incorporated herein by reference for all purposes.

As used herein, the term "PCR-invasive cleavage assay reagents" refers to one or more reagents for detecting target sequences in a PCR-invasive cleavage assay, the reagents comprising nucleic acid molecules capable of participating in amplification of a target nucleic acid and in formation of an invasive cleavage structure in the presence of the target sequence, in a mixture containing DNA polymerase, FEN-1 endonuclease and a FRET cassette, and optionally a reverse transcriptase.

As used herein, the term "FRET cassette" refers to a hairpin oligonucleotide that contains a fluorophore moiety and a nearby quencher moiety that quenches the fluorophore. Hybridization of a cleaved flap (e.g., from cleavage of a target-specific probe in a PCR-invasive cleavage assay) with a FRET cassette produces a secondary substrate for the flap endonuclease, e.g., a FEN-1 enzyme. Once this substrate is formed, the 5' fluorophore-containing base is cleaved from the cassette, thereby generating a fluorescence signal. In preferred embodiments, a FRET cassette comprises an unpaired 3' portion to which a cleavage product, e.g., a portion of a cleaved flap oligonucleotide, can hybridize to from an invasive cleavage structure cleavable by a FEN-1 endonuclease.

A nucleic acid "hairpin" as used herein refers to a region of a single-stranded nucleic acid that contains a duplex (i.e., base-paired) stem and a loop, formed when the nucleic acid comprises two portions that are sufficiently complementary to each other to form a plurality of consecutive base pairs.

As used herein, the term "FRET" refers to fluorescence resonance energy transfer, a process in which moieties (e.g., fluorophores) transfer energy e.g., among themselves, or, from a fluorophore to a non-fluorophore (e.g., a quencher molecule). In some circumstances, FRET involves an excited donor fluorophore transferring energy to a lower-energy acceptor fluorophore via a short-range (e.g., about 10 nm or less) dipole-dipole interaction. In other circumstances, FRET involves a loss of fluorescence energy from a donor and an increase in fluorescence in an acceptor fluorophore. In still other forms of FRET, energy can be exchanged from an excited donor flurophore to a non-fluorescing molecule (e.g., a quenching molecule). FRET is known to those of skill in the art and has been described (See, e.g., Stryer et al., 1978, Ann. Rev. Biochem., 47:819; Selvin, 1995, Methods Enzymol., 246:300; Orpana, 2004 Biomol Eng 21, 45-50; Olivier, 2005 Mutant Res 573, 103-110, each of which is incorporated herein by reference in its entirety).

As used herein, the term "FEN-1" in reference to an enzyme refers to a non-polymerase flap endonuclease from a eukaryote or archaeal organism. See, e.g., WO 02/070755, and Kaiser M. W., et al. (1999) J. Biol. Chem., 274:21387, which are incorporated by reference herein in their entireties for all purposes.

As used herein, the term "FEN-1 activity" refers to any enzymatic activity of a FEN-1 enzyme, including but not limited to flap endonuclease (FEN), nick exonuclease (EXO), and gap endonuclease (GEN) activities (see, e.g., Shen, et al., BioEssays Volume 27, Issue 7, Pages 717-729, incorporated herein by reference).

As used herein, the term "primer annealing" refers to conditions that permit oligonucleotide primers to hybridize to template nucleic acid strands. Conditions for primer annealing vary with the length and sequence of the primer and are generally based upon the Tm that is determined or calculated for the primer. For example, an annealing step in an amplification method that involves thermocycling involves reducing the temperature after a heat denaturation step to a temperature based on the Tm of the primer sequence, for a time sufficient to permit such annealing.

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target." In contrast, "background template" is used in reference to nucleic acid other than sample template that may or may not be present in a sample. The presence of background template is most often inadvertent. It may be the result of carryover, or it may be due to the presence of nucleic acid contaminants sought to be purified away from the sample. For example, nucleic acids from organisms other than those to be detected may be present as background in a test sample.

A sample "suspected of containing" a nucleic acid may contain or not contain the target nucleic acid molecule.

The term "real time" as used herein in reference to detection of nucleic acid amplification or signal amplification refers to the detection or measurement of the accumulation of products or signal in the reaction while the reaction is in progress, e.g., during incubation or thermal cycling. Such detection or measurement may occur continuously, or it may occur at a plurality of discrete points during the progress of the amplification reaction, or it may be a combination. For example, in a polymerase chain reaction, detection (e.g., of fluorescence) may occur continuously during all or part of thermal cycling, or it may occur transiently, at one or more points during one or more cycles. In some embodiments, real time detection of PCR is accomplished by determining a level of fluorescence at the same point (e.g., a time point in the cycle, or temperature step in the cycle) in each of a plurality of cycles, or in every cycle. Real time detection of amplification may also be referred to as detection "during" the amplification reaction.

As used herein, the terms "reverse transcription" and "reverse transcribe" refer to the use of a template-dependent polymerase to produce a DNA strand complementary to an RNA template. A polymerase capable of producing a DNA strand complementary to an RNA template is generally referred to as a "reverse transcriptase" or as a polymerase that has "reverse transcriptase activity".

As used herein, the term "abundance of nucleic acid" refers to the amount of a particular target nucleic acid sequence present in a sample or aliquot. The amount is generally referred to in terms of mass (e.g., µg), mass per unit of volume (e.g., µg/µl); copy number (e.g., 1000 copies, 1 attomole), or copy number per unit of volume (e.g., 1000 copies per ml, 1 attomole per µl). Abundance of a nucleic acid can also be expressed as an amount relative to the amount of a standard of known concentration or copy number. Measurement of abundance of a nucleic acid may be on any basis understood by those of skill in the art as being a suitable quantitative representation of nucleic acid abundance, including physical density or the sample, optical density, refractive property, staining properties, or on the basis of the intensity of a detectable label, e.g. a fluorescent label.

The term "amplicon" or "amplified product" refers to a segment of nucleic acid, generally DNA, generated by an amplification process such as the PCR process. The terms are also used in reference to RNA segments produced by amplification methods that employ RNA polymerases, such as NASBA, TMA, etc.

The term "amplification plot" as used in reference to a thermal cycling amplification reaction refers to the plot of signal that is indicative of amplification, e.g., fluorescence signal, versus cycle number. When used in reference to a non-thermal cycling amplification method, an amplification plot generally refers to a plot of the accumulation of signal as a function of time.

The term "baseline" as used in reference to an amplification plot refers to the detected signal coming from assembled amplification reactions at prior to incubation or, in the case of PCR, in the initial cycles, in which there is little change in signal.

The term "no template control" and "no target control" (or "NTC") as used herein in reference to a control reaction refers to a reaction or sample that does not contain template or target nucleic acid. It is used to verify amplification quality.

As used herein, the term "quantitative amplification data set" refers to the data obtained during quantitative amplification of the target sample, e.g., target DNA. In the case of quantitative PCR or QuARTS assays, the quantitative amplification data set is a collection of fluorescence values obtained at during amplification, e.g., during a plurality of, or all of the thermal cycles. Data for quantitative amplification is not limited to data collected at any particular point in a reaction, and fluorescence may be measured at a discrete point in each cycle or continuously throughout each cycle.

The abbreviations "Ct" and "Cp" as used herein in reference to real-time detection during an amplification reaction that is thermal cycled refers to the cycle at which signal (e.g., fluorescent signal) crosses a predetermined threshold value indicative of positive signal. Various methods have been used to calculate the threshold that is used as a determinant of signal verses concentration, and the value is generally expressed as either the "crossing threshold" (Ct) or the "crossing point" (Cp). Either Cp values or Ct values may be used in embodiments of the methods presented herein for analysis of real-time signal for the determination of the amount of RNA marker(s) or reference markers in an assay or sample.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contain a subportion of the total kit components. The containers may be delivered to the intended recipient together or separately. For example, a first container may contain an enzyme for use in an assay, while a second container contains oligonucleotides.

The term "system" as used herein refers to a collection of articles for use for a particular purpose. In some embodiments, the articles comprise instructions for use, as information supplied on e.g., an article, on paper, or on recordable media (e.g., DVD, CD, flash drive, etc.). In some embodiments, instructions direct a user to an online location, e.g., a website.

As used herein, the term "information" refers to any collection of facts or data. In reference to information stored or processed using a computer system(s), including but not limited to internets, the term refers to any data stored in any format (e.g., analog, digital, optical, etc.). As used herein, the term "information related to a subject" refers to facts or data pertaining to a subject (e.g., a human, plant, or animal). The term "genomic information" refers to information pertaining to a genome including, but not limited to, nucleic acid sequences, genes, percentage methylation, allele frequencies, RNA expression levels, protein expression, phenotypes correlating to genotypes, etc. "Allele frequency information" refers to facts or data pertaining to allele frequencies, including, but not limited to, allele identities, statistical correlations between the presence of an allele and a characteristic of a subject (e.g., a human subject), the presence or absence of an allele in an individual or population, the percentage likelihood of an allele being present in an individual having one or more particular characteristics, etc.

DESCRIPTION OF THE DRAWINGS

FIG. 2 compares the effects of different amounts of reverse transcriptase and different reverse transcription conditions on the detection of known amounts of target RNA in RT-QuARTS assays.

FIG. 3 shows graphs showing standard curves measuring marker LRG1 RNA. Panel A describes the dilution series, the average Cp value at each dilution, and the calculated strands/reaction calculated from the amplification plots shown in panel B. Panel C shows a graph comparing the Cp compared to the log of the amount of RNA present in the sample.

FIG. 5 shows graphs comparing the sensitivity and specificity when samples are analyzed using the combinations of four or six expression markers, as listed above each panel.

DETAILED DESCRIPTION OF THE INVENTION

Figure 1:
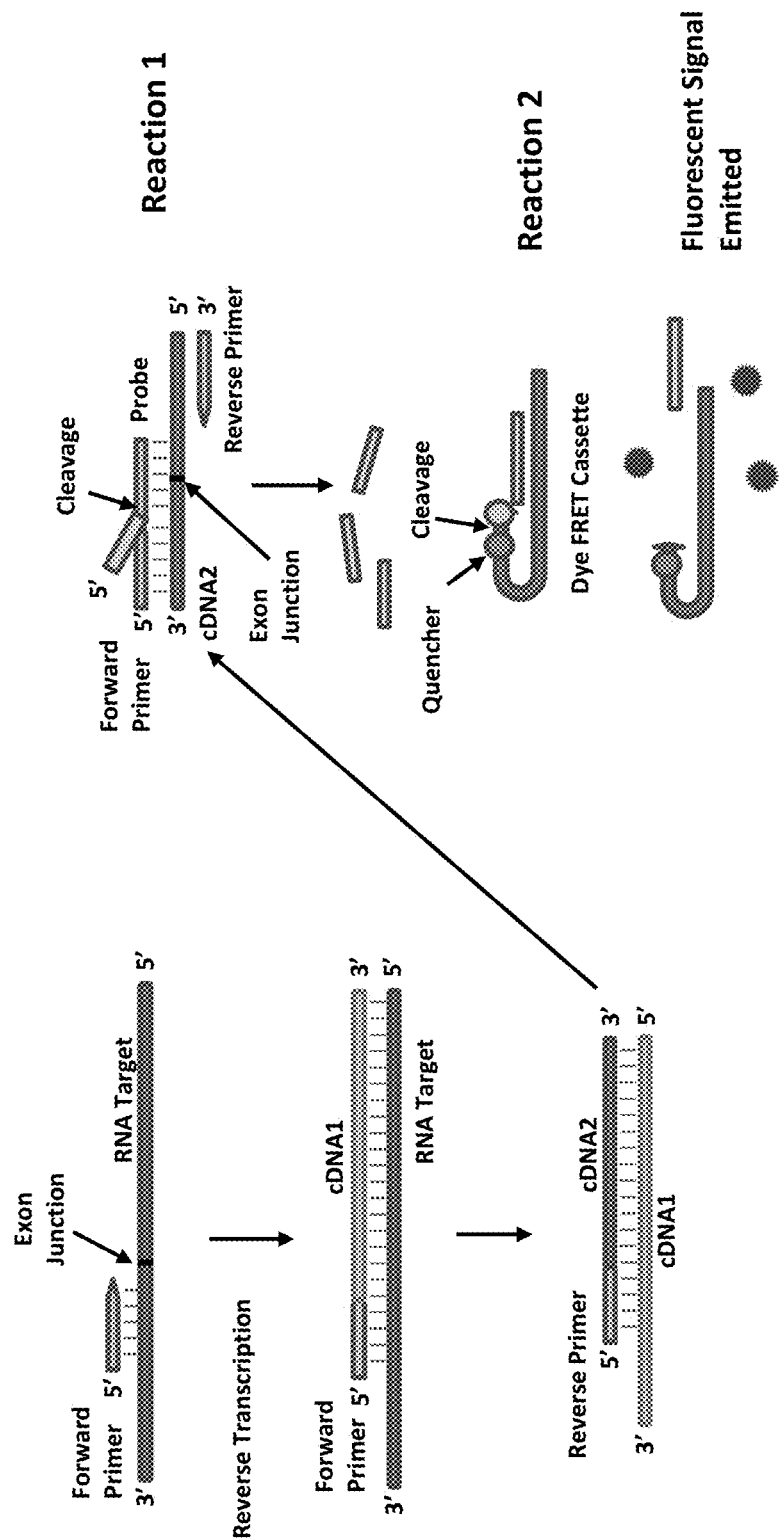
FIG. 1 shows a schematic diagram of a combined reverse transcription-QuARTS flap endonuclease detection assay for real-time detection of RNA. Use of multiple different probe flap/FRET cassette dye combinations allows multiple different target nucleic acids to be detected together in multiplex reactions.

Provided herein is technology relating to RNA expression markers for use in assays for detection and quantification of RNA. In particular, the technology relates to use of RNA-based gene expression assays to detect lung cancer.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

The methods and compositions provided herein relate to characterizing the expression from marker genes by characterizing RNA molecules ("RNA markers") in a sample, wherein the RNA presence, absence, or status (e.g., with respect to post-transcription modifications or processing) is indicative of neoplasia. Accordingly, provided here are compositions and method directed toward analysis of RNA markers that correlate with lung neoplasia. In preferred embodiments the technology provides assays wherein RNA markers are reverse transcribed, amplified, and detected in real time in a single reaction mixture, and in a single vessel.

Also provided herein are compositions and kits for practicing the methods. For example, in some embodiments, reagents (e.g., primers, probes) specific for one or more RNA expression markers are provided alone or in sets (e.g., sets of primers pairs for amplifying a plurality of RNA markers). Additional reagents for conducting a detection assay may also be provided (e.g., enzymes, buffers, positive and negative controls for conducting QuARTS assays, RT-QuARTS assays, PCR, sequencing, or other assays). In some embodiments, the kits containing one or more reagent necessary, sufficient, or useful for conducting a method are provided. Also provided are reactions mixtures containing the reagents. Further provided are master mix reagent sets containing a plurality of reagents that may be added to each other and/or to a test sample to complete a reaction mixture.

The technology relates to the analysis of any sample associated with lung cancer. For example, in some embodiments the sample comprises a tissue and/or biological fluid obtained from a patient. In some embodiments, the sample comprises a secretion. In some embodiments, the sample comprises sputum, blood, serum, plasma, lung tissue samples, or lung cells. In some embodiments, the subject is human. Such samples can be obtained by any number of means known in the art, such as will be apparent to the skilled person.

I. RNA Detection Assays to Detect Lung Cancer

Eight candidate mRNA markers (GAGE12D, FAM83A, LRG1, XAGE-1 d, MAGEA4, SFTPB, AKAP4, and CYP24A1) were selected based on discrimination reported in the literature. As described below, samples from 246 patients (119 controls, 127 lung cancer cases) were tested. The lung cancer cases comprised adena (65), squamous (34), large cell (13), small cell (4) and others carcinomas (11). The controls were from patients having benign lung nodules (37), normal lung (60), chronic obstructive pulmonary disorder (COPD) (10), and normal lung adjacent to tumor (12). Cases and controls included smokers and non-smokers.

Messenger RNA expression levels were assayed in a single-tube reverse transcription QuARTS (Quantitative Allele-5pecific Real-time Target and Signal amplification) as described herein below, a reaction configuration that simultaneously measures copy numbers of two mRNA markers and a housekeeping reference mRNA (CASC3). To account for sample-to-sample variability, relative gene expression values of each mRNA marker were calculated by dividing the copy numbers obtained for each of the mRNAs by the CASC3 mRNA copy number.

Receiver operator characteristic (ROC) curve analyses resulted in an area under the curve (AUC) of 0.976. At 100% specificity, the mRNA panel of 6 markers achieved a sensitivity of 92.1% for all cancers (117/127) and 93.9% for adenocarcinoma and squamous carcinoma combined (93/99).

II. RNA Detection Assays and Kits

The markers described herein find use in a variety of RNA expression assays, e.g., qRT-PCR, digital PCR, gene expression arrays, etc. In some embodiments, a modified version of a quantitative real-time target and signal amplification (QuARTS) assay is used to evaluate gene expression. In DNA detection, three reactions occur during each QuARTS assay, including amplification (reaction 1) and target probe cleavage (reaction 2) in the primary reaction; and FRET cleavage and fluorescent signal generation (reaction 3) in the secondary reaction. After the first few cycles generate initial amounts of cleaved probe, these reactions occur essentially concurrently. As modified herein, a reverse transcription step is included to produce cDNA for QuARTS flap assay detection.

When target nucleic acid is amplified with specific primers, a specific detection probe with a flap sequence loosely binds to the amplicon. The presence of the specific invasive oligonucleotide at the target binding site causes a 5' nuclease, e.g., a FEN-1 endonuclease, to release the flap sequence by cutting between the detection probe and the flap sequence. The flap sequence is complementary to a non-hairpin portion of a corresponding FRET cassette. Accordingly, the flap sequence functions as an invasive oligonucleotide on the FRET cassette and effects a cleavage between the FRET cassette fluorophore and a quencher, which produces a fluorescent signal. The cleavage reaction can cut multiple probes per target and thus release multiple fluorophore per flap, providing exponential signal amplification. A QuARTS flap endonuclease assay can detect multiple targets in a single reaction vessel, e.g., by using FRET cassettes with different dyes.

Methods of isolating RNA from samples are known in the art. For example, RNA isolation methods may comprise one or more of organic extraction, ultrafiltration, hybrid capture, etc. In some embodiments, cells or lysed samples containing RNA may be added directly to assay reactions without purification.

In some embodiments, the sample comprises blood, serum, plasma, or saliva. In some embodiments, the subject is human. Such samples can be obtained by any number of means known in the art, such as will be apparent to the skilled person. Cell free or substantially cell free samples can be obtained by subjecting the sample to various techniques known to those of skill in the art which include, but are not limited to, centrifugation and filtration. Although it is generally preferred that no invasive techniques are used to obtain the sample, it still may be preferable to obtain samples such as tissue homogenates, tissue sections, and biopsy specimens. The technology is not limited in the methods used to prepare the samples and provide a nucleic acid for testing. For example, in some embodiments, a RNA is isolated from blood or from a plasma sample using a hybrid capture method, e.g., using target-specific binding materials (e.g., oligonucleotides) on solid supports.

The analysis of markers can be carried out separately or simultaneously with additional markers within one test sample. For example, several markers can be combined into one test for efficient processing of multiple samples and for potentially providing greater diagnostic and/or prognostic accuracy. In addition, one skilled in the art would recognize the value of testing multiple samples (for example, at successive time points) from the same subject. Such testing of serial samples can allow the identification of changes in marker expression over time. Changes in expression, as well as the absence of change in expression, can provide useful information about the disease status that includes, but is not limited to, identifying the approximate time from onset of the event, the presence and amount of salvageable tissue, the appropriateness of drug therapies, the effectiveness of various therapies, and identification of the subject's outcome, including risk of future events.

The analysis of biomarkers can be carried out in a variety of physical formats. For example, the use of microtiter plates or automation can be used to facilitate the processing of large numbers of test samples. Alternatively, single sample formats could be developed to facilitate immediate treatment and diagnosis in a timely fashion, for example, in ambulatory transport or emergency room settings.

It is contemplated that embodiments of the technology are provided in the form of a kit. The kits comprise embodiments of the compositions, devices, apparatuses, etc. described herein, and instructions for use of the kit. Such instructions describe appropriate methods for preparing an analyte from a sample, e.g., for collecting a sample and preparing a nucleic acid from the sample. Individual components of the kit are packaged in appropriate containers and packaging (e.g., vials, boxes, blister packs, ampules, jars, bottles, tubes, and the like) and the components are packaged together in an appropriate container (e.g., a box or boxes) for convenient storage, shipping, and/or use by the user of the kit. It is understood that liquid components (e.g., a buffer) may be provided in a lyophilized form to be reconstituted by the user. Kits may include a control or reference for assessing, validating, and/or assuring the performance of the kit. For example, a kit for assaying the amount of a nucleic acid present in a sample may include a control comprising a known concentration of the same or another nucleic acid for comparison and, in some embodiments, a detection reagent (e.g., a primer) specific for the control nucleic acid. The kits are appropriate for use in a clinical setting and, in some embodiments, for use in a user's home. The components of a kit, in some embodiments, provide the functionalities of a system for preparing a nucleic acid solution from a sample. In some embodiments, certain components of the system are provided by the user.

III. Applications

In some embodiments, diagnostic assays identify the presence of a disease or condition in an individual. In some embodiments, the disease is cancer (e.g., lung cancer). In preferred embodiments, markers whose aberrant expression is associated with a lung cancer (e.g., one or more markers selected GAGE12D, FAM83A, LRG1, XAGE-1 d, MAGEA4, SFTPB, AKAP4, and CYP24A1) are used. In some embodiments, an assay further comprises detection of a reference nucleic acid (e.g., CASC3 or β-actin mRNAs; U1 and U6 snRNAs, etc.).

In some embodiments, the technology finds application in treating a patient (e.g., a patient with lung cancer, with early stage lung cancer, or who may develop lung cancer), the method comprising determining the expression levels of one or more markers as provided herein and administering a treatment to the patient based on the results of determining the expression levels. The treatment may be administration of a pharmaceutical compound, a vaccine, performing a surgery, imaging the patient, performing another test. Preferably, said use is in a method of clinical screening, a method of prognosis assessment, a method of monitoring the results of therapy, a method to identify patients most likely to respond to a particular therapeutic treatment, a method of imaging a patient or subject, and a method for drug screening and development.

In some embodiments, the technology finds application in methods for diagnosing lung cancer in a subject is provided. The terms "diagnosing" and "diagnosis" as used herein refer to methods by which the skilled artisan can estimate and even determine whether or not a subject is suffering from a given disease or condition or may develop a given disease or condition in the future. The skilled artisan often makes a diagnosis on the basis of one or more diagnostic indicators, such as for example a biomarker, the expression of which is indicative of the presence, severity, or absence of the condition.

Along with diagnosis, clinical cancer prognosis relates to determining the aggressiveness of the cancer and the likelihood of tumor recurrence to plan the most effective therapy. If a more accurate prognosis can be made or even a potential risk for developing the cancer can be assessed, appropriate therapy, and in some instances less severe therapy for the patient can be chosen. Assessment (e.g., analyzing expression) of cancer biomarkers is useful to separate subjects with good prognosis and/or low risk of developing cancer who will need no therapy or limited therapy from those more likely to develop cancer or suffer a recurrence of cancer who might benefit from more intensive treatments.

As such, "making a diagnosis" or "diagnosing", as used herein, is further inclusive of making determining a risk of developing cancer or determining a prognosis, which can provide for predicting a clinical outcome (with or without medical treatment), selecting an appropriate treatment (or whether treatment would be effective), or monitoring a current treatment and potentially changing the treatment, based on the measure of the diagnostic biomarkers disclosed herein.

Further, in some embodiments of the technology, multiple determinations of the biomarkers over time can be made to facilitate diagnosis and/or prognosis. A temporal change in the biomarker can be used to predict a clinical outcome, monitor the progression of lung cancer, and/or monitor the efficacy of appropriate therapies directed against the cancer. In such an embodiment for example, one might expect to see a change in the expression of one or more biomarkers disclosed herein (and potentially one or more additional biomarker(s), if monitored) in a biological sample over time during the course of an effective therapy.

The technology further finds application in methods for determining whether to initiate or continue prophylaxis or treatment of a cancer in a subject. In some embodiments, the method comprises providing a series of biological samples over a time period from the subject; analyzing the series of biological samples to determine expression of at least one biomarker disclosed herein in each of the biological samples; and comparing any measurable change in the expression of one or more of the biomarkers in each of the biological samples. Any changes in the expression of biomarkers over the time period can be used to predict risk of developing cancer, predict clinical outcome, determine whether to initiate or continue the prophylaxis or therapy of the cancer, and whether a current therapy is effectively treating the cancer. For example, a first time point can be selected prior to initiation of a treatment and a second time point can be selected at some time after initiation of the treatment. Expression can be measured in each of the samples taken from different time points and qualitative and/or quantitative differences noted. A change in the expression of the biomarkers from the different samples can be correlated with risk for developing lung, prognosis, determining treatment efficacy, and/or progression of the cancer in the subject.

In preferred embodiments, the methods and compositions of the invention are for treatment or diagnosis of disease at an early stage, for example, before symptoms of the disease appear. In some embodiments, the methods and compositions of the invention are for treatment or diagnosis of disease at a clinical stage.

As noted above, in some embodiments multiple determinations of one or more diagnostic or prognostic biomarkers can be made, and a temporal change in the marker can be used to determine a diagnosis or prognosis. For example, a diagnostic marker can be determined at an initial time, and again at a second time. In such embodiments, an increase in the marker from the initial time to the second time can be diagnostic of a particular type or severity of cancer, or a given prognosis. Likewise, a decrease in the marker from the initial time to the second time can be indicative of a particular type or severity of cancer, or a given prognosis. Furthermore, the degree of change of one or more markers can be related to the severity of the cancer and future adverse events. The skilled artisan will understand that, while in certain embodiments comparative measurements can be made of the same biomarker at multiple time points, one can also measure a given biomarker at one time point, and a second biomarker at a second time point, and a comparison of these markers can provide diagnostic information.

As used herein, the phrase "determining the prognosis" refers to methods by which the skilled artisan can predict the course or outcome of a condition in a subject. The term "prognosis" does not refer to the ability to predict the course or outcome of a condition with 100% accuracy, or even that a given course or outcome is predictably more or less likely to occur based on the expression of a biomarker. Instead, the skilled artisan will understand that the term "prognosis" refers to an increased probability that a certain course or outcome will occur; that is, that a course or outcome is more likely to occur in a subject exhibiting a given condition, when compared to those individuals not exhibiting the condition. For example, in individuals not exhibiting the condition, the chance of a given outcome (e.g., suffering from lung cancer) may be very low.

In some embodiments, a statistical analysis associates a prognostic indicator with a predisposition to an adverse outcome. For example, in some embodiments, an expression level different from that in a normal control sample obtained from a patient who does not have a cancer can signal that a subject is more likely to suffer from a cancer than subjects with a level that is more similar to the expression level in the control sample, as determined by a level of statistical significance. Additionally, a change in expression level from a baseline (e.g., "normal") level can be reflective of subject prognosis, and the degree of change in expression can be related to the severity of adverse events. Statistical significance is often determined by comparing two or more populations and determining a confidence interval and/or a p value. See, e.g., Dowdy and Wearden, Statistics for Research, John Wiley & Sons, New York, 1983, incorporated herein by reference in its entirety. Exemplary confidence intervals of the present subject matter are 90%, 95%, 97.5%, 98%, 99%, 99.5%, 99.9% and 99.99%, while exemplary p values are 0.1, 0.05, 0.025, 0.02, 0.01, 0.005, 0.001, and 0.0001.

In other embodiments, a threshold degree of change in expression of a prognostic or diagnostic biomarker disclosed herein can be established, and the degree of change in the expression of the biomarker in a biological sample is simply compared to the threshold degree of change in the expression. A preferred threshold change in the expression level for biomarkers provided herein is about 5%, about 10%, about 15%, about 20%, about 25%, about 30%, about 50%, about 75%, about 100%, and about 150%. In yet other embodiments, a "nomogram" can be established, by which expression of a prognostic or diagnostic indicator (biomarker or combination of biomarkers) is directly related to an associated disposition towards a given outcome. The skilled artisan is acquainted with the use of such nomograms to relate two numeric values with the understanding that the uncertainty in this measurement is the same as the uncertainty in the marker concentration because individual sample measurements are referenced, not population averages.

In some embodiments, a control sample is analyzed concurrently with the biological sample, such that the results obtained from the biological sample can be compared to the results obtained from the control sample. Additionally, it is contemplated that standard curves can be provided, with which assay results for the biological sample may be compared. Such standard curves present expression levels of a biomarker as a function of assay units, e.g., fluorescent signal intensity, if a fluorescent label is used. Using samples taken from multiple donors, standard curves can be provided for control expression of the one or more biomarkers in normal tissue, as well as for "at-risk" levels of the one or more biomarkers in tissue taken from donors with lung cancer.

The analysis of markers can be carried out separately or simultaneously with additional markers within one test sample. For example, several markers can be combined into one test for efficient processing of a multiple of samples and for potentially providing greater diagnostic and/or prognostic accuracy. In addition, one skilled in the art would recognize the value of testing multiple samples (for example, at successive time points) from the same subject. Such testing of serial samples can allow the identification of changes in marker expression over time. Changes in expression, as well as the absence of change in expression, can provide useful information about the disease status that includes, but is not limited to, identifying the approximate time from onset of the event, the presence and amount of salvageable tissue, the appropriateness of drug therapies, the effectiveness of various therapies, and identification of the subject's outcome, including risk of future events.

The analysis of biomarkers can be carried out in a variety of physical formats. For example, the use of microtiter plates or automation can be used to facilitate the processing of large numbers of test samples. Alternatively, single sample formats could be developed to facilitate immediate treatment and diagnosis in a timely fashion, for example, in ambulatory transport or emergency room settings.

In some embodiments, the subject is diagnosed as having lung cancer if, when compared to a control expression, there is a measurable difference in the expression of at least one biomarker in the sample. Conversely, when no change in expression is identified in the biological sample, the subject can be identified as not having lung cancer, not being at risk for the cancer, or as having a low risk of the cancer. In this regard, subjects having lung cancer or risk thereof can be differentiated from subjects having low to substantially no cancer or risk thereof. Those subjects having a risk of developing lung cancer can be placed on a more intensive and/or regular screening schedule. On the other hand, those subjects having low to substantially no risk may avoid being subjected to screening procedures, until such time as a future screening, for example, a screening conducted in accordance with the present technology, indicates that a risk of lung cancer has appeared in those subjects.

As mentioned above, depending on the embodiment of the method of the present technology, detecting a change in expression of the one or more biomarkers can be a qualitative determination or it can be a quantitative determination. As such, the step of diagnosing a subject as having, or at risk of developing, lung cancer indicates that certain threshold measurements are made, e.g., the expression of the one or more biomarkers in the biological sample varies from a predetermined control expression. In some embodiments of the method, the control expression is any detectable expression of the biomarker. In other embodiments of the method where a control sample is tested concurrently with the biological sample, the predetermined expression is the expression in the control sample. In other embodiments of the method, the predetermined expression is based upon and/or identified by a standard curve. In other embodiments of the method, the predetermined expression is a specifically state or range of state. As such, the predetermined expression can be chosen, within acceptable limits that will be apparent to those skilled in the art, based in part on the embodiment of the method being practiced and the desired specificity, etc.

Over recent years, it has become apparent that circulating epithelial cells, representing metastatic tumor cells, can be detected in the blood of many patients with cancer. Molecular profiling of rare cells is important in biological and clinical studies. Applications range from characterization of circulating epithelial cells (CEpCs) in the peripheral blood of cancer patients for disease prognosis and personalized treatment (See e.g., Cristofanilli M, et al. (2004) N Engl J Med 351:781-791; Hayes D F, et al. (2006) Clin Cancer Res 12:4218-4224; Budd G T, et al., (2006) Clin Cancer Res 12:6403-6409; Moreno J G, et al. (2005) Urology 65:713-718; Pantel et al., (2008) Nat Rev 8:329-340; and Cohen S J, et al. (2008) J Clin Oncol 26:3213-3221). Accordingly, embodiments of the present disclosure provide compositions and methods for detecting the presence of metastatic cancer in a subject by identifying the presence of expression markers in plasma or whole blood.

Experimental Examples

Tissue Extraction.

Tissue samples were obtained from various commercial and non-commercial sources (Asuragen, BioServe, ConversantBio, Cureline, Mayo Clinic, M D Anderson, and PrecisionMed). Tissue sections were examined by a pathologist, who circled histologically distinct lesions to direct careful micro-dissection. Total nucleic acid extraction was performed using the Promega Maxwell RSC system. FFPE slides were scraped and extracted using the Maxwell® RSC DNA FFPE Kit (#AS1450) using the manufacturer's procedure but skipping the RNase digestion step. The same procedure was used for FFPE bulk curls. For frozen punch biopsy samples, a modified procedure using the lysis buffer from the RSC DNA FFPE kit with the Maxwell® RSC Blood DNA kit (#AS1400) was utilized omitting the RNase step. Prior to testing, samples were diluted 1:5 in 20 ng/µL tRNA in 10 mM TrisHCl, pH 8.0, 0.1 mM EDTA.

Gene Expression Markers

Gene expression markers tested comprised AKAP4GAGE12D, FAM83A, SFTPB (Pro-Surfactant B), XAGE-1D, CYP24A1, LRG1, and MAGEA4, and one reference gene expression were tested on lung cancer tissue samples. Expression of CASC3 was used as a reference marker.

Lung Tissue Samples 127 cancer tissue samples and 119 normal lung tissue samples were tested. The tissue types tested are summarized in the following tables:

| Cancer Tissue Subtypes | N | Normal Tissue | N |
|---|---|---|---|
| Adenocarcinoma | 65 | Benign lung nodules | 37 |
| Bronchioloalveolar | 6 | Adjacent normal tissue | 72 |
| Large cell carcinoma | 13 | COPD tissue | 10 |

-continued

| Cancer Tissue Subtypes | N | Normal Tissue | N |
|---|---|---|---|
| Neuroendocrine | 2 | | |
| Small cell carcinoma | 4 | | |
| Squamous cell carcinoma | 34 | | |
| Unknown | 3 | | |

RT-QuARTS.

A QuARTS flap endonuclease assay reaction was modified to add a reverse transcription step. The assay probes were designed to span exon junctions so that the RT-QuARTS assay would specifically detect mRNA targets rather than the corresponding genomic loci. Briefly, the technique combines a reverse transcription step to convert the RNA target into a cDNA strand, a polymerase based target amplification and a simultaneous invasive cleavage signal amplification reaction (FIG. 1). The format results in a real-time accumulation of fluorescent signal in proportion to the amount of target mRNA. It produces a similar output to quantitative RT-PCR, but with the added sensitivity and specificity resulting from the addition of the invasive cleavage reaction. RT-QuARTS reactions comprising different amounts of Molony Murine Leukemia Virus (MMLV) reverse transcriptase and different dilutions of RNA were conducted using a reverse transcription reactions for 10 to 45 minutes. FIG. 2 provides a table comparing the results of the different reaction conditions.

Each triplex RT-QuARTS assay as describe below consists of one mRNA target reporting to FAM, one to HEX, and the reference mRNA to Quasar 670. Standard curves for each assay were generated by serially diluting known quantities of in vitro-produced transcripts for each marker. Standard curves were created by plotting Cp value by Log input strands. The resulting slope and intercept values were used to convert the Cp values of the unknown samples to mRNA strand values. Oligonucleotide sequences for the assays are shown in Table 1.

In vitro transcripts for each target were made from templates containing the DNA sequence amplified in the QuARTS reaction with additional flanking 5' and 3' sequences coupled to a T7 promoter. In vitro transcription was done using the T7 Ribomax system (Promega) and the resulting transcripts were quantitated with the Quant-iT RNA assay kit (Thermo Fisher Scientific).

Without reverse transcription, an exemplary QuARTS reaction typically comprises approximately 400-600 nmol/l (e.g., 500 nmol/l) of each primer and detection probe, approximately 100 nmol/l of the invasive oligonucleotide, approximately 600-700 nmol/l of each FRET cassette (FAM, e.g., as supplied commercially by Hologic, Inc.; HEX, e.g., as supplied commercially by BioSearch Technologies; and Quasar 670, e.g., as supplied commercially by BioSearch Technologies), 6.675 ng/µl FEN-1 endonuclease (e.g., Cleavase® 2.0, Hologic, Inc.), 1 unit Taq DNA polymerase in a 30 µl reaction volume (e.g., GoTaq® DNA polymerase, Promega Corp., Madison, WI), 10 mmol/l 3-(n-morpholino) propanesulfonic acid (MOPS), 7.5 mmol/l $MgCl_2$, and 250 µmol/l of each dNTP. Exemplary QuARTS cycling conditions are as shown in the table below. In some applications, analysis of the quantification cycle ($C_q$) provides a measure of the initial number of target DNA strands (e.g., copy number) in the sample.

RT-QuARTS reactions contained 20U of MMLV reverse transcriptase (MMLV-RT), 219 ng of Cleavase® 2.0, 1.5U of GoTaq® DNA Polymerase, 200 nM of each primer, 500 nM each of probe and FRET oligonucleotides, 10 mM MOPS buffer, pH7.5, 7.5 mM $MgCl_2$, and 250 µM each dNTP. Reactions were run on a Roche LightCycler 480 system under the following conditions: 42° C. for 30 minutes (RT reaction), 95° C. for 3 min, 10 cycles of 95° C. for 20 seconds, 63° C. for 30 sec, 70° C. for 30 sec, followed by 35 cycles of 95° C. for 20 sec, 53° C. for 1 min, 70° C. for 30 sec, and hold at 40° C. for 30 sec.

RT-QuARTS with Multiplex Preamplification

In some embodiments, RT-QuARTS assays may comprise a step of multiplex pre-amplification, e.g., to pre-amplify 10, 12, or more targets in as sample. Multiplex pre-amplification for QuARTS assays is described, e.g., in U.S. patent application Ser. Nos. 62/249,097, filed Oct. 30, 2015, and 62/332,295, filed May 5, 2016, each of which is incorporated herein by reference.

An RT-pre-amplification is conducted in a reaction mixture containing, e.g., 20U of MMLV reverse transcriptase, 1.5U of GoTaq® DNA Polymerase, 10 mM MOPS buffer, pH7.5, 7.5 mM $MgCl_2$, 250 μM each dNTP, and oligonucleotide primers, (e.g., for 12 targets, 12 primer pairs/24 primers, in equimolar amounts (e.g., 200 nM each primer), or with individual primer concentrations adjusted to balance amplification efficiencies of the different targets). Thermal cycling times and temperatures are selected to be appropriate for the volume of the reaction and the amplification vessel. For example, the reactions may be cycled as follows:

| Stage | Temp/Time | # of Cycles |
|---|---|---|
| RT | 42° C./30' | 1 |
|  | 95° C./3' | 1 |
| Amplification 1 | 95° C./20" | 10 |
|  | 63° C./30" |  |
|  | 70° C./30" |  |
| Cooling | 4° C./Hold | 1 |

After thermal cycling, aliquots of the pre-amplification reaction (e.g., 10 μL) are diluted to 500 μL in 10 mM Tris, 0.1 mM EDTA, with or without fish DNA. Aliquots of the diluted pre-amplified DNA (e.g., 10 μL) are used in QuARTS PCR-flap assay, e.g., as described above.

In some embodiments, DNA targets, e.g., methylated DNA marker genes, genes corresponding to the RNA marker, etc., may be amplified and detected along with the reverse-transcribed cDNAs in a QuARTS assay reaction. In some embodiments, DNA and cDNA are co-amplified and detected in a single-tube reaction, i.e., without the need to open the reaction vessel at any point between combining the reagents and collecting the output data. In other embodiments, marker DNA from the same sample or from a different sample, may be separately isolated, with or without a bisulfite conversion step, and may be combined with sample RNA in an RT-QuARTS assay. In yet other embodiments, RNA and/or DNA samples may be pre-amplified as described above.

The amplification primers and probes used for reverse transcription, amplification, and the flap endonuclease reactions that occur in the RT-QuARTS assay as described herein are shown in Table 1, below:

TABLE 1

| AKAP4 | Forward Primer | 5'-GGACACTGAGAAGAAAGACCAGTC (SEQ ID NO: 1) |
|---|---|---|
|  | Reverse Primer | 5'-GGGAGCTTGTTTGAAAAGGCA (SEQ ID NO: 2) |
|  | Probe | 5'-CCACGGACGCTAAGACAGAGG/3C6/ (SEQ ID NO: 3) |

TABLE 1-continued

| CASC3 | Forward Primer | 5'-CTGCAACCACGGGAACTT (SEQ ID NO: 4) |
|---|---|---|
|  | Reverse Primer | 5'-GAGGTGGAGGTCCTGCTC (SEQ ID NO: 5) |
|  | Probe | 5'-GACGCGGAGTCGAGGTATGCC/3C6/ (SEQ ID NO: 6) |
| CYP24A1 | Forward Primer | 5'-CTTCAACTGCATTTGGCTCTTTG (SEQ ID NO: 7) |
|  | Reverse Primer | 5'-TGTGGCCTGGATGTCGT (SEQ ID NO: 8) |
|  | Probe | 5'-CCACGGACGGTTGGATTGTCC/3C6/ (SEQ ID NO: 9) |
| FAM83A | Forward Primer | 5'-TGGAGATTTGTCCTGTCTGGATC (SEQ ID NO: 10) |
|  | Reverse Primer | 5'-CTTGGAGAGGATGTTCCGGT (SEQ ID NO: 11) |
|  | Probe | 5'-CCACGGACGCTTACAGCTTCA/3C6/ (SEQ ID NO: 12) |
| GAGE12D | Forward Primer | 5'-AGGGAGCATCTGCAGGTC (SEQ ID NO: 13) |
|  | Reverse Primer | 5'-CCTGTTCCTGGCTATGAGCTTC (SEQ ID NO: 14) |
|  | Probe | 5'-CGCCGAGGCAAGGGCCGAAG/3C6/ (SEQ ID NO: 15) |
| LRG1 | Forward Primer | 5'-GAGCAGACAGCGACCAAA (SEQ ID NO: 16) |
|  | Reverse Primer | 5'-CAGGAACAGAGTTCTAGAAACATGG (SEQ ID NO: 17) |
|  | Probe | 5'-CCACGGACGAAAGCCCAGGGG/3C6/ (SEQ ID NO: 18) |
| MAGEA4 | Forward Primer | 5'-AGAGGAGCACCAAGGAGAAGA (SEQ ID NO: 19) |
|  | Reverse Primer | 5'-GGCAAAAGCTGGGCAATGG (SEQ ID NO: 20) |
|  | Probe | 5'-CGCCGAGGATCTGCCTGTGG/3C6/ (SEQ ID NO: 21) |
| SFTPB | Forward Primer | 5'-GTCATCGACTACTTCCAGAACC (SEQ ID NO: 22) |
|  | Reverse Primer | 5'-AGGTGCATACAGATGCCG (SEQ ID NO: 23) |
|  | Probe | 5'-CGCCGAGGCAGACTGACTCA/3C6/ (SEQ ID NO: 24) |
| XAGE1D | Forward Primer | 5'-CCCAGGTGCTGGGAAGG (SEQ ID NO: 25) |
|  | Reverse Primer | 5'-ACTGATGCAGCTCTTGCAGA (SEQ ID NO: 26) |
|  | Probe | 5'-CCACGGACGGGAAATGCGCGA/3C6/ (SEQ ID NO: 27) |

FIG. 3 shows exemplary standard curves for LRG-1 RNA at dilutions A-E, i.e., 10 to 100,000 copies per reaction of input RNA, in the RT-QuARTS assay as described above. The average number of RNA strands present as calculated from the fluorescence signal during amplification are shown under "Calc. Strands/Rxn" on the right half of panel A. The graph in panel C shows the fluorescence signal accumulation by cycle number for the reactions having the different indicated amounts of input RNA.

RT-QuARTs Quantitative Data Analysis for Marker Detection

Strand values for individual markers from the samples were determined by using the standard curves for each marker, as discussed above for the LRG-1 RNA. The strand numbers were divided by the CASC3 reference marker strand numbers determined in the same assay well to normalize for varying input RNA amounts. The resulting ratio was multiplied by 100 to generate the "% MARKER" value for each mRNA as shown in FIG. 4.

Receiver operating characteristic (ROC) curves were generated for different groupings of markers using JMP 11.0 software (SAS). The positive percent agreement (diagnostic sensitivity) was calculated by dividing the detected positives by the known lung cancer samples and multiplying by 100, and the negative percent agreement (diagnostic specificity) by dividing the detected negatives by the known normal controls and multiplying by 100.

Figure 4:
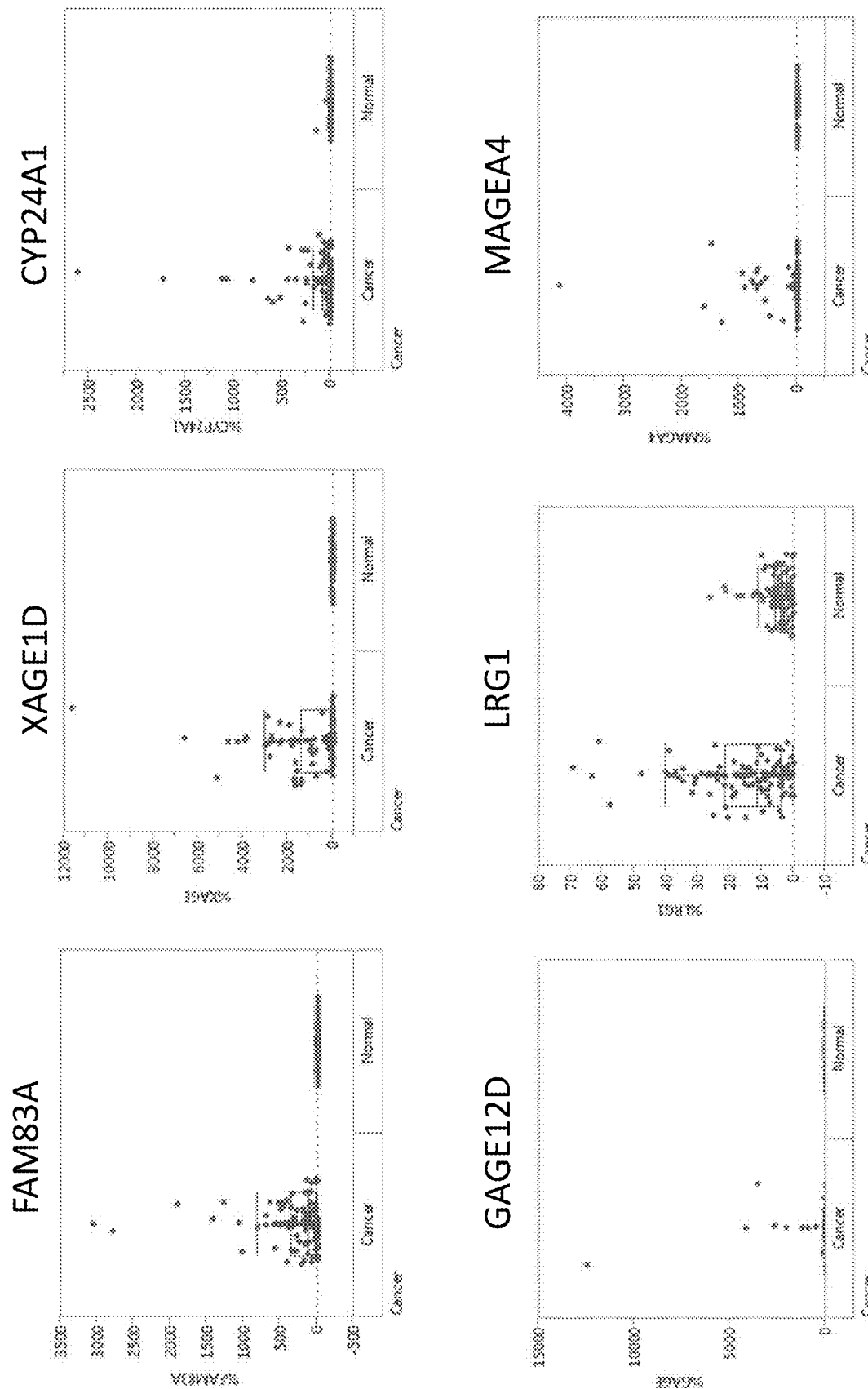
FIG. 4 compares the signals measured for markers FAM83A, XAGE1D, CYP24A1, GAGE12D, LRG1, and MAGEA4 in cancer and normal tissue samples, as described below.

FIG. 4 shows the signal measured from individual marker RNAs from cancer and normal samples. FIG. 5 shows the aggregate sensitivity and specificity for samples analyzed using the indicated combinations of mRNA markers.

Target mRNA sequences (showing T nucleotides in place of U nucleotides) are as follows:

```
AKAP4
>gi|21493038|ref|NM_139289.1
Homo sapiens A kinase (PRKA)
anchor protein 4 (AKAP4),
transcript variant 2, mRNA
                                  (SEQ ID NO: 28)
CAGGGGTGGCAGCCAACTGCAGGTGCCCAAGAACTTGGCACTTCT

CAGTTCCATCTAAAGGGGCACATCTCCCTTCTGGGTGTCACGTTT

TCAGCCAAACATCTAAAAGAACTTCATCATCAAGATGTCTGATGA

TATTGACTGGTTACGCAGCCACAGGGGTGTGTGCAAGGTAGATCT

CTACAACCCAGAAGGACAGCAAGATCAGGACCGGAAAGTGATATG

CTTTGTCGATGTGTCCACCCTGAATGTAGAAGATAAAGATTACAA

GGATGCTGCTAGTTCCAGCTCAGAAGGCAACTTAAACCTGGGAAG

TCTGGAAGAAAAGAGATTATCGTGATCAAGGAGACTGAGAAGAA

AGACGAGTCTAAGACAGAGGGATCTGTATGCCTTTTCAAACAAGC

TCCCTCTGATCCTGTAAGTGTCCTCAACTGGCTTCTCAGTGATCT

CCAGAAGTATGCCTTGGGTTTCCAACATGCACTGAGCCCCTCAAC

CTCTACCTGTAAACATAAAGTAGGAGACACAGAGGGCGAATATCA

CAGAGCATCCTCTGAGAACTGCTACAGTGTCTATGCCGATCAAGT

GAACATAGATTATTTGATGAACAGACCTCAAAACCTACGTCTAGA

AATGACAGCAGCTAAAAACACCAACAATAATCAAAGTCCTTCAGC

TCCTCCAGCCAAACCTCCTAGCACTCAGAGAGCAGTCATTTCCCC

TGATGGAGAATGTTCTATAGATGACCTTTCCTTCTACGTCAACCG

ACTATCTTCTCTGGTAATCCAGATGGCCCATAAGGAAATCAAGGA

GAAGTTGGAAGGTAAAAGCAAATGCCTTCATCATTCAATCTGTCC

ATCCCCTGGGAACAAAGAGAGAATCAGTCCCCGAACTCCTGCGAG

CAAGATTGCTTCTGAAATGGCCTATGAAGCTGTGGAACTGACAGC

TGCAGAAATGCGTGGCACTGGAGAGGAGTCCAGGGAAGGTGGCCA

GAAAAGCTTTCTATATAGCGAATTATCCAACAAGAGCAAAAGTGG

AGACAAACAGATGTCCCAGAGAGAGAGCAAAGAATTTGCAGATTC

CATCAGCAAGGGGCTCATGGTTTATGCAAATCAGGTGGCATCTGA

CATGATGGTCTCTCTCATGAAGACCTTGAAAGTGCACAGCTCTGG

GAAGCCAATTCCAGCATCTGTGGTCCTGAAGAGGGTGTTGCTAAG

GCACACCAAGGAGATTGTGTCCGATTTGATTGATTCTTGCATGAA

GAACCTGCATAATATTACTGGGGTCCTGATGACTGACTCAGACTT

TGTCTCAGCTGTCAAGAGAAATCTGTTCAACCAGTGGAAACAAAA

TGCTACAGACATCATGGAGGCCATGCTGAAGCGCTTGGTCAGTGC

CCTTATAGGTGAGGAGAAGGAGACTAAGTCTCAGAGTCTGTCATA

TGCATCTTTAAAAGCTGGGTCCCATGATCCCAAATGCAGGAATCA

GAGTCTTGAATTCTCCACCATGAAAGCTGAAATGAAAGAGAGGGA

GAAAGGCAAAATGAAATCAGACCCATGCAAGTCACTGACTAGTGC

TGAGAAAGTCGGTGAACACATTCTCAAAGAGGGCCTAACCATCTG

GAACCAAAAGCAAGGAAACTCATGCAAGGTGGCTACCAAAGCATG

CAGCAATAAAGATGAGAAAGGAGAAAAGATCAATGCTTCCACAGA

TTCACTGGCCAAGGACCTGATTGTCTCTGCCCTTAAGCTGATCCA

GTACCATCTGACCCAGCAGACTAAGGGCAAAGATACATGTGAAGA

AGACTGTCCTGGTTCCACCATGGGCTATATGGCTCAGAGTACTCA

ATATGAAAAGTGTGGAGGTGGCCAAAGTGCCAAAGCACTTTCAGT

GAAACAACTAGAATCTCACAGAGCCCCTGGACCATCCACCTGTCA

AAAGGAGAACCAACACCTGGACTCCCAGAAAATGGATATGTCAAA

CATCGTTCTAATGCTGATTCAGAAACTGCTTAATGAGAACCCCTT

CAAATGTGAGGATCCATGCGAAGGTGAGAACAAGTGTTCTGAGCC

CAGGGCAAGCAAAGCAGCTTCCATGTCCAACAGATCTGACAAAGC

GGAAGAACAATGCCAGGAGCATCAAGAACTTGACTGTACCAGTGG

GATGAAGCAAGCGAACGGGCAATTTATAGATAAACTAGTAGAATC

TGTGATGAAGCTCTGCCTTATCATGGCTAAGTATAGCAACGATGG

GGCAGCCCTTGCTGAGTTGGAAGAACAAGCAGCCTCGGCAAATAA

GCCCAATTTCAGGGGCACCAGATGCATTCACAGTGGTGCAATGCC

ACAGAACTATCAAGACTCTCTTGGACATGAAGTAATTGTCAATAA

TCAGTGCTCTACAAATAGCTTGCAGAAGCAGCTCCAGGCTGTCCT

GCAGTGGATTGCAGCCTCCCAGTTTAACGTGCCCATGCTCTACTT

CATGGGAGATAAGGATGGACAACTGGAAAAGCTTCCTCAGGTTTC

AGCTAAAGCAGCAGAGAAGGGGTACAGTGTAGGAGGTCTTCTTCA

AGAGGTCATGAAGTTTGCCAAGGAACGGCAACCAGATGAAGCTGT

GGGAAAGGTGGCCAGGAAACAGTTGCTGGACTGGCTGCTCGCTAA

CCTGTGAGCTGATCCTTGACTCCTCTTCATCTTAGCCCCCCTAGC

AGCATTCCATCCCAGCCAGAGCACCCCCACCATCAGGCCAGTCAA
```

-continued

CTGCACAATACACAACTGTATTTCCCAATACACTTGAGCAGTTGC

CTGTGAATGTAAGAGGTGTCAACAAACTGGGAAATAAAATAAAAA

AAAATAATAAAAAAAAAAAAAAAAAAAAAAAA

CASC3
>gi|102468569|ref|NM_007359.4|
Homo sapiens cancer
susceptibility candidate 3
(CASC3), mRNA (SEQ ID NO: 29)
AATCCGGGTCGGCCGCAAACGTGCCGCAGGCCTAGGCCCCGCCCA

GTGCCCCGCCCCTCCCCAACACACACACACACACACACACACAC

ACACACCCCAACACACACACACACACCCCAACACACACACACACA

CACACACACACACACACACACACACACACACACACACACACAGCG

GGATGGCCGAGCGCCGCACGCGTAGCACGCCGGGACTAGCTATCC

AGCCTCCCAGCAGCCTCTGCGACGGGCGCGGTGCGTAAGTACCTC

GCCGGTGGTGGCCGTTCTCCGTAAGATGGCGGACCGGCGGCGGCA

GCGCGCTTCGCAAGACACCGAGGACGAGGAATCTGGTGCTTCGGG

CTCCGACAGCGGCGGCTCCCCGTTGCGGGGAGGCGGGAGCTGCAG

CGGTAGCGCCGGAGGCGGCGGCAGCGGCTCTCTGCCTTCACAGCG

CGGAGGCCGAACCGGGGCCCTTCATCTGCGGCGGGTGGAGAGCGG

GGGCGCCAAGAGTGCTGAGGAGTCGGAGTGTGAGAGTGAAGATGG

CATTGAAGGTGATGCTGTTCTCTCGGATTATGAAAGTGCAGAAGA

CTCGGAAGGTGAAGAAGGTGAATACAGTGAAGAGGAAAACTCCAA

AGTGGAGCTGAAATCAGAAGCTAATGATGCTGTTAATTCTTCAAC

AAAAGAAGAGAAGGGAGAAGAAAAGCCTGACACCAAAAGCACTGT

GACTGGAGAGAGGCAAAGTGGGGACGGACAGGAGAGCACAGAGCC

TGTGGAGAACAAAGTGGGTAAAAAGGGCCCTAAGCATTTGGATGA

TGATGAAGATCGGAAGAATCCAGCATACATACCTCGGAAAGGGCT

CTTCTTTGAGCATGATCTTCGAGGGCAAACTCAGGAGGAGGAAGT

CAGACCCAAGGGGCGTCAGCGAAAGCTATGGAAGGATGAGGGTCG

CTGGGAGCATGACAAGTTCCGGGAAGATGAGCAGGCCCCAAAGTC

CCGACAGGAGCTCATTGCTCTTTATGGTTATGACATTCGCTCAGC

TCATAATCCTGATGACATCAAACCTCGAAGAATCCGGAAACCCCG

ATATGGGAGTCCTCCACAAAGAGATCCAAACTGGAACGGTGAGCG

GCTAAACAAGTCTCATCGCCACCAGGGTCTTGGGGGCACCCTACC

ACCAAGGACATTTATTAACAGGAATGCTGCAGGTACCGGCCGTAT

GTCTGCACCCAGGAATTATTCTCGATCTGGGGGCTTCAAGGAAGG

TCGTGCTGGTTTTAGGCCTGTGGAAGCTGGTGGGCAGCATGGTGG

CCGGTCTGGTGAGACTGTTAAGCATGAGATTAGTTACCGGTCACG

GCGCCTAGAGCAGACTTCTGTGAGGGATCCATCTCCAGAAGCAGA

TGCTCCAGTGCTTGGCAGTCCTGAGAAGGAAGAGGCAGCCTCAGA

GCCACCAGCTGCTGCTCCTGATGCTGCACCACCACCCCCTGATAG

GCCCATTGAGAAGAAATCCTATTCCCGGGCAAGAAGAACTCGAAC

CAAAGTTGGAGATGCAGTCAAGCTTGCAGAGGAGGTGCCCCCTCC

TCCTGAAGGACTGATTCCAGCACCTCCAGTCCCAGAAACCACCCC

AACTCCACCTACTAAGACTGGGACCTGGGAAGCTCCGGTGGATTC

TAGTACAAGTGGACTTGAGCAAGATGTGGCACAACTAAATATAGC

AGAACAGAATTGGAGTCCGGGGCAGCCTTCTTTCCTGCAACCACG

GGAACTTCGAGGTATGCCCAACCATATACACATGGGAGCAGGACC

TCCACCTCAGTTTAACCGGATGGAAGAAATGGGTGTCCAGGGTGG

TCGAGCCAAACGCTATTCATCCCAGCGGCAAAGACCTGTGCCAGA

GCCCCCCGCCCCTCCAGTGCATATCAGTATCATGGAGGGACATTA

CTATGATCCACTGCAGTTCCAGGGACCAATCTATACCCATGGTGA

CAGCCCTGCCCCGCTGCCTCCACAGGGCATGCTTGTGCAGCCAGG

AATGAACCTTCCCCACCCCAGGTTTACATCCCCACCAGACACCAGC

TCCTCTGCCCAATCCAGGCCTCTATCCCCCACCAGTGTCCATGTC

TCCAGGACAGCCACCACCTCAGCAGTTGCTTGCTCCTACTTACTT

TTCTGCTCCAGGCGTCATGAACTTTGGTAATCCCAGTTACCCTTA

TGCTCCAGGGGCACTGCCTCCCCCACCACCGCCTCATCTGTATCC

TAATACACAGGCCCCATCACAGGTATATGGAGGAGTGACCTACTA

TAACCCCGCCCAGCAGCAGGTGCAGCCAAAGCCCTCCCCACCCCG

GAGGACTCCCCAGCCAGTCACCATCAAGCCCCCTCCACCTGAGGT

TGTAAGCAGGGGTTCCAGTTAATACAAGTTTCTGAATATTTTAAA

TCTTAACATCATATAAAAAGCAGCAGAGGTGAGAACTCAGAAGAG

AAATACAGCTGGCTATCTAGTACCAGAAGGGCTTCAAAGATATAG

GGTGTGGCTCCTACCAGCAAACAGCTGAAAGAGGAGGACCCCTGC

CTTCCTCTGAGGACAGGCTCTAGAGAGAGGGAGAAACAAGTGGAC

CTCGTCCCATCTTCACTCTTCACTTGAGTTGGCTGTGTTCGGGGG

AGCAGAGAGAGCCAGACAGCCCCAAGCTTCTGAGTCTAGATACAG

AAGCCCATGTCTTCTGCTGTTCTTCACTTCGGGAAATTGAAGTG

TCTTCTGTTCCCAAGGAAGCTCCTTCCTGTTTGTTTTGTTTTCTA

AGATGTTCATTTTTAAAGCCTGGCTTCTTATCCTTAATATTATTT

TAATTTTTTCTCTTTGTTTCTGTTTCTTGCTCTCTCTCCCTGCCT

TTAAATGAAACAAGTCTAGTCTTCTGGTTTTCTAGCCCCTCTGGA

TTCCCTTTTGACTCTTCCGTGCATCCCAGATAATGGAGAATGTAT

CAGCCAGCCTTCCCCACCAAGTCTAAAAGACCTGGCCTTTCACT

TTTAGTTGGCATTTGTTATCCTCTTGTATACTTGTATTCCCTTAA

CTCTAACCCTGTGGAAGCATGGCTGTCTGCACAGAGGGTCCCATT

GTGCAGAAAAGCTCAGAGTAGGTGGGTAGGAGCCCTTCTCTTTGA

CTTAGGTTTTAGGAGTCTGAGCATCCATCAATACCTGTACTATG

ATGGGCTTCTGTTCTCTGCTGAGGGCCAATACCCTACTGTGGGA

GAGATGGCACACCAGATGCTTTTGTGAGAAAGGGATGGTGGAGTG

AGAGCCTTTGCCTTTAGGGGTGTGTATTCACATAGTCCTCAGGGC

TCAGTCTTTTGAGGTAAGTGGAATTAGAGGGCCTTGCTTCTCTTC

```
TTTCCATTCTTCTTGCTACACCCCTTTTCCAGTTGCTGTGGACCA

ATGCATCTCTTTAAAGGCAAATATTATCCAGCAAGCAGTCTACCC

TGTCCTTTGCAATTGCTCTTCTCCACGTCTTTCCTGCTACAAGTG

TTTTAGATGTTACTACCTTATTTTCCCCGAATTCTATTTTTGTCC

TTGCAGACAGAATATAAAAACTCCTGGGCTTAAGGCCTAAGGAAG

CCAGTCACCTTCTGGGCAAGGGCTCCTATCTTTCCTCCCTATCCA

TGGCACTAAACCACTTCTCTGCTGCCTCTGTGGAAGAGATTCCTA

TTACTGCAGTACATACGTCTGCCAGGGGTAACCTGGCCACTGTCC

CTGTCCTTCTACAGAACCTGAGGGCAAAGATGGTGGCTGTGTCTC

TCCCCGGTAATGTCACTGTTTTTATTCCTTCCATCTAGCAGCTGG

CCTAATCACTCTGAGTCACAGGTGTGGGATGGAGAGTGGGAGAG

GCACTTAATCTGTAACCCCCAAGGAGGAAATAACTAAGAGATTCT

TCTAGGGGTAGCTGGTGGTTGTGCCTTTTGTAGGCTGTTCCCTTT

GCCTTAAACCTGAAGATGTCTCCTCAAGCCTGTGGGCAGCATGCC

CAGATTCCCAGACCTTAAGACACTGTGAGAGTTGTCTCTGTTGGT

CCACTGTGTTTAGTTGCAAGGATTTTTCCATGTGTGGTGGTGTTT

TTTGTTACTGTTTTAAAGGGTGCCCATTTGTGATCAGCATTGTGA

CTTGGAGATAATAAAATTTAGAGTATAAACTTGGCTCCCTAAAAA

AAAAAAAAAAAAA

CYP24A1
>gi|193083115|ref|NM_000782.4|
Homo sapiens cytochrome P450,
family 24, subfamily A, polypeptide 1
(CYP24A1), transcript
variant 1, mRNA
                                  (SEQ ID NO: 30)
GACAGGAGGAAACGCAGCGCCAGCAGCATCTCATCTACCCTCCTT

GACACCTCCCCGTGGCTCCAGCCAGACCCTAGAGGTCAGCCTTGC

GGACCAACAGGAGGACTCCCAGCTTTCCCTTTTCAAGAGGTCCCC

AGACACCGGCCACCCTCTTCCAGCCCCTGCGGCCAGTGCAAGGAG

GCACCAATGCTCTGAGGCTGTCGCGTGGTGCAGCGTCGAGCATCC

TCGCCGAGGTCCTTTCTGCTGCCTGTCCCGCCTCACCCCGCTCCA

TCACACCAGCTGGCCCTCTTTGCTTCCTTTTCCCAGAATCGTTAA

GCCCCGACTCCCACTAGCACCTCGTACCAACCTCGCCCCACCCCA

TCCTCCTGCCTTCCCGCGCTCCGGTGTCCCCCGCTGCCATGAGCT

CCCCCATCAGCAAGAGCCGCTCGCTTGCCGCCTTCCTGCAGCAGC

TGCGCAGTCCGAGGCAGCCCCCGAGACTGGTGACATCTACGGCGT

ACACGTCCCCTCAGCCGCGAGAGGTGCCAGTCTGCCCGCTGACAG

CTGGTGGCGAGACTCAGAACGCGGCCGCCCTGCCGGGCCCCACCA

GCTGGCCACTGCTGGGCAGCCTGCTGCAGATTCTCTGGAAAGGGG

GTCTCAAGAAACAGCACGACACCCTGGTGGAGTACCACAAGAAGT

ATGGCAAGATTTTCCGCATGAAGTTGGGTTCCTTTGAGTCGGTGC

ACCTGGGCTCGCCATGCCTGCTGGAAGCGCTGTACCGCACCGAGA

GCGCGTACCCGCAGCGGCTGGAGATCAAACCGTGGAAGGCCTATC

GCGACTACCGCAAAGAAGGCTACGGGCTGCTGATCCTGGAAGGGG

AAGACTGGCAGCGGGTCCGGAGTGCCTTTCAAAAGAAACTAATGA

AACCAGGGGAAGTGATGAAGCTGGACAACAAAATCAATGAGGTCT

TGGCCGATTTTATGGGCAGAATAGATGAGCTCTGTGATGAAAGAG

GCCACGTTGAAGACTTGTACAGCGAACTGAACAAATGGTCGTTTG

AAAGTATCTGCCTCGTGTTGTATGAGAAGAGATTTGGGCTTCTCC

AGAAGAATGCAGGGGATGAAGCTGTGAACTTCATCATGGCCATCA

AAACAATGATGAGCACGTTTGGGAGGATGATGGTCACTCCAGTCG

AGCTGCACAAGAGCCTCAACACCAAGGTCTGGCAGGACCACACTC

TGGCCTGGGACACCATTTTCAAATCAGTCAAAGCTTGTATCGACA

ACCGGTTAGAGAAGTATTCTCAGCAGCCTAGTGCAGATTTCCTTT

GTGACATTTATCACCAGAATCGGCTTTCAAAGAAAGAATTGTATG

CTGCTGTCACAGAGCTCCAGCTGGCTGCGGTGGAAACGACAGCAA

ACAGTCTAATGTGGATTCTCTACAATTTATCCCGTAATCCCCAAG

TGCAACAAAAGCTTCTTAAGGAAATTCAAAGTGTATTACCTGAGA

ATCAGGTGCCACGGGCAGAAGATTTGAGGAATATGCCGTATTTAA

AAGCCTGTCTGAAAGAATCTATGAGGCTTACGCCGAGTGTACCAT

TTACAACTCGGACTCTTGACAAGGCAACAGTTCTGGGTGAATATG

CTTTACCCAAAGGAACAGTGCTCATGCTAAATACCCAGGTGTTGG

GATCCAGTGAAGACAATTTTGAAGATTCAAGTCAGTTTAGACCTG

AACGTTGGCTTCAGGAGAAGGAAAAAATTAATCCTTTTGCGCATC

TTCCATTTGGCGTTGGAAAAAGAATGTGCATTGGTCGCCGATTAG

CAGAGCTTCAACTGCATTTGGCTCTTTGTTGGATTGTCCGCAAAT

ACGACATCCAGGCCACAGACAATGAGCCTGTTGAGATGCTACACT

CAGGCACCCTGGTGCCCAGCCGGGAACTCCCCATCGCGTTTTGCC

AGCGATAATACGCCTCAGATGGTGGTATTTGCTAACATCATATCC

AACTCAGGGAAGCGGACTGAGTGCTGGGATCCAAGGCATTCTACA

GGGTTCACTGCTGGTTTACACTTCACCTGTGTCAGCACCATCTTC

AGGTGCTTAGAATGGCCTGGGAGCCTGTTCGTCTTGCATCTTCC

ATGACATGAAAGGGAGGCTGGCACTTGTCAGTCAGGTAGAGGTTA

CAAACCGTTTCAGGCCCTGCCTACCACATTCACTGTTTGAATCTT

TAATTCCCAAGAATAAGTTTAGATTTCACAATGAATGACCTACAA

CAGCTAAATTTTCTGGGGCTGGGAGTAATACTGACAATCCATTTA

CTGTAGCTCTGCTTAATGTACTACTTAGGAAAATGTCCCTGCTTA

ATAATGTAAGCCAAGCTAAATGATGGTTAAAGTTATCAGGCCTCC

CATGAAATTGCGTTCTTCCTGCATTGAAATAAAAACATTATTGGG

AAACTAGAGAACACCTCTATTTTTAAAAGGACTTTAACGAAGTCA

AACAACTTATAAGACTAGTGATTCACTGGGGCATTATTTTGTTAG

AGGACCTTAAAATTGTTTATTTTTAAATGTGATTCCTTTATGGC

ATTAGGGTAAAGATGAAGCAATAATTTTTAAATTGTGTATGTGCA
```

-continued
TATGAAGCACAGACATGCATGTGTGTGTGTCTGTGTGTGTG
TCCGTGTATGTGTGTGGGTTCTAATGGTAATTTGCCTCAGTCA
TTTTTTTAATATTTGCAGTACTTGATTTAGGATCTGTGGTGCAGG
GCAATGTTTCAAAGTTTAGTCACAGCTTAAAAACATTCAGTGTGA
CTTTAATATTATAAAATGATTTCCCATGCCATAATTTTTCTGTCT
ATTAAATGGGACAAGTGTAAAGCATGCAAAAGTTAGAGATCTGTT
ATATAACATTTGTTTTGTGATTTGAACTCCTAGGAAAAATATGAT
TTCATAAATGTAAAATGCACAGAAATGCATGCAATACTTATAAGA
CTTAAAAATTGTGTTTACAGATGGTTTATTTGTGCATATTTTTAC
TACTGCTTTTCCTAAATGCATACTGTATATAATTCTGTGTATTTG
ATAAATATTTCTTCCTACATTATATTTTTAGAATATTTCAGAAAT
ATACATTTATGTCTTTATATTGTAATAAATATGTACATATCTAGG
TATATGCTTTCTCTCTGCTGTGAAATTATTTTTAGAATTATAAAT
TCACGTCTTGTCAGATTTCATCTGTATACCTTCAAATTCTCTGAA
AGTAAAAATAAAAGTTTTTAAATATTAAAAAAAAAAAAAAAAAA
AA FAM83A
>gi|767953716|ref|XM_005251087.2|
PREDICTED: Homo sapiens family
with sequence similarity 83, member A
(FAM83A), transcript
variant X1, mRNA
(SEQ ID NO: 31)
AGGAAATATCCCATGGCTGACTGTGCCAAGGAGGTGTCTGAGCCA
GCCCTCCCGGCCCGAGGGCAGGGCAGGTGGCCCTGAGAGATAAGC
CAATCCCGCAGCTGCAGATGAGGAGTTCTGAGAAGCATTGCTCAG
GACAGCGGTAAATCACTTCTTGGAGGTGCCCTGCACGCCGGTCCT
GGGAGCAGGCGGCCTCCCGGGGGTGCGGGAGCCCCACTCCTCCGT
GGTGTGTTCCATTTGCTTCCCACATCTGGAGGAGCTGACGTGCCA
GCCTCCCCCAGCACCACCCAGGGACGGGAGGCATGAGCCGGTCAA
GGCACCTGGGCAAAATCCGGAAGCGTCTGGAAGATGTCAAGAGCC
AGTGGGTCCGGCCAGCCAGGGCTGACTTTAGTGACAACGAGAGTG
CCCGGCTGGCCACGGACGCCCTCTTGGATGGGGGTTCTGAAGCCT
ACTGGCGGGTGCTCAGCCAGGAAGGCGAGGTGGACTTCTTGTCCT
CGGTGGAGGCCCAGTACATCCAGGCCCAGGCTCAGGGAGCCCCGT
GTCCCCCAGACACCCTGGGAGGGGCGGAAGCAGGCCCTAAGGGAC
TGGACTCCAGCTCCCTACAGTCCGGCACCTACTTCCCTGTGGCCT
CAGAGGGCAGCGAGCCGGCCCTACTGCACAGCTGGGCCTCAGCTG
AGAAGCCCTACCTGAAGGAAAAATCCAGCGCCACTGTGTACTTCC
AGACCGTCAAGCACAACAACATCAGAGACCTCGTCCGCCGCTGCA
TCACCCGGACTAGCCAGAACATTTCCATCCGGAGTGTGGAAGGAG
AGATATACTGTGCCAAGTCAGGCAGGAAATTCGCTGGCCAAATCC
GGGAGAAGTTCATCATCTCGGACTGGAGATTTGTCCTGTCTGGAT
CTTACAGCTTCACCTGGCTCTGCGGACACGTGCACCGGAACATCC -continued
TCTCCAAGTTCACAGGCCAGGCGGTGGAGCTGTTTGACGAGGAGT
TCCGCCACCTCTACGCCTCCTCCAAGCTGTGATGGGCCTGAAGT
CCCCGCGGCTGGTCGCCCCCGTCCCGCCCGGAGCAGCCCCGGCCA
ATGGCCGCCTTAGCAGCAGCAGTGGCTCCGCCAGTGACCGCACGT
CCTCCAACCCCTTCAGCGGCCGCTCGGCAGGCAGCCACCCCGGTA
CCCGAAGTGTGTCCGCGTCTTCAGGGCCCTGTAGCCCCGCGGCCC
CACACCCGCCTCCACCGCCCCGGTTCCAGCCCCACCAAGGCCCTT
GGGGAGCCCCGAGTCCCCAGGCCCACCTCTCCCCGCGGCCCCACG
ACGGCCCGCCCGCCGCTGTCTACAGCAACCTGGGGGCCTACAGGC
CCACGCGGCTGCAGCTGGAGCAGCTGGGCCTGGTGCCGAGGCTGA
CTCCAACCTGGAGGCCCTTCCTGCAGGCCTCCCCTCACTTCTGAA
GGTCCCATCCCTGCTGCCCTCCGCAGGCCCAGGGCTGGGCACTC
CCTGAGACCCAAAGACCCACCTCAACGACGAGTGGCGTTGAGCCA
CTTCCCTTTGAAAAGACACTCAAAATCACTGCCATGGTTCAATGT
TCCCAGGCCCCAGGCCATCCACTTGCCGGCCCCCACCAGTTCTTG
GGTTCCCCGCTCTAGTTTGACCTGTGCAGCACATTCCAGAAGGTT
CCAGGGAGGTTGTGGGGCAGCTAGAGGACAAAATCATGAAAACAG
AGTCCCTGTCTTCCAGAGATCATCCGGGGCTTTAATATTAATGGC
CCCCAAAACTCCGTAAGAAGCAGGAAATGCAGCCCAAGTTTTACA
AATGGGTAAACAGAGGCACTGAGAGATAGATGGTAGTTTGGTACT
TCTGGTTCCCAGTGCCCAGGAATGGTCCACTCCCAAGAAATTCAG
GAAAGAAAGACTGAGGAGAAGGTGTGGGAACATTCTGGATGTTTC
GGGAGAGTTGGGGAAACTCCTCCTCTTAGGAAAGGCTAATACTAG
GGTATCCTTGGGCCCAATGAATTAGGGGTGAGGCCCCAGAACCCG
TTATCTATGAGTTGTATGGGGGAGCCATCTGAAGCTGTAGCCACC
AGGGATGCAGCTAGCTGAGGAGTTTGGGGTGTTGGGTTGGACAAG
GCAGGTTAGTAGACTCAGATTCTTGCTTCAAAGAGCCTTGGGCTG
GCCTGGAGGTCCCTGGAGTCTAGACTGGACCTAGGAGCTTGAGTT
GTCAGGGGCCAGGACTGGCCCCACTGCAGTGCCCAGGCCAGTCTT
GAGCAGCAGGGAGGGCTCAGCTGTCCCCAGATCCAGGTGCCTCTG
ACCAGCCTGGTCACCTCCTGAGGAATAAATGCTGAACCTCACAAG
CCCCATCATTCATTTCTTCTCAATTCACAGTGCCCCTCTTTGTTT
CTGGGGTGGAACTAGGTCCTGAGGGCACAGCCTAGCTGAGTGCAA
AGAAATATAGGATGCTTAGAAAGCATACAGGAGGGGCCAGGCGTG
GTGGCTCATGCCTGTAATCCCAGAACTTTGGGATGCCAAGGTGGT
TGGATTACCTGAGATCAGGTGGATTACCTGGTCTCGAGACCAGCC
TGACCAATATGGTGAAACCCCGTCTCTACTAAAAATACAAAAATT
AGGCTGAGACAGGAGAATTGCTTGAACCCAGGAAGCAGAGGTTGC
AATGAGCTGAGATTGCATCACTGCACTCCAGCATGGGCAACAAAG
CAAGACTCCGTCACAGAAAAAAAAAAAAAAAGAGAGAGAGCATA
GAGGAGGGTTGGCCAGCCCTGTGGTGGGTGGGATGTCAGAGACAC

```
TTCCCAGATAAAGTAAGAGTTAACCCTGCACCTCAGGTGTGATAG

TGGGGTCAGTGGTATGTGATCCAGGCTGGGGAGCCAGAGGGGAGC

AGGTGCCAACTCCACATCCTTCTCCTGTTTCTAGGCCCTCTCCTC

CCTTGTCGGTTTTTGGCGGGGAAGCTCAGCCTTCGCTGTGGAGGG

ACGAGAGCACAGAGCTCTTCCTCCTGGTGGCCTCTGACCCCTGAC

GGCCTGTGGCATCCTCCCTAGTCCCCTCTGCCCATCCATCCCTCT

GTTCCAATTCTCCACTGCTCCCAGCATGATCTGGGGCATCTTGGC

TTCTGGTTTCTTTTATTATTATTATTATTAATTATTGTATTC

CTGTCCTTCACTTTTTTCCTCCTTAGTTCCTGAAAGTAAACAAAA

CAAAACAAAAACAAAAAAACAAACAACACTTTGGTTCCTGATGGC

TTTCTGAACCCAGCCCTGAGCTTGTTGTTTCACAGCTGACGGCTG

AGATGAGGTTAGAATGACTGGGCCCGGCTGAACATTCCAAATTGG

ATTTCACCATCTGCTGAGAAAGTTTAAGGAAGGCAAAGCTTGCCA

GGTCACAGAAGCTCCCAAGCCCAGCTTTCCAAAGGCCTCAGCCTG

TGCCTGTGTCGAGCTCAGTCCTGGGAGATAGGGGAGAACCTGCAG

GCAGGAACAAGCCCCCTACTCCTGACCACCCTCCATCAGCAGTC

TCCCCTCCGTGGTCGTCTTTGTTGACAAAGGTGCAGTTTCTCCTC

TCCTGGGCACCTGTAACATGTGATGCGCTGCCTGCTGGGAGGTTA

GGTCGGGGCTGCCCCGGCGAGTGGAGCATGAGCAGAACCGCCGAG

GGTCACTTCTGGGCAGAAGCTTTGAGAGCCTGGGTCCAGGTTGCC

ACATAGAAGCAGCTCTCCAGTTGAAACCCTCCTCTGCCAGCCTGG

GGTCCTAAGCGATGAGCAGAATCCCCCACTCCCACCCCACCAACC

CACAATGGATATGTAGTGAGCAAGAAATAAACCTTTGTTGTTTAA

GCCA

GAGE12D
gi|187608822|ref|NM_001127199.1|
Homo sapiens G antigen 12D
(GAGE12D), mRNA
                               (SEQ ID NO: 32)
GTTCACTGGGCGTCTTCTGCCCGGCCCCTTCGCCCACGTGAAGAA

CGCCAGGGAGCTGTGAGGCAGTGCTGTGTGGTTCCTGCCGTCCGG

ACTCTTTTTCCTCTACTGAGATTCATCTGTGTGAAATATGAGTTG

GCGAGGAAGATCGACCTATTATTGGCCTAGACCAAGGCGCTATGT

ACAGCCTCCTGAAATGATTGGGCCTATGCGGCCCGAGCAGTTCAG

TGATGAAGTGGAACCAGCAACACCTGAAGAAGGGGAACCAGCAAC

TCAATGTCAGGATCCTGCAGCTGCTCAGGAGGGAGAGGATGAGGG

AGCATCTGCAGGTCAAGGGCCGAAGCCTGAAGCTCATAGCCAGGA

ACAGGGTCACCCACAGACTGGGTGTGAGTGTGAAGATGGTCCTGA

TGGGCAGGAGATGGACCCGCCAAATCCAGAGGAGGTGAAAACGCC

TGAAGAAGGTGAAAAGCAATCACAGTGTTAAAAGAAGACACGTTG
```

```
AAATGATGCAGGCTGCTCCTATGTTGGAAATTTGTTCATTAAAAT

TCTCCCAATAAAGCTTTACAGCCTTCTGCAAAGAAGTCTTGCGCA

LRG1
gi|49574519|ref|NM_052972.2|
Homo sapiens leucine-rich alpha-2-
glycoprotein 1 (LRG1), mRNA
                               (SEQ ID NO: 33)
GCAGAGCTACCATGTCCTCTTGGAGCAGACAGCGACCAAAAAGCC

CAGGGGGCATTCAACCCCATGTTTCTAGAACTCTGTTCCTGCTGC

TGCTGTTGGCAGCCTCAGCCTGGGGGGTCACCCTGAGCCCCAAAG

ACTGCCAGGTGTTCCGCTCAGACCATGGCAGCTCCATCTCCTGTC

AACCACCTGCCGAAATCCCCGGCTACCTGCCAGCCGACACCGTGC

ACCTGGCCGTGGAATTCTTCAACCTGACCCACCTGCCAGCCAACC

TCCTCCAGGGCGCCTCTAAGCTCCAAGAATTGCACCTCTCCAGCA

ATGGGCTGGAAAGCCTCTCGCCCGAATTCCTGCGGCCAGTGCCGC

AGCTGAGGGTGCTGGATCTAACCCGAAACGCCCTGACCGGGCTGC

CCCCGGGCCTCTTCCAGGCCTCAGCCACCCTGGACACCCTGGTAT

TGAAAGAAAACCAGCTGGAGGTCCTGGAGGTCTCGTGGCTACACG

GCCTGAAAGCTCTGGGGCATCTGGACCTGTCTGGGAACCGCCTCC

GGAAACTGCCCCCCGGGCTGCTGGCCAACTTCACCCTCCTGCGCA

CCCTTGACCTGGGGGAGAACCAGTTGGAGACCTTGCCACCTGACC

TCCTGAGGGGTCCGCTGCAATTAGAACGGCTACATCTAGAAGGCA

ACAAATTGCAAGTACTGGGAAAAGATCTCCTCTTGCCGCAGCCGG

ACCTGCGCTACCTCTTCCTGAACGGCAACAAGCTGGCCAGGGTGG

CAGCCGGTGCCTTCCAGGGCCTGCGGCAGCTGGACATGCTGGACC

TCTCCAATAACTCACTGGCCAGCGTGCCCGAGGGGCTCTGGGCAT

CCCTAGGGCAGCCAAACTGGGACATGCGGGATGGCTTCGACATCT

CCGGCAACCCCTGGATCTGTGACCAGAACCTGAGCGACCTCTATC

GTTGGCTTCAGGCCCAAAAAGACAAGATGTTTTCCCAGAATGACA

CGCGCTGTGCTGGGCCTGAAGCCGTGAAGGGCCAGACGCTCCTGG

CAGTGGCCAAGTCCCAGTGAGACCAGGGGCTTGGGTTGAGGGTGG

GGGGTCTGGTAGAACACTGCAACCCGCTTAACAAATAATCCTGCC

TTTGGCCGGGTGCGGGGGCTCACGCCTGTAATCCCAGCACTTTGG

GAGGCCCAGGTGGGCGGATCACGAGGTCAGGAGATCGAGACCATC

TTGGCTAACATGGTGAAACCCTGTCTCTACTAAAAATATAAAAA

TTAGCCAGGCGTGGTGGTGGGCACCTGTAGTCCCAGCAACTCGGG

AGGCTGAGGCAGGAGAATGGCGTGAACTTGGGAGGCGGAGCTTGC

GGTGAGCCAAGATCGTGCCACTGCACTCTAGCCTGGGCGACAGAG

CAAGACTGTCTCAAAAAAATTAAAATTAAAATTAAAAACAAATAA

TCCTGCCTTTTACAGGTGAAACTCGGGGCTGTCCATAGCGGCTGG

GACCCCGTTTCATCCATCCATGCTTCCTAGAACACACGATGGGCT

TTCCTTACCCATGCCCAAGGTGTGCCCTCCGTCTGGAATGCCGTT

CCCTGTTTCCCAGATCTCTTGAACTCTGGGTTCTCCCAGCCCCTT
```

GTCCTTCCTTCCAGCTGAGCCCTGGCCACACTGGGGCTGCCTTTC

TCTGACTCTGTCTTCCCCAAGTCAGGGGGCTCTCTGAGTGCAGGG

TCTGATGCTGAGTCCCACTTAGCTTGGGGTCAGAACCAAGGGGTT

TAATAAATAACCCTTGAAAACTGGA

MAGEA4
>gi|58530866|ref|NM_001011548.1|
Homo sapiens MAGE family member
A4 (MAGEA4), transcript variant 1, mRNA
(SEQ ID NO: 34)
AGAGACAAGCGAGCTTCTGCGTCTGACTCGCAGCTTGAGACTGGC

GGAGGGAAGCCCGCCCAGGCTCTATAAGGAGACAAGGTTCTGAGC

AGACAGGCCAACCGGAGGACAGGATTCCCTGGAGGCCACAGAGGA

GCACCAAGGAGAAGATCTGCCTGTGGGTCCCCATTGCCCAGCTTT

TGCCTGCACTCTTGCCTGCTGCCCTGACCAGAGTCATCATGTCTT

CTGAGCAGAAGAGTCAGCACTGCAAGCCTGAGGAAGGCGTTGAGG

CCCAAGAAGAGGCCCTGGGCCTGGTGGGTGCACAGGCTCCTACTA

CTGAGGAGCAGGAGGCTGCTGTCTCCTCCTCCTCTCCTCTGGTCC

CTGGCACCCTGGAGGAAGTGCCTGCTGCTGAGTCAGCAGGTCCTC

CCCAGAGTCCTCAGGGAGCCTCTGCCTTACCCACTACCATCAGCT

TCACTTGCTGGAGGCAACCCAATGAGGGTTCCAGCAGCCAAGAAG

AGGAGGGGCCAAGCACCTCGCCTGACGCAGAGTCCTTGTTCCGAG

AAGCACTCAGTAACAAGGTGGATGAGTTGGCTCATTTTCTGCTCC

GCAAGTATCGAGCCAAGGAGCTGGTCACAAAGGCAGAAATGCTGG

AGAGAGTCATCAAAAATTACAAGCGCTGCTTTCCTGTGATCTTCG

GCAAAGCCTCCGAGTCCCTGAAGATGATCTTTGGCATTGACGTGA

AGGAAGTGGACCCCGCCAGCAACACCTACACCCTTGTCACCTGCC

TGGGCCTTTCCTATGATGGCCTGCTGGGTAATAATCAGATCTTTC

CCAAGACAGGCCTTCTGATAATCGTCCTGGGCACAATTGCAATGG

AGGGCGACAGCGCCTCTGAGGAGGAAATCTGGGAGGAGCTGGGTG

TGATGGGGGTGTATGATGGGAGGGAGCACACTGTCTATGGGAGC

CCAGGAAACTGCTCACCCAAGATTGGGTGCAGGAAAACTACCTGG

AGTACCGGCAGGTACCCGGCAGTAATCCTGCGCGCTATGAGTTCC

TGTGGGGTCCAAGGGCTCTGGCTGAAACCAGCTATGTGAAAGTCC

TGGAGCATGTGGTCAGGGTCAATGCAAGAGTTCGCATTGCCTACC

CATCCCTGCGTGAAGCAGCTTTGTTAGAGGAGGAAGAGGGAGTCT

GAGCATGAGTTGCAGCCAGGGCTGTGGGGAAGGGCAGGGCTGGG

CCAGTGCATCTAACAGCCCTGTGCAGCAGCTTCCCTTGCCTCGTG

TAACATGAGGCCCATTCTTCACTCTGTTTGAAGAAAATAGTCAGT

GTTCTTAGTAGTGGGTTTCTATTTTGTTGGATGACTTGGAGATTT

ATCTCTGTTTCCTTTTACAATTGTTGAAATGTTCCTTTTAATGGA

TGGTTGAATTAACTTCAGCATCCAAGTTTATGAATCGTAGTTAAC

GTATATTGCTGTTAATATAGTTTAGGAGTAAGAGTCTTGTTTTTT

ATTCAGATTGGGAAATCCGTTCTATTTTGTGAATTTGGGACATAA

TAACAGCAGTGGAGTAAGTATTTAGAAGTGTGAATTCACCGTGAA

ATAGGTGAGATAAATTAAAAGATACTTAATTCCCGCCTTATGCCT

CAGTCTATTCTGTAAAATTTAAAAAATATATATGCATACCTGGAT

TTCCTTGGCTTCGTGAATGTAAGAGAAATTAAATCTGAATAAATA

ATTCTTTCTGTTAA

SFTPB
>gi|288856298|ref|NM_000542.3|
Homo sapiens surfactant protein B
(SFTPB), transcript variant 1, mRNA
(SEQ ID NO: 35)
TGTAAATGCTCTTCTGACTAATGCAAACCATGTGTCCATAGAACC

AGAAGATTTTTCCAGGGGAAAAGAGCCCCCACGCCCCGCCCAGCT

ATAAGGGGCCATGCACCAAGCAGGGTACCCAGGCTGCAGAGGTGC

CATGGCTGAGTCACACCTGCTGCAGTGGCTGCTGCTGCTGCTGCC

CACGCTCTGTGGCCCAGGCACTGCTGCCTGGACCACCTCATCCTT

GGCCTGTGCCCAGGGCCCTGAGTTCTGGTGCCAAAGCCTGGAGCA

AGCATTGCAGTGCAGAGCCCTAGGGCATTGCCTACAGGAAGTCTG

GGGACATGTGGGAGCCGATGACCTATGCCAAGAGTGTGAGGACAT

CGTCCACATCCTTAACAAGATGGCCAAGGAGGCCATTTTCCAGGA

CACGATGAGGAAGTTCCTGGAGCAGGAGTGCAACGTCCTCCCCTT

GAAGCTGCTCATGCCCCAGTGCAACCAAGTGCTTGACGACTACTT

CCCCCTGGTCATCGACTACTTCCAGAACCAGACTGACTCAAACGG

CATCTGTATGCACCTGGGCCTGTGCAAATCCCGGCAGCCAGAGCC

AGAGCAGGAGCCAGGGATGTCAGACCCCCTGCCCAAACCTCTGCG

GGACCCTCTGCCAGACCCTCTGCTGGACAAGCTCGTCCTCCCTGT

GCTGCCCGGGGCCCTCCAGGCGAGGCCTGGGCCTCACACACAGGA

TCTCTCCGAGCAGCAATTCCCCATTCCTCTCCCCTATTGCTGGCT

CTGCAGGGCTCTGATCAAGCGGATCCAAGCCATGATTCCCAAGGG

TGCGCTAGCTGTGGCAGTGGCCCAGGTGTGCCGCGTGGTACCTCT

GGTGGCGGGCGGCATCTGCCAGTGCCTGGCTGAGCGCTACTCCGT

CATCCTGCTCGACACGCTGCTGGGCCGCATGCTGCCCCAGCTGGT

CTGCCGCCTCGTCCTCCGGTGCTCCATGGATGACAGCGCTGGCCC

AAGGTCGCCGACAGGAGAATGGCTGCCGCGAGACTCTGAGTGCCA

CCTCTGCATGTCCGTGACCACCCAGGCCGGGAACAGCAGCGAGCA

GGCCATACCACAGGCAATGCTCCAGGCCTGTGTTGGCTCCTGGCT

GGACAGGGAAAAGTGCAAGCAATTTGTGGAGCAGCACACGCCCCA

GCTGCTGACCCTGGTGCCCAGGGGCTGGGATGCCCACACCACCTG

CCAGGCCCTCGGGGTGTGTGGGACCATGTCCAGCCCTCTCCAGTG

TATCCACAGCCCCGACCTTTGATGAGAACTCAGCTGTCCAGCTGC

AAAGGAAAAGCCAAGTGAGACGGGCTCTGGGACCATGGTGACCAG

GCTCTTCCCCTGCTCCCTGGCCCTCGCCAGCTGCCAGGCTGAAAA

GAAGCCTCAGCTCCCACACCGCCCTCCTCACCGCCCTTCCTCGGC

AGTCACTTCCACTGGTGGACCACGGGCCCCCAGCCCTGTGTCGGC

```
CTTGTCTGTCTCAGCTCAACCACAGTCTGACACCAGAGCCCACTT

CCATCCTCTCTGGTGTGAGGCACAGCGAGGGCAGCATCTGGAGGA

GCTCTGCAGCCTCCACACCTACCACGACCTCCCAGGGCTGGGCTC

AGGAAAAACCAGCCACTGCTTTACAGGACAGGGGGTTGAAGCTGA

GCCCCGCCTCACACCCACCCCATGCACTCAAAGATTGGATTTTA

CAGCTACTTGCAATTCAAAATTCAGAAGAATAAAAAATGGGAACA

TACAGAACTCTAAAAGATAGACATCAGAAATTGTTAAGTTAAGCT

TTTTCAAAAAATCAGCAATTCCCCAGCGTAGTCAAGGGTGGACAC

TGCACGCTCTGGCATGATGGGATGGCGACCGGGCAAGCTTTCTTC

CTCGAGATGCTCTGCTGCTTGAGAGCTATTGCTTTGTTAAGATAT

AAAAAGGGGTTTCTTTTTGTCTTTCTGTAAGGTGGACTTCCAGCT

TTTGATTGAAAGTCCTAGGGTGATTCTATTTCTGCTGTGATTTAT

CTGCTGAAAGCTCAGCTGGGGTTGTGCAAGCTAGGGACCCATTCC

TGTGTAATACAATGTCTGCACCAATGCTAATAAAGTCCTATTCTC

TTTTATGAGAAAGAAAAAGACACCGTCCTTTAAAGTGCTGCAGTA

TGGCCAGACGTGGTGGCTCACACCTGCAATCCCAGCACCTTAGGA

GGCCGAGGCAGGAGGATCCTTGAGGTCAGGAGTTCGAGACGAGCC

TCGCCAACATGGTGAAACCCCATTTCTACTAAAAATACAAAAAAT

TAGCCAAGTGTGGTGGCATATGCCTGTAATCCCAACTACTCAGAA

GGCCGAGGCAGGAGAATTACTTGAACGCAGGAGAATCACTGCAGC

CCAGGAGGCAGAGGTTGCAGTGAGCCGAGATTGCACCACTGCACT

CCAGCCTGGGTGACAGAGCAAGACTCCATCTCAGTAAATAAATAA

ATAAATAAAAAGCGCTGCAGTAGCTGTGGCCTCACCCTGAAGTCA

GCGGGCCCAGGCCTACCTCACTCTCTCCCTTGGCAGAGAAGCAGA

CGTCCATAGCTCCTCTCCCTCACAAGCGCTCCCAGCCTGCCCTCC

AGCTGCTGCTCTCCCCTCCCAGTCTCTACTCACTGGGATGAGGTT

AGGTCATGAGGACACCAAAAACCTAAAAATAAACAAAAAGCCAAA

CAAGCCTTAGCTTTTCTTAAAGACTGAAATGCCTGGAAGTGTCCC

TTTATTTATAAAATAACTTTTGTCATATTTCTTATACATGTTTCT

TGTAAGAAATTCAGAAACTACAGACAAAGAGAGTGGAAATTACCC

ACTGTCAGGCCTCTGAGCCCAAGCTAAGCCATCATATCCCCTGTG

CCCTGCACGTATACACCCAGATGGCCTGAAGCAACTGAAGATCCA

CAAAAGAAGTGAAAATAGCCAGTTCCTGCCTTAACTGATGACATT

CCACCATTGTGATTTGTTCCTGCCCCACCCTAACTGATCAATTGA

CCTTGTGACAATACACCTTCCCCACCCTTGAGAAGGTGCTTTGTA

ATATTCTCCCACCCACCCCACGCCCGCACCCCCGCACCCTTAAG

AAGGTATTTTGTAATATTCTCTCCGCCATTGAGAATGTGCTTTGT

AAGATCCACCCCCTGCCCACAAAAAATTGCTCCTAACTCCACCGC

CTATCCCAAACCTACAAGAACTAATGATAATCCCACCACCCTTTG

CTGACTCTTTTTGGACTCAGCCCACCTGCACCCAGGTGATTAAAA
```

```
AGCTTTATTGTTCACACAAAGCCTGTTTGGTAGTCTCTTCACAGG

GAAGCATGTGACACCCACAATCCCACCTAGCCCAGGAGAGAGCTA

CGGCAGGGTGTGTGTTTTGACACTGAGCTTGGGGCTTTTTCCATC

TTCTCCCCACAGCCTCTGGCTCCACACCTCCACCGTTCAAGCGCC

AGAAAGAGCTGTCTATGCAGCCTGCTCTTGGGCCTGGGGATGAGA

CACACAATTCATTGGCTCCTGGATTTTAAGTAGACATTTGTAAAT

CTATAGCTAACTACTGTCCTTAAAGCCATTGTTTCCATTAGAAAA

TCCAACTCTCTGAGAGAAAAGGGTGTTTTAAATTTAAAAAAATAA

AAACAAAAAAGTTTGATTGAGAAAAAAAAAAAAAAA

XAGE-1d
>gi|18157207|emb|AJ318879.1|
Homo sapiens mRNA for XAGE-1d
protein
                                       (SEQ ID NO: 36)
GGGAACGCGGCGGAGCTGTGAGCCGGCGACTCGGGTCCCTGAGGT

CTGGATTCTTTCTCCGCTACTGAGACACGGCGGACACACACAAAC

ACAGAACCACACAGCCAGTCCCAGGAGCCCAGTAATGGAGAGCCC

CAAAAAGAAGAACCAGCAGCTGAAAGTCGGGATCCTACACCTGGG

CAGCAGACAGAAGAAGATCAGGATACAGCTGAGATCCCAGGTGCT

GGGAAGGGAAATGCGCGACATGGAAGGTGATCTGCAAGAGCTGCA

TCAGTCAAACACCGGGGATAAATCTGGATTTGGGTTCCGGCGTCA

AGGTGAAGATAATACCTAAAGAGGAACACTGTAAAATGCCAGAAG

CAGGTGAAGAGCAACCACAAGTTTAAATGAAGACAAGCTGAAACA

ACGCAAGCTGGTTTTATATTAGATATTTGACTTAAACTATCTCAA

TAAAGTTTTGCAGCTTTCACCAAAAAAAAAA
```

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in pharmacology, biochemistry, medical science, or related fields are intended to be within the scope of the following claims.

What is claimed is:

1. A method of preparing a set of amplified DNAs, the method comprising:
   a) providing RNA extracted from a sample of blood, serum, plasma, or saliva from a human subject;
   b) from the RNA, reverse transcribing to form a reference cDNA from at least one reference RNA and to form marker cDNA from up to eight marker RNAs, wherein the up to eight marker RNAs are selected from the group consisting of GAGE12D, FAM83A, LRG1, MAGEA4, XAGE-1 d, SFTPB, AKAP4, and CYP24A1 marker RNAs, wherein:
      GAGE12D marker RNA is reverse transcribed using a first GAGE12D-specific primer hybridized to GAGE12D RNA within a sequence corresponding to SEQ ID NO:32,
      FAM83A marker RNA is reverse transcribed using a first FAM83A-specific primer hybridized to FAM83A RNA within a sequence corresponding to SEQ ID NO:31,
      LRG1 marker RNA is reverse transcribed using a first LRG1-specific primer hybridized to LRG1 RNA within a sequence corresponding to SEQ ID NO:33,
      MAGEA4 marker RNA is reverse transcribed using a first MAGEA4-specific primer hybridized to MAGEA4 RNA within a sequence corresponding to SEQ ID NO:34,
      XAGE-1 d marker RNA is reverse transcribed using a first XAGE-1 d-specific primer hybridized to XAGE-1 d RNA within a sequence corresponding to SEQ ID NO:36,
      SFTPB marker RNA is reverse transcribed using a first SFTPB-specific primer hybridized to SFTPB RNA within a sequence corresponding to SEQ ID NO:35,
      AKAP4 marker RNA is reverse transcribed using a first AKAP4-specific primer hybridized to AKAP4 RNA within a sequence corresponding to SEQ ID NO:28, and
      CYP24A1 marker RNA is reverse transcribed using a first CYP24A1-specific primer hybridized to CYP24A1 RNA within a sequence corresponding to SEQ ID NO:30;
   c) amplifying up to eight marker DNAs from the marker cDNA; and
   d) amplifying reference DNA from the reference cDNA, wherein the reverse transcribing and the amplifying occur in one or more reaction mixtures comprising:
      i) primer oligonucleotides for reverse transcribing the reference RNA and for amplifying reference DNA from the at least one reference cDNA, and primer oligonucleotides for reverse transcribing the up to eight marker RNAs and for amplifying the up to eight marker DNAs from the marker cDNA, wherein the primer oligonucleotides comprise up to eight primer pairs selected from:
         the first GAGE12D-specific primer and a second GAGE12D-specific primer complementary to SEQ ID NO:32 or its complement,
         the first FAM83A-specific primer and a second FAM83A-specific primer complementary to SEQ ID NO:31 or its complement,
         the first LRG1-specific primer and a second LRG1-specific primer complementary to SEQ ID NO:33 or its complement,
         the first MAGEA4-specific primer and a second MAGEA4-specific primer complementary to SEQ ID NO:34 or its complement,
         the first XAGE-1 d-specific primer and a second XAGE-1 d-specific primer complementary to SEQ ID NO:36 or its complement,
         the first SFTPB-specific primer and a second SFTPB-specific primer complementary to SEQ ID NO:35 or its complement,
         the first AKAP4-specific primer and a second AKAP4-specific primer complementary to SEQ ID NO:28 or its complement, and
         the first CYP24A1-specific primer and a second CYP24A1-specific primer complementary to SEQ ID NO:30 or its complement,
      ii) reverse transcriptase; and
      iii) thermostable DNA polymerase.

2. The method of claim 1, wherein reverse transcribing RNAs and amplifying DNAs from cDNAs occur in a single reaction mixture.

3. The method of claim 1, wherein amounts of marker and reference DNAs amplified from marker and reference cDNAs are measured in real time during thermal cycling.

4. The method of claim 3, wherein each of the one or more reaction mixtures further comprises: nucleic acid probe oligonucleotides complementary to the marker and reference DNAs amplified from the marker and reference cDNAs.

5. The method of claim 4, wherein the nucleic acid probe oligonucleotides comprise reporter molecules.

6. The method of claim 5, wherein the reporter molecules comprise fluorophores.

7. The method of claim 5, wherein the reporter molecules comprise flap sequences.

8. The method of claim 7, wherein amounts of marker and reference DNA amplified from marker and reference cDNAs are measured in a PCR-flap assay occurring in the one or more reaction mixtures, wherein each of the one or more reaction mixtures further comprises FEN-1 endonuclease; and one or more FRET cassettes.

9. The method of claim 8, wherein amounts of marker and reference DNA amplified from marker and reference cDNAs are all measured in a single reaction mixture.

10. The method of claim 8, wherein amounts of each of the up to eight marker DNAs amplified from the marker cDNA are all measured in separate reaction mixtures.

11. The method of claim 10, wherein an amount of a marker DNA amplified from the marker cDNA and an amount of reference DNA amplified from the at least one reference cDNA are measured in each of the separate reaction mixtures.

12. The method of claim 1, wherein the up to eight marker RNAs comprises one or more marker RNAs selected from GAGE12D, FAM83A, LRG1, and MAGEA4 marker RNAs.

13. The method of claim 1, wherein the up to eight marker RNAs comprises one or more marker RNAs selected from XAGE-1 d, SFTPB, AKAP4, and CYP24A1 marker RNAs.

14. The method of claim 1, wherein the at least one reference RNA is selected from the group consisting of CASC3 mRNA, β-actin mRNA, U1 snRNA and U6 snRNA.

15. The method of claim 1, wherein the sample is a cell-free sample.

16. The method of claim 1, wherein the reverse transcriptase is MMLV reverse transcriptase.

\* \* \* \* \*